US008609827B2

(12) United States Patent
Calvert et al.

(10) Patent No.: US 8,609,827 B2
(45) **Date of Patent: *Dec. 17, 2013**

(54) INFECTIOUS CDNA CLONE OF NORTH AMERICAN PORCINE REPRODUCTIVE AND RESPIRATORY SYNDROME (PRRS) VIRUS AND USES THEREOF

(75) Inventors: Jay Gregory Calvert, Otsego, MI (US); Michael G. Sheppard, Surf Beach (AU); Siao-Kun W. Welch, Kalamazoo, MI (US); Raymond R. R. Rowland, Manhattan, KS (US); Dal-Young Kim, Birmingham, AL (US)

(73) Assignee: Zoetis LLC, Florham Park, NJ (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/615,504

(22) Filed: Nov. 10, 2009

(65) Prior Publication Data

US 2011/0040079 A1 Feb. 17, 2011

Related U.S. Application Data

(63) Continuation of application No. 11/586,328, filed on Oct. 25, 2006, now Pat. No. 7,618,797, which is a continuation-in-part of application No. 11/366,851, filed on Mar. 1, 2006, now Pat. No. 7,691,389.

(51) Int. Cl.
*C07H 21/04* (2006.01)

(52) U.S. Cl.
USPC .......................................................... 536/23.72

(58) Field of Classification Search
None
See application file for complete search history.

(56) References Cited

U.S. PATENT DOCUMENTS

| | | | | |
|---|---|---|---|---|
| 3,137,631 | A | 6/1964 | Soloway | 167/83 |
| 3,959,457 | A | 5/1976 | Speaker et al. | 424/19 |
| 4,016,100 | A | 4/1977 | Suzuki et al. | 252/318 |
| 4,205,060 | A | 5/1980 | Monsimer et al. | 424/14 |
| 4,452,747 | A | 6/1984 | Gersonde et al. | 264/4.1 |
| 4,606,940 | A | 8/1986 | Frank et al. | 427/213.32 |
| 4,744,933 | A | 5/1988 | Rha et al. | 264/4.3 |
| 4,921,706 | A | 5/1990 | Roberts et al. | 424/450 |
| 4,927,637 | A | 5/1990 | Morano et al. | 424/450 |
| 4,944,948 | A | 7/1990 | Uster et al. | 424/450 |
| 5,008,050 | A | 4/1991 | Cullis et al. | 264/4.3 |
| 5,009,956 | A | 4/1991 | Baumann | 428/402.2 |
| 5,132,117 | A | 7/1992 | Speaker et al. | 424/490 |
| 5,998,601 | A | 12/1999 | Murtaugh et al. | 536/23.72 |
| 6,015,686 | A | 1/2000 | Dubensky, Jr. et al. | 435/69.1 |
| 6,042,830 | A | 3/2000 | Chladek et al. | 424/184.1 |
| 6,268,199 | B1 | 7/2001 | Meulenberg et al. | 435/235.1 |
| 6,500,662 | B1 | 12/2002 | Calvert et al. | |
| 7,132,106 | B2 | 11/2006 | Calvert et al. | |
| 7,232,680 | B2 | 6/2007 | Calvert et al. | |
| 8,110,390 | B2 | 2/2012 | Faaberg et al. | |

FOREIGN PATENT DOCUMENTS

| | | | | |
|---|---|---|---|---|
| EP | 839912 | A1 | | 5/1998 |
| EP | 0839912 | | * | 6/1998 |
| JP | 8-168381 | | | 7/1996 |
| JP | 9-507853 | | | 8/1997 |
| JP | 9-313188 | | | 12/1997 |
| JP | 10-504191 | | | 4/1998 |
| JP | 10-113194 | | | 5/1998 |
| WO | WO92/21375 | | | 12/1992 |
| WO | WO93/03760 | | | 3/1993 |
| WO | WO95/28227 | | | 10/1995 |
| WO | WO96/04010 | | | 2/1996 |
| WO | WO96/06619 | | | 3/1996 |
| WO | WO 96/40932 | | | 12/1996 |
| WO | WO98/55626 | | | 12/1998 |
| WO | WO 2007/002321 | A2 | | 1/2007 |

OTHER PUBLICATIONS

U.S. Appl. No. 60/694,021, filed Jun. 24, 2005, Han et al.

Chen, Z., X. Zhou, et al. (2010), "Immunodominant epitopes in nsp2 of porcine reproductive and respiratory syndrome virus are dispensable for replication, but play an important role in modulation of the host immune response." Journal of General Virology 91: 1047-1057.

Faaberg, K. S., M. E. Kehrli, et al. (2010). "In vivo growth of porcine reproductive and respiratory syndrome virus engineered nsp2 deletion mutants," Virus Research 154(1-2): 77-85.

Guo, B., A. C. Vorwald, et al. (2011). "Large scale parallel pyrosequencing technology: PRRSV strain VR-2332 nsp2 deletion mutant stability in swine." Virus Research 161(2): 162-169.

Murtaugh, et al., EMBL Online Database, U87392, PRRS virus strain VR-2332 complete genome, Nov. 19, 1998 last update Version 4 (D5).

Allende, et al., EMBL Online Database, AF046869, PRRS virus 16244B, complete genome, Oct. 21, 1998 last update Version 1 (D6).

Choi et al., Journal of Virology, vol. 80(2), pp. 723-736, 2006 (D7).

Nelsen et al., Journal of Virology 73(1): pp. 270-280, 1999 (D8).

Nielsen et al., Journal of Virology 77(6): pp. 3702-3711, 2003 (D9).

Tan et al., Virus Genes 22(2): pp. 209-217, 2001 (D10).

Abstract 176 from the CRWAD 82nd Annual Meeting, Nov. 2001 (D11).

Abstract P.6.6 from the IXth International Symposium on Nidoviruses, May 2003 (D12).

Han et al., Journal of Virology 83(18): pp. 9449-9463, 2009 (D14).

Posthuma et al., Journal of Virology 82(9): pp. 4480-4491, 2008 (D15).

Pei et al., Virology 389: pp. 91-99, 2009 (D16).

Kapur et al., Journal of General Virology, vol. 77, pp. 1271-1276, 1996.

(Continued)

*Primary Examiner* — Shanon A Foley

(74) *Attorney, Agent, or Firm* — Barbara L. Renda; E. Victor Donahue

(57) ABSTRACT

The invention provides isolated polynucleotide molecules that comprise a DNA sequence encoding an infectious RNA sequence encoding a genetically-modified North American PRRS virus, wherein the polynucleotide molecule lacks at least one detectable antigenic epitope of North American PRRS virus. The invention also provides vaccines comprising genetically modified North American PRRS virus, RNA molecules, plasmids and viral vectors comprising the isolated polynucleotide molecules. Also provided are isolated polynucleotide molecules further comprising at least one nucleotide sequence that encodes a detectable heterologous antigenic epitope, and vaccines comprising North American PRRS virus, RNA molecules, plasmids and viral vectors comprising such isolated polynucleotide molecules.

7 Claims, 4 Drawing Sheets

(56) References Cited

OTHER PUBLICATIONS

Ausubel, et al., "Current Protocols in Molecular Biology," Greene Publishing Associates & Wiley Interscience, NY (1989).

Allende, R .et al., EMBL online database. AF046869 PRRS virus 16244B, complete genome Oct. 21, 1998.

Chasin, M., et al., "Biodegradable Polymers as Drug Delivery Systems." *Drugs and the Pharmaceutical Sciences*, vol. 45 (1990).

Coligan, JE., et al, Current Protocols in Immunology John Wiley & Sons, Inc. (1998).

Collins, J.E., at al., "Isolation of swine infertility and respiratory syndrome virus (isolate ATCC VR.23 2) in North America and experimental reproduction of the disease in gnotobiotic pigs." *J. Vet. Diagn. Invest.*, 4:117-126 (1992).

den Boon JA, et at., *J. Virol*, 65(6):2910-2920 (1991).

Dumb, A., et al., "Polymers for Advanced Technologies," 3:279-292(1992).

Erlich, "PCR Technology," Academic Press, Inc. 1992.

Enjuanes et al., *Journal of Biotechnology* 88:183-203, 2001.

Innis, et al., "PCR Strategies," Academic Press, Inc. (1995).

Janneke, JM, et al., "Lelysted Virus, the Causative Agent of Porcine Epidemic Abortion and Respiratory , (PEARS), is Related to LdV and EAV," *Virology*, 192, 62-67 (1993).

Kim, H.S., et al., "Enhanced replication of porcine reproductive and respiratory syndrome (PRRS) virus in a homogeneous subpopulation of MA-104 cell line," *Arch Virol.*, 133:477-483 (1993).

Kwang, J., et al., "Cloning, expression, and sequence analysis of the ORF4 gene of the porcine reproductive and respiratory syndrome virus MN-lb" Journal Bet. Diagn. Invest. 6:293-296_(1994).

Kreutz, L.C. "Cellular membrane factors are the major determinants of porcine reproductive and respiratory syndrome virus tropism," Virus Research 53:121-128, 1998.

Maniatis, et al., Molecular Cloning, A Laboratory Manual, Cold Spring Harbor Laboratory Press, Cold Spring Harbor, NY (1989).

Mardassi, H., 1995., Arch. Virol. 140: 1405-1418.

Meulenberg, J.J.M. et at., "Lelystad Virus, the Causative Agent of Porcine Epidemic Abortion and Respiratory Syndromes (PEARS). is Related to LdV and EAV." *Virology*, 192:62-72 (1993).

Murtaugh, MP et al., "Comparison of the structural protein coding sequences of the VR-2332 and Lelystad virus strains of the PRRS virus," *Arch Virol 40*:1 pp. 1451-1460 (1995).

Meng. X.J. et at., "Molecular cloning and nucleotide sequencing of the 3' -terminal genotnic RNA of the porcine reproductive and respiratory syndrome virus." *J. Gen. Virol.*, 1795-1801(1994).

Meulenberg, J J M. et al., *Journal of Virology* 72,380-387 (1988).

Murtaugh, EMBL online database, U87392, PRRS virus strain VR-2332 complete genome. Jan. 8, 1998.

Nelson, CJ, et al., GenBank, AF066183, Porcine reproductive and respiratory syndrome virus Resp PRRS MLV, complete genome, May 15, 1998.

Remington, "Pharmaceutical Science," $18^{th}$ ed. Mack Publishing (1990).

Sambrook, et al., "Molecular Cloning: A Laboratory manual," $2^{nd}$ ed., Cold Spring Harbor Laboratory Press, Cold Spring Harbor NY (1989).

Snijder, E.J. et at., "The molecul a biology of arteriviruses," *Journal of General Virology*, 79:961-979 (1998).

Suarez, P. et al., "Phylogenetic relationships of European strains of porcine reproductive and respiratory syndrome virus (PRRSV) inferred from DNA sequences of putative ORF-5 and ORF-7 genes," *Virus Research*, 42:159-165 (1996).

Terpstra, C. et al., Experimental reproduction of porcine epidemic abortion and respiratory syndrome (mystery swine disease) by infection with Lelystad virus: Koch's postulates fulfilled, *Vet. Quart.*, 13:131-136 (1991).

Van Dinten L.C., et al., An infectious arterivirus cDNA clone: identification of a replicase point mutation, which abolishes discontinuous mRNA transcription. Proceedings of the National Academy of Science USA 94: 991-996, (1997).

Wensvoort, G et al., Mystery swine disease in the Netherlands: the isolation of Lelystad virus, *Vet. Quart*, 13:121-130(1991).

Yang SX et al., Comparative sequence analysis of open reading frames 2 to 7 of the modified live vaccine virus and other North American isolates of the porcine reproductive and respiratory syndrome virus, Archives of Virology, New York, NY, US vol. 143, No. 3, 1998, pp. 601-612.

* cited by examiner

INFECTIOUS CDNA CLONE OF NORTH AMERICAN PORCINE REPRODUCTIVE AND RESPIRATORY SYNDROME (PRRS) VIRUS AND USES THEREOF

CROSS-REFERENCE TO RELATED APPLICATIONS

The present application is a continuation of U.S. patent application Ser. No. 11/586,328, filed Oct. 25, 2006, now U.S. Pat. No. 7,618,797, which is a continuation-in-part of U.S. patent application Ser. No. 11/366,851, filed Mar. 1, 2006, now U.S. Pat. No. 7,691,389. The disclosure of the Ser. No. 11/586,328 application is incorporated by reference in its entirety.

FIELD OF THE INVENTION

The present invention is in the field of animal health and is directed to infectious cDNA clones of positive polarity RNA viruses and the construction of vaccines, in particular, swine vaccines, using such cDNA clones.

BACKGROUND OF THE INVENTION

Porcine reproductive and respiratory syndrome (PRRS) is a new disease of swine, first described in 1987 in North America and in 1990 in Europe. The disease has since spread to Asia and affects most of the major swine producing countries of the world. Primary symptoms are reproductive problems in sows and gilts, including late term abortions, stillbirths and mummies, and litters of small weak pigs which are born viremic and often fail to survive. In addition, the syndrome manifests itself as a respiratory disease in young pigs which spreads horizontally and causes fever, lethargy, labored breathing, loss of appetite, slow growth, and occasionally death, often in association with other respiratory pathogens. The disease furthermore can be transmitted to sows and gilts via the semen of infected boars, either naturally or by artificial insemination. For these, and other reasons, PRRS has proven to be a difficult disease to control and therefore one of the most economically damaging diseases to the swine industry.

The causative agent of PRRS is the PRRS virus, which exists as two genetically and serologically distinct types (Murtaugh, M. P. et al., 1995, Arch-Virol. 140, 1451-1460; Suarez, P. et al., 1996, Virus Research 42:159-165). The two types are believed to have first entered swine populations independently, one in North America and the other in Europe, in the 1980's, from unknown biological reservoirs, possibly of rodent or avian origin. The European type, represented by the prototype "Lelystad Virus", was isolated and sequenced in the Netherlands in 1991 (Terpstra, C. et al., 1991, Vet. Quart. 13:131-136; Wensvoort, G. et al., 1991, Vet. Quart. 13:121-130; Wensvoort, G. et al., WO 92/213751992 (PCT/NL92/00096), 1992; Meulenberg, J. J. M. et al., 1993, Virol. 192: 62-72).

Both the North American PRRS virus and the European PRRS virus are classified within the family Arteriviridae, which also includes equine arteritis virus, lactate dehydrogenase-elevating virus, and simian haemorrhagic fever virus. The arteriviruses are in turn placed within turn placed within the order Nidovirales, which also includes the coronaviruses and toroviruses. The nidoviruses are enveloped viruses having genomes consisting of a single strand of positive polarity RNA. The genomic RNA of a positive-stranded RNA virus fulfills the dual role in both storage and expression of genetic information. No DNA is involved in replication or transcription in nidoviruses. The reproduction of nidoviral genomic RNA is thus a combined process of genome replication and mRNA transcription. Moreover, some proteins are translated directly from the genomic RNA of nidoviruses. The molecular biology of the family Arteriviridae has recently been reviewed by Snijder and Meulenberg (Snijder, E. J. and Meulenberg, J. J. M., 1998, Journal of General Virology 79:961-979).

Currently available commercial vaccines against PRRS are either conventional modified live virus (cell culture, attenuated) or conventional killed (inactivated cell culture preparations of virulent virus). Several of these vaccines have been criticized based on safety and/or efficacy concerns. The development of a second generation of PRRS vaccines, based upon specific additions, deletions, and other modifications to the PRRS genome, is therefore highly desirable. However, since the PRRS viruses do not include any DNA intermediates during their replication, such vaccines have thus far awaited the construction of full-length cDNA clones of PRRS viruses for manipulation by molecular biology techniques at the DNA level. Very recently, a full-length infectious cDNA clone of the European PRRS virus has been reported (Meulenberg, J. J. M. et al., 1998, supra; Meulenberg, J. J. M. et al., 1988, J. Virol. 72, 380-387.).

The preceding publications, as well as all other references discussed below in this application, are hereby incorporated by reference in their entireties.

SUMMARY OF THE INVENTION

The subject invention provides an isolated polynucleotide molecule comprising a DNA sequence encoding an infectious RNA molecule encoding a North American PRRS virus that is genetically modified such that when it infects a porcine animal it is unable to produce PRRS in the animal yet able to elicit an effective immunoprotective response against a PRRS virus in the porcine animal, wherein said DNA sequence is SEQ ID NO:1 or a sequence homologous thereto, except that it lacks at least one DNA sequence encoding a detectable antigenic epitope of North American PRRS virus.

The subject invention further provides an isolated polynucleotide molecule where at least one DNA sequence encoding a detectable antigenic epitope of North American PRRS virus in ORF 1a or ORF 1b within said DNA sequence is deleted.

The subject invention further provides an isolated polynucleotide molecule where at least one DNA sequence encoding a detectable antigenic epitope of North American PRRS virus in the nonstructural protein 2 coding region of ORF1a within said DNA sequence is deleted.

The subject invention further provides an isolated polynucleotide molecule where at least one DNA sequence encoding a detectable antigenic epitope of North American PRRS virus in the hypervariable region in the nonstructural protein 2 coding region of ORF1a within said DNA said DNA sequence is deleted.

The subject invention further provides an isolated polynucleotide molecule where the DNA sequence encoding amino acids 628 and 759 in the hypervariable region in the nonstructural protein 2 coding region of ORF1a within said DNA sequence is deleted.

The subject invention further provides a vaccine for protecting a porcine animal from infection by a PRRS virus, wherein said vaccine comprises a genetically modified North American PRRS virus encoded by an infectious RNA molecule encoded by the isolated polynucleotide molecule as described above; an infectious RNA molecule encoded by the isolated polynucleotide molecule as described above; an isolated polynucleotide molecule as described above in the form of a plasmid, or a viral vector comprising the isolated polynucleotide molecule as described above, and a carrier acceptable for veterinary use.

The subject invention also provides an isolated polynucleotide molecule comprising a DNA sequence encoding an infectious RNA molecule encoding a North American PRRS virus that is genetically modified such that when it infects a porcine animal it is unable to produce PRRS in the animal yet able to elicit an effective immunoprotective response against a PRRS virus in the porcine animal, wherein the DNA sequence is SEQ ID NO:1 or a sequence homologous thereto, except that it lacks at least one DNA sequence encoding a detectable antigenic epitope of North American PRRS virus, wherein it further comprises at least one nucleotide sequence that encodes a detectable heterologous antigenic epitope.

The present invention further provides an isolated polynucleotide molecule comprising at least one nucleotide sequence encoding a heterologous antigenic epitope, wherein said nucleotide sequence encoding a heterologous antigenic epitope is inserted in ORF 1a or ORF 1b within said DNA sequence encoding an infectious RNA molecule encoding a North American PRRS virus.

The present invention further provides an isolated polynucleotide molecule comprising at least one nucleotide sequence encoding a heterologous antigenic epitope, wherein said nucleotide sequence encoding a heterologous antigenic epitope is inserted in the nonstructural protein 2 coding region of ORF 1a within said DNA sequence encoding an infectious RNA molecule encoding a North American PRRS virus.

The present invention further provides an isolated polynucleotide molecule comprising at least one nucleotide sequence encoding a heterologous antigenic epitope, wherein said nucleotide sequence encoding a heterologous antigenic epitope is inserted in the hypervariable region in the nonstructural protein 2 coding region of ORF 1a within said DNA sequence encoding an infectious RNA molecule encoding a North American PRRS virus.

The present invention further provides an isolated polynucleotide molecule comprising at least one nucleotide sequence encoding a heterologous antigenic epitope, wherein said nucleotide sequence encoding a heterologous antigenic epitope is inserted in the hypervariable region in the nonstructural protein 2 coding region of ORF 1a between the DNA sequence encoding amino acids 628 and 759 in the hypervariable region in the nonstructural protein 2 coding region of ORF1a within said DNA sequence.

The present invention further provides a vaccine for protecting a porcine animal from infection by a PRRS virus, wherein said vaccine comprises a genetically modified North American PRRS virus encoded by an infectious RNA molecule encoded by an isolated polynucleotide molecule as described above, an infectious RNA molecule encoded by an isolated polynucleotide molecule as described above, an isolated polynucleotide molecule as described above, or a viral vector comprising an isolated polynucleotide molecule as described above, and a carrier acceptable for veterinary use.

The present invention also provides a diagnostic kit for differentiating between porcine animals vaccinated with the above described vaccines and porcine animals infected with field strains of PRRS virus. Said kit contains as one of its components at least one peptide having a sequence comprising the 132 amino acid region deleted within the PRRS virus strains presently described. Alternative, the kit can have as one of its components the corresponding peptide from any PRRS virus strain. The kit can otherwise have as one of its components a smaller peptide corresponding to a portion of the 132 amino acid sequence comprising the nsp2 deletion, from 10 amino acid residues or upward in length. The peptide can additionally be in the form of a fusion protein.

DETAILED DESCRIPTION OF THE INVENTION

Figure 1:
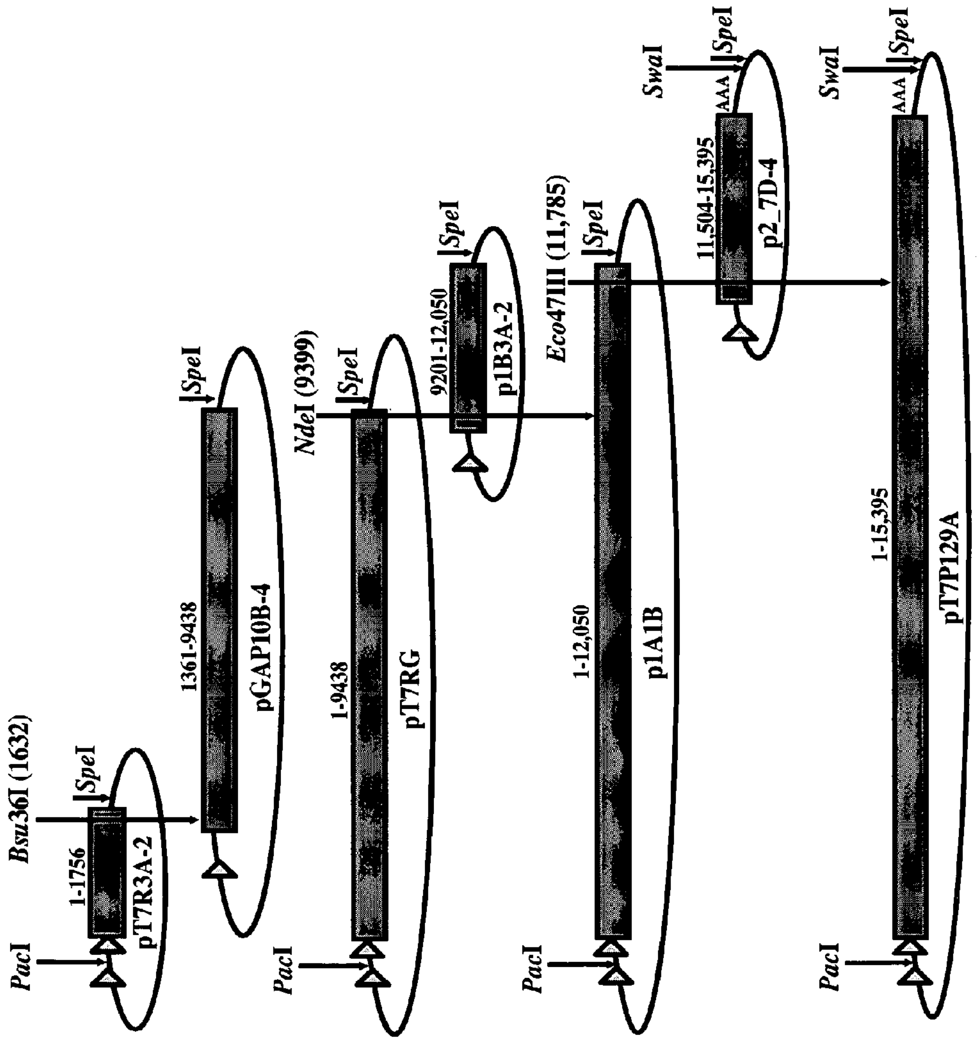
FIG. 1: Cloning strategy for construction of full-length infectious cDNA clone of North American PRRS virus, pT7P129A. Arrowheads represent T7 promoter sequences.

Production and manipulation of the isolated polynucleotide molecules described herein are within the skill in the art and can be carried out according to recombinant techniques described, among other places, in Maniatis, et al., 1989, *Molecular Cloning, A Laboratory Manual*, Cold Spring Harbor Laboratory Press, Cold Spring Harbor, N.Y.; Ausubel, et al., 1989, *Current Protocols In Molecular Biology*, Greene Publishing Associates & Wiley Interscience, NY; Sambrook, et al., 1989, *Molecular Cloning: A Laboratory Manual,* 2d ed., Cold Spring Harbor Laboratory Press, Cold Spring Harbor, N.Y.; Innis et al. (eds), 1995, *PCR Strategies*, Academic Press, Inc., San Diego; and Erlich (ed), 1992, *PCR Technology*, Oxford University Press, New York, all of which are incorporated herein by reference.

A. Isolated Polynucleotide Molecules and RNA Molecules Encoding Genetically Modified North American PRRS Viruses.

The present invention provides isolated polynucleotide molecules comprising DNA sequences that encode infectious RNA molecules that encode genetically modified North American PRRS viruses.

The subject invention provides an isolated polynucleotide molecule comprising a DNA sequence encoding an infectious RNA molecule that encodes a North American PRRS virus, wherein said DNA sequence is SEQ ID NO:1 or a sequence homologous thereto. The present invention provides an isolated polynucleotide molecule comprising a DNA sequence encoding an infectious RNA molecule that encodes a North American PRRS virus, wherein said DNA sequence is the sequence beginning with and including nucleotide 1 through and including nucleotide 15,416 of SEQ ID NO:1, except that the nucleotide corresponding to nucleotide 12,622 of SEQ ID NO:1 is a guanine instead of an adenine and the nucleotide corresponding to nucleotide 1,559 of SEQ ID NO:1 is a thymine instead of a cytosine. Said DNA sequence encodes an infectious RNA molecule that is the RNA genome of the North American PRRS isolate P129.

It is understood that terms herein referring to nucleic acid molecules such as "isolated polynucleotide molecule", "nucleotide sequence", "open reading frame (ORF)", and the like, unless otherwise specified, include both DNA and RNA molecules and include both single-stranded and double-stranded molecules. Also, when reference to a particular sequence from the "Sequence Listing" section of the subject application is made, it is intended, unless otherwise specified, to refer to both the DNA of the "Sequence Listing", as well as RNA corresponding to the DNA sequence, and includes sequences complementary to the DNA and RNA sequences. In such contexts in this application, "corresponding to" refers to sequences of DNA and RNA that are identical to one another but for the fact that the RNA sequence contains uracil in place of thymine and the backbone of the RNA molecule contains ribose instead of deoxyribose.

For example, SEQ ID NO:1 is a DNA sequence corresponding to the RNA genome of a North American PRRS virus. Thus, a DNA sequence complementary to the DNA sequence set forth in SEQ ID NO:1 is a template for, i.e. is complementary to or "encodes", the RNA genome of the North American PRRS virus (i.e., RNA that encodes the North American PRRS virus). Nonetheless, a reference herein to SEQ ID NO:1 includes both the RNA sequence corresponding to SEQ ID NO:1 and a DNA sequence complementary to SEQ ID NO:1.

Furthermore, when reference is made herein to sequences homologous to a sequence in the Sequence Listing, it is to be understood that sequences homologous to a sequence corresponding to the sequence in the Sequence Listing and sequences homologous to a sequence complementary to the sequence in the Sequence Listing are also included.

An "infectious RNA molecule", for purposes of the present invention, is an RNA molecule that encodes the necessary elements for viral replication, transcription, and translation into a functional virion in a suitable host cell, provided, if necessary, with a peptide or peptides that compensate for any genetic modifications, e.g. sequence deletions, in the RNA molecule.

An "isolated infectious RNA molecule" refers to a composition of matter comprising the aforementioned infectious RNA molecule purified to any detectable degree from its naturally occurring state, if such RNA molecule does indeed occur in nature. Likewise, an "isolated polynucleotide molecule" refers to a composition of matter comprising a polynucleotide molecule of the present invention purified to any detectable degree from its naturally occurring state, if any.

For purposes of the present invention, the nucleotide sequence of a second polynucleotide molecule (either RNA or DNA) is "homologous" to the nucleotide sequence of a first polynucleotide molecule where the nucleotide sequence of the second polynucleotide molecule encodes the same polyaminoacid as the nucleotide sequence of the first polynucleotide molecule as based on the degeneracy of the genetic code, or when it encodes a polyaminoacid that is sufficiently similar to the polyaminoacid encoded by the nucleotide sequence of the first polynucleotide molecule so as to be useful in practicing the present invention. For purposes of the present invention, a polynucleotide molecule is useful in practicing the present invention where it can be used as a diagnostic probe to detect the presence of the North American PRRS virus in a fluid or tissue sample of an infected pig, e.g. by standard hybridization or amplification techniques. It is to be understood that the polyaminoacid encoded by the nucleotide sequence of the polynucleotide molecule can comprise a group of two or more polyaminoacids. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). Preferably, a homologous nucleotide sequence has at least about 75% nucleotide sequence identity, even more preferably at least about 85% nucleotide sequence identity. Since the genetic code is degenerate, a homologous nucleotide sequence can include any number of "silent" base changes, i.e. nucleotide substitutions that nonetheless encode the same amino acid. A homologous homologous nucleotide sequence can further contain non-silent mutations, i.e. base substitutions, deletions, or additions resulting in amino acid differences in the encoded polyaminoacid, so long as the sequence remains at least about 70% identical to the polyaminoacid encoded by the first nucleotide sequence or otherwise is useful for practicing the present invention. Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 if it hybridizes to the complement of SEQ ID NO:1 under moderately stringent conditions, e.g., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et al. above), or conditions which will otherwise result in hybridization of sequences that encode a North American PRRS virus as defined below. In another embodiment, a second nucleotide sequence is homologous to SEQ ID NO:1 if it hybridizes to the complement of SEQ ID NO:1 under highly stringent conditions, e.g. hybridization to filter-bound DNA in 0.5 M $NaHPO_4$, 7% SDS, 1 mM EDTA at 65° C., and washing in 0.1×SSC/0.1% SDS at 68° C. (Ausubel et al., above).

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "PRRS" encompasses disease symptoms in swine caused by a PRRS virus infection. Examples of such symptoms include, but are not limited to, abortion in pregnant females, and slow growth, respiratory difficulties, loss of appetite, and mortality in young pigs. As used herein, a PRRS virus that is "unable to produce PRRS" refers to a virus that can infect a pig, but which does not produce any disease symptoms normally associated with a PRRS infection in the pig, or produces such symptoms, but to a lesser degree, or produces a fewer number of such symptoms, or both.

The terms "porcine" and "swine" are used interchangeably herein and refer to any animal that is a member of the family Suidae such as, for example, a pig. "Mammals" include any warm-blooded vertebrates of the Mammalia class, including humans.

The term "PRRS virus", as used herein, unless otherwise indicated, means any strain of either the North American or European PRRS viruses.

The term "field strain" or "field strains", as used herein, unless otherwise indicated, means any strain of either North American or European PRRS virus which occurs in nature, and is infectious to a pig.

The term "North American PRRS virus" means any PRRS virus having genetic characteristics associated with a North American PRRS virus isolate, such as, but not limited to the PRRS virus that was first isolated in the United States around the early 1990's (see, e.g., Collins, J. E., et al., 1992, J. Vet. Diagn. Invest. 4:117-126); North American PRRS virus isolate isolate MN-1b (Kwang, J. et al., 1994, *J. Vet. Diagn. Invest.* 6:293-296); the Quebec IAF-exp91 strain of PRRS (Mardassi, H. et al., 1995, *Arch. Virol.* 140:1405-1418); and North American PRRS virus isolate VR 2385 (Meng, X.-J et a, 1994, *J. Gen. Virol.* 75:1795-1801). Genetic characteristics refers to genomic nucleotide sequence similarity and amino acid sequence similarity shared by North American PRRS virus strains. For purposes of the present invention, a North American PRRS virus is a virus that is encoded by an RNA sequence the same as or homologous to SEQ ID NO:1, wherein the term "homologous" is as defined previously. Thus, strains of North American PRRS viruses have, preferably, at least about 70% genomic nucleotide sequence identity with SEQ ID NO:1, and more preferably at least about 75% genomic nucleotide sequence identity with SEQ ID NO:1, at least about 85% genomic nucleotide sequence identity with SEQ ID NO:1 being even more preferred.

The term "European PRRS virus" refers to any strain of PRRS virus having the genetic characteristics associated with the PRRS virus that was first isolated in Europe around 1991 (see, e.g., Wensvoort, G., et al., 1991, Vet. Q. 13:121-130). "European PRRS virus" is also sometimes referred to in the art as "Lelystad virus".

Unless otherwise indicated, a North American PRRS virus is "useful in practicing the present invention" if its characteristics are within the definition of a North American PRRS virus set forth herein. For example, a virus encoded by one of the isolated polynucleotide molecules of the present invention is a "North American PRRS virus useful in practicing the present invention" if it, e.g., has genetic characteristics associated with a North American PRRS virus.

Other polyaminoacids are "useful in practicing the present invention", e.g., peptides encoded by polynucleotide sequences homologous to North American PRRS virus ORFs, if they can compensate for an RNA molecule encoding a genetically modified PRRS virus, deficient in a gene essential for expressing functional PRRS virions, in a transfected host cell so that functional PRRS virions can be generated by the cell.

The term "open reading frame", or "ORF", as used herein, means the minimal nucleotide sequence required to encode a particular PRRS virus protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, and avian cells, and are described in further detail below.

A "functional virion" is a virus particle that is able to enter a cell capable of hosting a PRRS virus, and express genes of its particular RNA genome (either an unmodified genome or a genetically modified genome as described herein) within the cell. Cells capable of hosting a PRRS virus include porcine alveolar macrophage cells and MARC 145 monkey kidney cells. Other mammalian or avian cells, especially other porcine cells, may also serve as suitable host host cells for PRRS virions.

The isolated polynucleotide molecules of the present invention encode North American PRRS viruses that can be used to prepare live, killed, or attenuated vaccines using art-recognized methods for protecting swine from infection by a PRRS virus, as described in further detail below. These isolated polynucleotide molecules are also useful as vectors for delivering heterologous genes into mammals, including swine, or birds, as is also described in detail below. Furthermore, these isolated polynucleotide molecules are useful because they can be mutated using molecular biology techniques to encode genetically-modified North American PRRS viruses useful, inter alia, as vaccines for protecting swine from PRRS infection. Such genetically-modified North American PRRS viruses, as well as vaccines comprising them, are also described in further detail below.

The term "genetically modified", as used herein and unless otherwise indicated, means genetically mutated, i.e. having one or more nucleotides replaced, deleted and/or added. Polynucleotide molecules can be genetically mutated using recombinant techniques known to those of ordinary skill in the art, including by site-directed mutagenesis, or by random mutagenesis such as by exposure to chemical mutagens or to radiation, as known in the art. In one embodiment, genetic modification of the North American PRRS virus of the present invention renders the virus unable to replicate effectively, or reduces its ability to replicate effectively, in a bird or mammal in which the wild-type virus otherwise can effectively replicate. In another embodiment, the genetically modified North American PRRS virus of the present invention remains able to replicate effectively in birds or mammals infected therewith. "Effective replication" means the ability to multiply and produce progeny viruses (virions) in an infected animal, i.e. the ability to "productively infect" an animal.

The subject invention further provides an isolated polynucleotide molecule comprising a DNA sequence encoding an infectious RNA molecule which encodes a genetically modified North American PRRS virus that is unable to produce PRRS in a porcine animal, wherein the DNA sequence encoding the infectious RNA molecule encoding said North American PRRS virus is SEQ ID NO:1 or a sequence homologous thereto, except that it contains one or more mutations that genetically disable the encoded PRRS virus in its ability to produce PRRS. "Genetically disabled" means that the PRRS virus is unable to produce PRRS in a swine animal infected therewith.

The subject invention also provides an isolated polynucleotide molecule comprising a DNA sequence encoding an infectious RNA molecule which encodes a North American PRRS virus that is genetically modified such that when it infects a porcine animal it: a) is unable to produce PRRS in the animal, and b) is able to elicit an effective immunoprotective response against infection by a PRRS virus in the animal, wherein the DNA sequence encoding said North American PRRS virus is SEQ ID NO:1 or a sequence homologous thereto, except that it contains one or more mutations that genetically disable the encoded PRRS virus in its ability to produce PRRS.

The term "immune response" for purposes of this invention means the production of antibodies and/or cells (such as T lymphocytes) that are directed against, or assist in the decomposition or inhibition of, a particular antigenic epitope or particular antigenic epitopes. The phrases "an effective immunoprotective response", "immunoprotection", and like terms, for purposes of the present invention, mean an immune response that is directed against one or more antigenic epitopes of a pathogen so as to protect against infection by the pathogen in a vaccinated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of vaccination. An effective immunoprotective response can also be induced in an animal already infected with the pathogen at the time of vaccination.

An "antigenic epitope" is, unless otherwise indicated, a molecule that is able to elicit an immune response in a particular animal or species. Antigenic epitopes are proteinaceous molecules, i.e. polyaminoacid sequences, optionally comprising non-protein groups such as carbohydrate moieties and/or lipid moieties.

The term "pathogenically infecting" used herein refers to the ability of a pathogen to infect an animal and cause a disease in the animal. As an example, a PRRS virus is capable of pathogenically infecting a porcine animal since it can cause PRRS in swine. However, although a PRRS virus may be able to infect, either productively or non-productively, a bird or another mammal, such as a human, it does not pathogenically infect any animal other than a porcine animal since it does not cause any disease in animals other than porcine animals.

The genetically modified North American PRRS viruses encoded by the above-described isolated polynucleotide molecules are, in one embodiment, able to elicit an effective immunoprotective response against infection by a PRRS virus. Such genetically modified North American PRRS viruses are preferably able to elicit an effective immunoprotective response against any strain of PRRS viruses, including both European and North American strains.

The present invention provides a mutation or mutations in the isolated polynucleotide molecule encoding the genetically disabled North American PRRS virus that are non-silent and occur in one or more open reading frames of the nucleotide sequence encoding the North American PRRS virus; i.e., the mutation or mutations occur in one or more of the sequences within the nucleotide sequence encoding the North American PRRS virus that are the same as or homologous to ORFs 1a, 1b, 2, 3, 4, 5, 6, or 7 of SEQ ID NO:1. The mutation or mutations may occur in one or more noncoding regions of the North American PRRS virus genome, such as, for example, in the leader sequence of the North American PRRS virus genome; i.e., the mutation or mutations occur within the sequence that is the same as or homologous to the sequence of sequence of nucleotides 1-191 of SEQ ID NO:1. In the same isolated polynucleotide molecule, mutations can occur in both coding and noncoding regions.

As used herein, unless otherwise indicated, "noncoding regions" of the nucleotide sequence encoding the North American PRRS virus refer to those sequences of RNA that are not translated into a protein and those sequences of cDNA that encode such RNA sequences. Coding regions refer to those sequences of RNA from which North American PRRS virus proteins are expressed, and also refer to cDNA that encodes such RNA sequences. Likewise, "ORFs" refer both to RNA sequences that encode North American PRRS virus proteins and to cDNA sequence encoding such RNA sequences.

Determining suitable locations for a mutation or mutations that will encode a North American PRRS virus that is genetically disabled so that it is unable to produce PRRS yet remains able to elicit an effective immunoprotective response against infection by a PRRS virus can be made based on the SEQ ID NO:1 provided herein. One of ordinary skill can refer to the sequence of the infectious cDNA clone of North American PRRS virus provided by this invention, make sequence changes which will result in a mutation, and test the viruses encoded thereby both for their ability to produce PRRS in swine, and to elicit an effective immunoprotective response against infection by a PRRS virus. In so doing, one of ordinary skill can refer to techniques known in the art and also those described and/or exemplified herein.

For example, an ORF of the sequence encoding the infectious RNA molecule encoding the North American PRRS virus can be mutated and the resulting genetically modified North American PRRS virus tested for its ability to cause PRRS. The ORF of a North American PRRS virus encodes proteins as follows: ORF 1a encodes a polyprotein comprising protease function; ORF 1b encodes a polyprotein comprising replicase (RNA polymerase) and helicase functions; ORFs 2, 3, and 4 encode small membrane glycoproteins; ORF 5 encodes a major envelope glycoprotein; ORF 6 encodes a nonglycosylated integral membrane protein; and ORF 7 encodes a nucleocapsid protein. Genetic mutations of one or more of these ORFs can be used in preparing the genetically modified North American PRRS viruses described infra.

The subject invention also provides an isolated polynucleotide molecule comprising a DNA sequence encoding an infectious RNA molecule encoding a North American PRRS virus that is genetically modified such that it lacks at least one DNA sequence encoding a detectable antigenic epitope of North American PRRS virus, wherein the DNA, sequence encoding the RNA molecule encoding the North American PRRS virus is SEQ ID NO:1 or a sequence homologous thereto.

A "detectable antigenic epitope" is, unless otherwise indicated, a molecule that is able to elicit an immune response in a particular animal or species, which immune response is measurable via an assay or method.

In a non-limiting embodiment, the detectable antigenic epitope which is deleted is within ORF 1a or ORF 1b. In another embodiment, the detectable antigenic epitope which is deleted is within the sequences encoding for the nonstructural protein 2 (nsp2), which is part of ORF 1a. In a separate embodiment, the detectable antigenic epitope which is deleted is within the hypervariable C-terminal portion of nsp2. In a further embodiment, the detectable antigenic epitope which is deleted, or lacking, is the DNA sequence encoding any 10 aa polypeptides or longer, up to 400 aa length polypeptides, where the DNA sequence that may be deleted is the DNA that encodes any amino acids from 616 to 752 of the hypervariable region of nsp2. This region, from 616 to 752 of nsp2, is the conserved sub-region within the hypervariable region of nsp2.

One example of such a deletion is Example XI. In Example XI a deletion is described which results in the lack of a DNA sequence encoding amino acids 628 through 759 of nsp2. This deletion is within the region encoding the hypervariable C-terminal portion of nsp2. This Example XI deletion, which lacks the DNA sequence encoding amino acids from 628 to 759 in the hypervariable region is considered as being taken from the region of the DNA sequence encoding amino acids 616 to 752 in the hypervariable region because the region begins in the region of the DNA sequence encoding amino acids 616 to 752 in the hypervariable region. The deleted region can extend beyond the conserved sub-region in either direction, but the entire deleted region should be no greater than the amount of DNA that encodes for a polypeptide of about 400 aa. Table 1 shows the relative positions of some of the nucleotides and amino acids in relation to certain regions of the genome for SEQ. ID. NO. 1.

TABLE 1

Genome coordinates of nsp2 regions based on SEQ ID NO. 1.

| Landmark | Genome position (nucleotides) | Amino acid range (w/in ORF1a) | Amino acid range (w/in nsp2) |
|---|---|---|---|
| Entire genome | 1-15, 450 (1-15, 395 w/o polyA tail) | NA | NA |
| ORF1a | 192-7685 (7491 nt) ATGTCT . . . TGCTAG | 1-2497 (2497 aa) MSGIL . . . QCLNC | NA |
| Nsp2 | 13414262 (2922 nt) GCTGGA . . . CTGGGC | 384-1357 (974 aa) AGKRA . . . GRLLG | 1-974 (974 aa) AGKRA . . . GRLLG |
| Hypervariable region of nsp2 | 2721-3980 (1260 nt) AGATCT . . . CTCTTT | 844-1263 (420 aa) RSDYG . . . LFCLF | 461-880 (420 aa) RSDYG . . . LFCLF |
| Conserved subregion w/in hypervariable region | 3186-3596 (411 nt) TCATCA . . . CGCATC | 999-1135 (137 aa) SSSSS . . . DIPRI | 616-752 (137 aa) SSSSS . . . DIPRI |
| Deletion in Example XI | 3222-3617 (396 nt) CGCCCA . . . AATACC | 1011-1142 (132 aa) RPKYS . . . KIENT | 628-759 (132 aa) RPKYS . . . KIENT |

Such deletions may be anywhere within the hypervariable region, including the region of the DNA encoding the conserved sub-region of amino acids from 616 to 752 in nsp2, and such deletions may extend into the flanking regions as well, provided the DNA encodes at least 10 amino acids from the conserved sub-region or from other locations in the hypervariable region.

In a further embodiment, the detectable antigenic epitope which is removed is taken from the DNA sequence encoding amino acids 628 through 759 of nsp2, which is both within the conserved sub-region and within the region encoding the hypervariable C-terminal portion of nsp2.

In a further embodiment, the detectable antigenic epitope which is deleted is taken from the DNA sequence encoding polypeptides as short as ten amino acids, or as long as the entire hypervariable region of nsp2 which can extend up to 400 amino acids. Specifically the region may be from 10 to 100 aa in length, from 100 to 150, from 150 to 200, from 200 to 300 or from 300 to 400 amino acids in length. For example, the deleted DNA can encode the peptide that comprises amino acids 1-10 of the hypervariable region of the nsp2 peptide. The peptide can be amino acids 2-11 of the hypervariable region. The peptide can be amino acids 3-12 of the hypervariable region. Peptides are selected in this fashion by progressively "walking" down the amino acid sequence of the hypervariable region of nsp2, all of the way through the hypervariable region, more particularly through the region of the DNA encoding the conserved subregion of amino acids from 616 to 752 of nsp2 within the hypervariable region, and it may extend into the flanking regions. A specific example of this is Example XI where the deleted region is the DNA sequence encoding amino acids 628 through 759 in the hypervariable region.

In addition to 10-mer peptides, the deleted fragment can be a DNA encoding 11 amino acid residues in length, beginning with a fragment comprising amino acid 1-11 of the hypervariable region, and progressing to the C-terminal end of the hypervariable region. Similarly, the fragment can be DNA encoding 12, 13, 14, 15, 16, 17, 18, 19, 20 or more residues in length, up to 400 residues in length, and such peptides are readily identifiable by beginning at residue 1 and "walking" down the amino acid sequence of the corresponding hypervariable region of nsp2. Such a strategy can be applied to the corresponding hypervariable region of the nsp2 sequence from any strain of PRRS virus.

The subject invention also provides an isolated polynucleotide molecule comprising a DNA sequence encoding an infectious RNA molecule encoding a North American PRRS virus that is genetically modified such that it lacks at least one DNA sequence encoding a detectable antigenic epitope of North American PRRS virus, wherein it further comprises one or more heterologous antigenic epitopes, wherein the DNA sequence encoding the RNA molecule encoding the North American PRRS virus is SEQ ID NO:1 or a sequence homologous thereto, and further comprising one or more additional nucleotide sequences that each encode a heterologous antigenic epitope, and wherein each heterologous antigenic epitope is capable of inducing an effective immunoprotective response against a particular pathogen in a mammal or a bird.

A pathogen against which an effective immunoprotective response can be induced by means of the above recited aspect of the present invention is any pathogen, such as a virus, bacteria, fungus, or protozoan, capable of causing a disease in a mammal or bird, which pathogen comprises or has associated therewith one or more antigenic epitopes which can be used to induce an effective immunoprotective response against the pathogen in the mammal or bird.

The term "heterologous antigenic epitope" for purposes of the present invention means an antigenic epitope, as defined above, not normally found in a wild-type North American PRRS virus. A nucleotide sequence encoding a heterologous antigenic epitope can be inserted into a North American PRRS viral genome using known recombinant techniques. Antigenic epitopes useful as heterologous antigenic epitopes for the present invention include additional North American PRRS virus antigenic epitopes, antigenic epitopes from European PRRS viruses, antigenic epitopes from swine pathogens other than PRRS viruses, or antigenic epitopes from pathogens that pathogenically infect birds or mammals other than swine, including humans. Sequences encoding such antigenic epitopes are known in the art or are provided herein. For example, a second North American PRRS virus envelope protein, encoded by North American PRRS ORF 5 described herein, can be inserted into a DNA sequence encoding an RNA molecule encoding a North American PRRS virus of the present invention to generate a genetically modified North American PRRS virus comprising an additional envelope protein as a heterologous antigenic epitope. Such a genetically modified North American PRRS virus can be used to induce a more effective immunoprotective response against PRRS viruses in a porcine animal vaccinated therewith.

Examples of an antigenic epitope from a swine pathogen other than a North American PRRS virus include, but are not limited to, an antigenic epitope from a swine pathogen selected from the group consisting of European PRRS, porcine parvovirus, porcine circovirus, a porcine rotavirus, swine influenza, pseudorabies virus, transmissible gastroenteritis virus, porcine respiratory coronavirus, classical swine fever virus, African swine fever virus, encephalomyocarditis virus, porcine paramyxovirus, *Actinobacillus pleuropneumoni, Bacillus anthraci, Bordetella bronchiseptica, Clostridium haemolyticum, Clostridium perfringens, Clostridium tetani, Escherichia coli, Erysipelothrix rhusiopathiae, Haemophilus parasuis, Leptospira* spp., *Mycoplasma hyopneumoniae, Mycoplasma hyorhinis, Pasteurella haemolytica, Pasteurella multocida, Salmonella choleraesuis, Salmonella typhimurium, Streptococcus Streptococcus equismilis*, and *Streptococcus suis*. Nucleotide sequences encoding antigenic epitopes from the aforementioned swine pathogens are known in the art and can be obtained from public gene databases such as GenBank (http://www.ncbi.nlm.nih.gov/Web/Genbank/index.html) provided by NCBI.

If the heterologous antigenic epitopes are antigenic epitopes from one or more other swine pathogens, then the isolated polynucleotide molecule can further contain one or more mutations that genetically disable the encoded PRRS virus in its ability to produce PRRS. Such isolated polynucleotide molecules and the viruses they encode are useful for preparing vaccines for protecting swine against the swine pathogen or pathogens from which the heterologous antigenic epitopes are derived.

The present invention provides a genetically modified North American PRRS virus able to elicit an effective immunoprotective response against infection by a PRRS virus in a porcine animal. Such isolated polynucleotide molecules and the viruses they encode are useful for preparing dual-function vaccines for protecting swine against infection by both a North American PRRS virus and the swine pathogen or pathogens from which the heterologous antigenic epitopes are derived.

The isolated polynucleotide molecules of the present invention comprising nucleotide sequences encoding heterologous antigenic epitopes can be prepared as described above based on the sequence encoding a North American PRRS virus described herein using known techniques in molecular biology.

Figure 4:
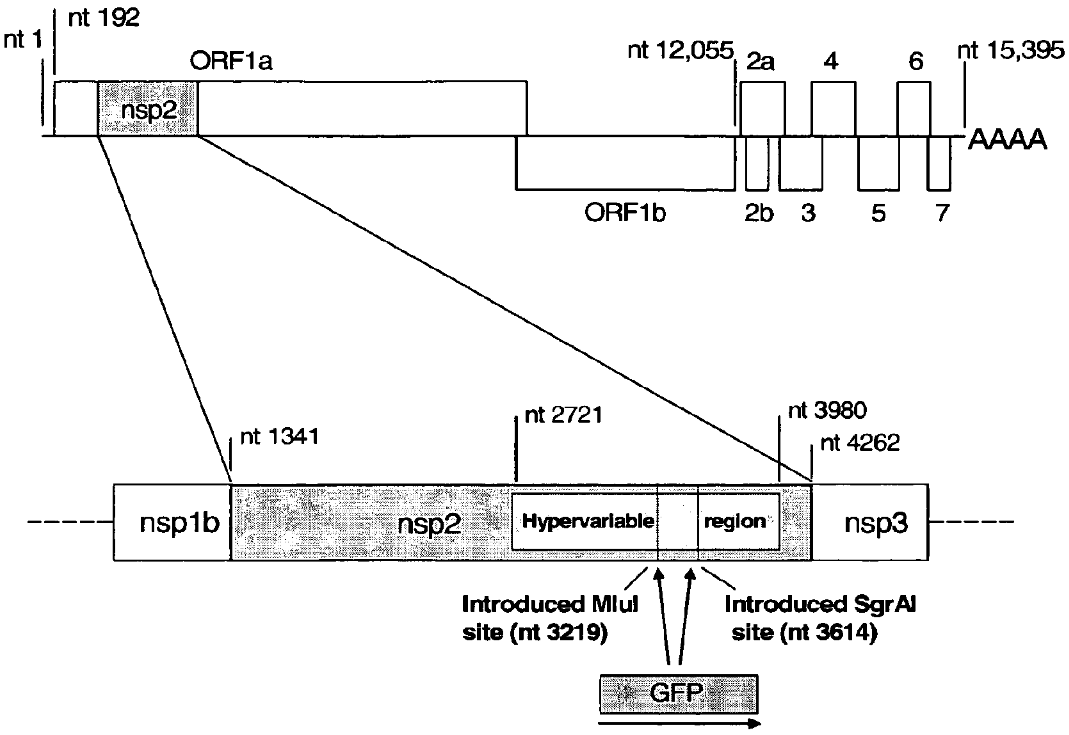
FIG. 4: Genome organization of PRRSV virus. Location or range of various deletions and insertion sites, including: ORF 1a and 1b, Nsp2, the hypervariable region of Nsp2, the deleted region within Nsp2 encoding amino acids 628-759, and the MluI and SgrA1 sites at genome positions 3219 and 3614, between which GFP or the 9 amino acid HA tag were inserted. The active site residues of the cysteine protease domain (Cys437 and His507) and the hypervariable region are indicated. The hypervariable region of nsp2 corresponds approximately to genome coordinates 2720-3980 in P129.

In one embodiment, the additional nucleotide sequences that each encode a heterologous antigenic epitope are inserted into the DNA sequence encoding an infectious RNA molecule encoding a North American PRRS virus within an open reading frame encoding for a PRRS virus protein. In a non-limiting embodiment, the additional nucleotide sequences are inserted in ORF 1a or ORF 1b. In another embodiment, the additional nucleotide sequences are inserted within sequences encoding for the nonstructural protein 2 (nsp2), which is part of ORF 1a. In a separate embodiment, the additional nucleotide sequences are inserted within the region encoding the hypervariable C-terminal portion of nsp2. In a further embodiment, the additional nucleotide sequences are inserted between the DNA sequence encoding amino acids 628 and 759 in the hypervariable region in the nonstructural protein 2 coding region of ORF1a within said DNA sequence, which is within the region encoding the hypervariable C-terminal portion of nsp2. See FIG. 4.

The hypervariable region of nsp2 corresponds approximately to genome coordinates 2720-3980 in P129. See FIG. 4.

In a separate embodiment, the additional nucleotide sequences that each encode a heterologous antigenic epitope are inserted into the DNA sequence encoding an infectious RNA molecule encoding a North American PRRS virus within the sequences encoding any of ORFs 1a, 1b, 2, 3, 4, 5, 6, or 7. See FIG. 4.

In another embodiment, a heterologous antigenic epitope of the genetically modified North American PRRS virus of the present invention is a detectable antigenic epitope. Such isolated polynucleotide molecules and the North American PRRS viruses they encode are useful, inter alia, for studying PRRS infections in swine, determining successfully vaccinated swine, and/or for distinguishing vaccinated swine from swine infected by a wild-type PRRS virus. Preferably, such isolated polynucleotide molecules further contain one or more mutations that genetically disable the encoded PRRS virus in its ability to produce PRRS, and more preferably are able to elicit an effective immunoprotective response in a porcine animal against infection by a PRRS virus.

Heterologous antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Wiley & Sons, Inc., which is hereby incorporated by reference in its entirety. Alternatively, the heterologous antigenic epitope itself can be detected by, for example, contacting samples that potentially comprise the antigenic epitope with fluorescently-labeled antibodies or radioactively-labeled antibodies that specifically bind to the antigenic epitopes.

The present invention further provides an isolated polynucleotide molecule comprising a DNA sequence encoding an infectious RNA molecule which encodes a genetically modified North American PRRS virus that detectably lacks a North American PRRS virus antigenic epitope, wherein the DNA sequence encoding the RNA molecule encoding the North American PRRS virus is SEQ ID NO:1 or a sequence homologous thereto, except that it lacks one or more nucleotide sequences encoding a detectable North American PRRS virus antigenic epitope. Such isolated polynucleotide molecules are useful for distinguishing between swine infected with a recombinant North American PRRS virus of the present invention and swine infected with a wild-type PRRS virus. For example, animals vaccinated with killed, live or attenuated North American PRRS virus encoded by such an isolated polynucleotide molecule can be distinguished from animals infected with wild-type PRRS based on the absence of antibodies specific to the missing antigenic epitope, or based on the absence of the antigenic epitope itself: If antibodies specific to the missing antigenic epitope, or if the antigenic epitope itself, are detected in the animal, then the animal was exposed to and infected by a wild-type PRRS virus. Means for detecting antigenic epitopes and antibodies specific thereto are known in the art, as discussed above. Preferably, such an isolated polynucleotide molecule further contains one or more mutations that genetically disable the encoded PRRS virus in its ability to produce PRRS. More preferably, the encoded virus remains able to elicit an effective immunoprotective response against infection by a PRRS virus.

B. Vaccines and Uses Thereof.

The present invention also provides vaccines comprising North American PRRS viruses, including genetically modified North American PRRS viruses disabled in their ability to produce PRRS in a swine animal as described herein; infectious RNA molecules and plasmids encoding such North American PRRS viruses as described herein; and viral vectors encoding such North American PRRS viruses and isolated RNA molecules as described herein.

In one embodiment, the subject invention provides a vaccine comprising a genetically modified North American PRRS virus which lacks at least one detectable antigenic epitope as described herein, an infectious RNA molecule encoding such a genetically modified North American PRRS virus, a plasmid as described herein encoding such a genetically modified North American PRRS virus, or a viral vector encoding such a genetically modified North American PRRS virus, and a carrier acceptable for pharmaceutical or veterinary use, in an amount effective to elicit an immunoprotective response against PRRS virus infection in the porcine animal.

In another embodiment, the subject invention provides a vaccine comprising a genetically modified North American PRRS virus comprising one or more detectable heterologous antigenic epitopes as described herein, an infectious RNA molecule encoding such a genetically modified North American PRRS virus, a plasmid as described herein encoding such a genetically modified North American PRRS virus, or a viral vector encoding such a genetically modified North American PRRS virus, and a carrier acceptable for pharmaceutical or veterinary use.

Such vaccines can be used to protect from infection a mammal or a bird capable of being pathogenically infected by the pathogen or pathogens from which the detectable heterologous antigenic epitope(s) are derived. If such a vaccine comprises the genetically modified North American PRRS virus, the genetic modification of the North American PRRS virus preferably renders the virus unable to cause PRRS in swine. Thus, such would provide a dual-vaccine for swine, protecting swine from infection by the swine pathogen or pathogens from which the heterologous antigenic epitope(s) are derived as well as from infection by a PRRS virus. If the vaccine comprises an infectious RNA molecule or a plasmid encoding a genetically-modified North American PRRS virus comprising one or more heterologous antigenic epitopes from another swine pathogen, then the sequence encoding the infectious RNA molecule encoding the genetically modified PRRS virus preferably comprises one or more further mutations that genetically disable the encoded North American PRRS virus so that it is unable to cause PRRS. In another preferred embodiment, the encoded genetically modified, disabled North American PRRS virus is able to elicit an immunoprotective response against a PRRS infection in a swine animal, thus providing a dual-vaccine for swine, able to protect swine from infection by the swine pathogen or pathogens from which the heterologous antigenic epitope(s) are derived as well as from infection by a PRRS virus. All of these vaccines also further comprise a carrier acceptable for veterinary use.

Vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's *Pharmaceutical Science,* 18th ed., 1990, Mack Publishing, which is incorporated herein by reference.

Vaccines of the present invention may further comprise one or more additional immunomodulatory components such as, e.g., an adjuvant or cytokine, among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 μg/ml Quil A, 100 μg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 μg/ml Quil A, and 50 μg/ml cholesterol. Other immunomodulatory agents that can be included in the vaccine include, e.g., one or more interleukins, interferons, or other known cytokines.

Vaccines of the present invention can optionally be formulated for sustained release of the virus, infectious RNA molecule, plasmid, or viral vector of the present invention. Examples of such sustained release formulations include virus, infectious RNA molecule, plasmid, or viral vector in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279-292, which is incorporated herein by reference. Additional guidance in selecting and using polymers in pharmaceutical formulations can be found in texts known in the art, for example M. Chasin and R. Langer (eds), 1990, "Biodegradable Polymers as Drug Delivery Systems" in:

*Drugs and the Pharmaceutical Sciences*, Vol. 45, M. Dekker, NY, which is also incorporated herein by reference. Alternatively, or additionally, the virus, plasmid, or viral vector can be microencapsulated to improve administration and efficacy. Methods for microencapsulating antigens are well-known in the art, and include techniques described, e.g., in described, e.g., in U.S. Pat. No. 3,137,631; U.S. Pat. No. 3,959,457; U.S. Pat. No. 4,205,060; U.S. Pat. No. 4,606,940; U.S. Pat. No. 4,744,933; U.S. Pat. No. 5,132,117; and International Patent Publication WO 95/28227, all of which are incorporated herein by reference.

Liposomes can also be used to provide for the sustained release of virus, plasmid, or viral vector. Details concerning how to make and use liposomal formulations can be found in, among other places, U.S. Pat. No. 4,016,100; U.S. Pat. No. 4,452,747; U.S. Pat. No. 4,921,706; U.S. Pat. No. 4,927,637; U.S. Pat. No. 4,944,948; U.S. Pat. No. 5,008,050; and U.S. Pat. No. 5,009,956, all of which are incorporated herein by reference.

An effective amount of any of the above-described vaccines can be determined by conventional means, starting with a low dose of virus, plasmid or viral vector, and then increasing the dosage while monitoring the effects. An effective amount may be obtained after a single administration of a vaccine or after multiple administrations of a vaccine. Known factors can be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether an adequate immune response has been achieved is to determine seroconversion and antibody titer in the animal after vaccination. The timing of vaccination and the number of boosters, if any, will preferably be determined by a doctor or veterinarian based on analysis of all relevant factors, some of which are described above.

The effective dose amount of virus, infectious RNA molecule, plasmid, or viral vector, of the present invention can be determined using known techniques, taking into account factors that can be determined by one of ordinary skill in the art such as the weight of the animal to be vaccinated. The dose amount of virus of the present invention in a vaccine of the present invention preferably ranges from about $10^1$ to about $10^9$ pfu (plaque forming units), more preferably from about $10^2$ to about $10^8$ pfu, and most preferably from about $10^3$ to about $10^7$ pfu. The dose amount of a plasmid of the present invention in a vaccine of the present invention preferably ranges from about 0.1 μg to about 100 mg, more preferably from about 1 μg to about 10 mg, even more preferably from about 10 μg to about 1 mg. The dose amount of an infectious RNA molecule of the present invention in a vaccine of the present invention preferably ranges from about 0.1 μg to about 100 mg, more preferably from about 1 μg to about 10 mg, even more preferably from about 10 μg to about 1 mg. The dose amount of a viral vector of the present invention in a vaccine of the present invention preferably ranges from about $10^1$ pfu to about $10^9$ pfu, more preferably from about $10^2$ pfu to about $10^8$ pfu, and even more preferably from about $10^3$ to about $10^7$ pfu. A suitable dosage size ranges from about 0.5 ml to about 10 ml, and more preferably from about 1 ml to about 5 ml.

It is to be understood that the term "North American PRRS viruses of the present invention" and like terms, unless otherwise indicated, include any of the genetically modified North American PRRS viruses described herein as well as the unmodified North American PRRS virus described herein encoded by SEQ ID NO:1 or a sequence homologous thereto.

C. Diagnostic Kits

The present invention also provides diagnostic kits. The kit can be valuable for differentiating between porcine animals naturally infected with a field strain of a PRRS virus and porcine animals vaccinated with any of the vaccines described herein. The kits can also be of value because animals potentially infected with field strains of PRRS virus can be detected prior to the existence in the absence of clinical symptoms and removed from the herd, or kept in isolation away from naïve or vaccinated animals. The kits include reagents for analyzing a sample from a porcine animal for the presence of antibodies to a PRRS virus. Diagnostic kits of the present invention can include as a component a peptide or peptides which comprise all or a portion of a protein sequence which is no longer present in a genetically modified North American PRRS virus which may optionally comprise one or more detectable heterologous antigenic epitopes. Kits of the present invention can alternatively include as a component a peptide which is a fusion protein. The term "fusion peptide" or "fusion protein" for purposes of the present invention means a single polypeptide chain consisting of at least a portion of a PRRS virus protein and a heterologous peptide or protein.

D. Plasmids Encoding a North American PRRS Virus or a Genetically Modified North American PRRS Virus.

The present invention also provides any of the above-described isolated polynucleotide molecules in the form of a plasmid capable of expressing the North American PRRS virus encoded thereby.

Plasmids of the present invention can express the encoded North American PRRS virus outside of a living organism, to produce North American PRRS viruses of the invention useful, inter alia, for preparing vaccines. In one embodiment, a plasmid of the present invention capable of expressing a North American PRRS virus outside of a living organism is a plasmid wherein transcription of viral RNA therefrom occurs in vitro (i.e. extracellularly); the resulting viral RNA molecule is transfected into a suitable host cell using known mechanisms of transfection, such as electroporation, lipofection (in some cases using a commercially available reagent, such as Lipofectin™ (Life Technologies Inc., Rockville, Md., USA)), or DEAF dextran mediated transfection. Other methods of transfection are known in the art and can be employed in the present invention. An example of such a plasmid for in vitro transcription of North American PRRS viral RNA is the plasmid pT7P129A (ATCC Accession No. 203488). Any promoter useful for in vitro transcription can be used in such plasmids of this invention. T7 is one such promoter, but other promoters can be used, such as an SP6 promoter or a T3 promoter. The sequences of such promoters can be artificially synthesized or cloned from commercially available plasmids. Suitable plasmids for preparing such plasmids capable of expressing North American PRRS virus include, but are not limited to, general purpose cloning vector plasmids such as pCR2.1 (Invitrogen, Carlsbad, Calif., USA), pBR322, and pUC18. A nucleotide sequence of the present invention encoding the North American PRRS virus can be inserted into any of these plasmids using known recombinant techniques. Other plasmids into which the polynucleotide molecules of the present invention can be inserted will be recognized by those of ordinary skill in present invention can be inserted will be recognized by those of ordinary skill in the art.

Suitable conditions for in vitro transcription of viral RNA from any of the above-described recombinant plasmids comprising a DNA sequence encoding an infectious RNA molecule encoding a North American PRRS virus depends on the type of plasmid, for example, its particular promoter, and can be ascertained by one of ordinary skill in the art. For example, if a plasmid of the present invention is based on a pCR2.1 plasmid comprising a T7 promoter, then an example of suitable conditions for in vitro transcription includes reacting the plasmid with T7 RNA polymerase and ribonucleotides in a standard buffer and incubating the reaction at 37° C. for about 30 minutes. In some cases, commercial kits are available for transcribing RNA from a particular plasmid, and such kits can be used in the present invention. The reaction mixture following transcription can be directly transfected into a suitable host cell without purification, or the transcribed North American PRRS virus RNA can be purified by known RNA purification techniques, for example by organic (e.g. phenol) extraction and alcohol (e.g. ethanol or isopropanol) precipitation, prior to transfection.

Transcription of the DNA sequence encoding an infectious RNA molecule encoding a North American PRRS virus, and further comprising one or more additional nucleotide sequences that each encode a heterologous antigenic epitope, results in the formation of a genomic and subgenomic RNA molecules. In one embodiment, at least one heterologous antigenic epitope is translated directly from the genomic RNA molecule. In another embodiment, at least one heterologous antigenic epitope is translated from a subgenomic RNA molecule that is synthesized from the genomic RNA.

The term "translation" for purposes of the present invention means the synthesis of protein from nucleotides such as an RNA molecule. In one embodiment, translation of the genomic or a subgenomic RNA molecule encoding a heterologous antigenic epitope results in synthesis of a peptide or protein consisting of the heterologous antigenic epitope itself. In another embodiment, translation of the genomic or a subgenomic RNA molecule results in synthesis of a fusion peptide or protein. The term "fusion peptide or protein" for purposes of the present invention means a single polypeptide chain consisting of at least a portion of a PRRS virus protein and at least one heterologous antigenic epitope.

Practically any mammalian or avian cell culture can be transfected with the North American PRRS virus RNA obtained as described above in order to generate a first round of North American PRRS virions. An example of cells which one might find particularly useful because of their ready availability and ease of use are BHK (baby hamster kidney) cells. However, if one wishes to generate a cell culture capable of sustained production of North American PRRS virions, then porcine alveolar macrophage cells or MARC-145 cells (Kim, H. S., et al., supra) are preferred since these cells excrete high levels of new generation PRRS virions subsequent to PRRS virus infection. Other cell lines derived from the MA-104 cell line may also be used for sustained generation of North American PRRS virions of the present invention. Primary porcine alveolar macrophage cells can be obtained by lung lavages from pigs, and the MARC-145 monkey kidney cell line can be obtained from the National Veterinary Services National Veterinary Services Laboratories otherwise known as NVSL (Ames, Iowa, USA).

In another embodiment, a plasmid capable of expressing a North American PRRS virus of the present invention outside of a living organism is a plasmid which is transfected into a suitable host cell, for example by electroporation or lipofection, transcription of the infectious RNA molecule and expression of the North American PRRS virus therefrom occurring within the transfected host cell. The transfected host cell therefore generates North American PRRS virions. Such a completely cellular method has heretofore never been disclosed or suggested for any virus within the order of Nidovirales. Because of possible cryptic splicing and termination sequences present in the RNA genome of viruses of the Nidovirales order, a completely cellular method of expressing a Nidovirales virus was believed unlikely. Cryptic sequences include RNA splice donor and splice acceptor sequences, which could cause inappropriate splicing of the RNA transcript, as well as polyadenylation sequences, which could cause premature termination by the cellular RNA polymerase II. The present invention demonstrates, however, that the presence of such sequences in a plasmid comprising a cDNA clone of a Nidovirus does not prevent the plasmid's ability to express the Nidovirus when the plasmid is directly transfected into a suitable host cell.

Accordingly, the subject invention also provides plasmids and a completely cellular method for expressing a Nidovirales virus, wherein the plasmid comprises: a) a DNA sequence encoding an infectious RNA molecule encoding the Nidovirales virus; and b) a promoter capable of transcribing said encoding sequence in a cell, wherein said promoter is in operative association with the DNA sequence encoding the infectious RNA molecule. The method comprises transfecting a suitable host cell with such a plasmid, subjecting the transfected host cell to conditions suitable for expression of gene sequences transfected therein, and collecting the expressed Nidovirales virus therefrom. An example of a plasmid suitable for completely cellular expression of North American PRRS virus outside of a living organism is the plasmid pCMV-S-P129 (ATCC Accession No. 203489). In a preferred embodiment, the promoter of such a plasmid is a CMV promoter. In a preferred embodiment, a plasmid of the invention suitable for a completely cellular method of expressing a Nidovirales virus comprises a eukaryotic promoter, such as a CMV promoter, immediately upstream and adjacent to the nucleotide sequence encoding the Nidovirales virus. In a preferred embodiment, the nucleotide sequence encoding the Nidovirales virus encodes a PRRS virus, either European or North American. Other examples of Nidovirales viruses that can be expressed by means of the above-described completely cellular method include other Arteriviruses such as, equine arteritis virus, lactate dehydrogenase-elevating virus, and simian haemorrhagic fever virus; viruses that are members of the genus *Coronaviridae*, such as, but not limited to, feline infectious peritinitis virus, feline enteric coronavirus, canine coronavirus, bovine coronavirus, porcine respiratory coronavirus, turkey coronavirus, porcine transmissible gastroenteritis virus, human coronavirus, murine hepatitis virus, and avian infectious bronchitis virus; and members of the genus *Toroviridae*, such as, but not limited to, Berne virus, Breda virus, and human torovirus. Thus, plasmids suitable for completely cellular expression comprising a nucleotide sequence encoding one of these viruses comprising a nucleotide sequence encoding one of these viruses are also encompassed by the present invention.

Suitable plasmids that can be used to prepare recombinant plasmids of the present invention for completely cellular expression outside of a living organism of a Nidovirales virus, such as a PRRS virus, include virtually any plasmid useful for transfection and expression in eukaryotic cells. An examples of a plasmid suitable for preparing recombinant plasmids of the present invention for completely cellular expression of a Nidovirales virus is the plasmid pCMVbeta (Clontech, Palo Alto, Calif., USA). Other plasmids which are able to transfect and express genes in eukaryotic cells which can be used to prepare plasmids of the present invention include, but are not limited to, pcDNA3.1, pRc/RSV, and pZeoSV2 (all from Invitrogen); and pCMV-Sport3 and pSV-Sport1 (both from Life Technologies Inc.). However, almost any eukaryotic expression vector will work for the present invention. Constructs based on cosmids can also be used for completely cellular ex vivo expression of a Nidovirales virus.

Suitable host cells for the completely cellular method of the present invention for expressing PRRS virus include porcine alveolar macrophage cells and the MARC-145 cells, described above. Methods of transfecting these cells with a plasmid are basically the same as those methods for transfecting cells with viral RNA described above. Such methods include, but are not limited to, electroporation, lipofection, DEAE dextran mediated transfection, and calcium phosphate coprecipitation.

Once host cells, such as porcine alveolar macrophage cells or a MARC-145 cells, have been transfected according to the subject invention, either with viral RNA or with a plasmid comprising a nucleotide sequence encoding a virus, then the cells can be frozen at about −80° C. or below for storage for up to several years. For longer periods of time, i.e. decades, storage in liquid nitrogen is preferred. If relatively frequent use of the encoded virus is envisioned, then cells hosting the virus can also be maintained (unfrozen) in culture using known techniques, for shorter periods of time. Moreover, viral particles excreted by such cells can be stored frozen at about −80° C. or below as a source of virus. Transfection of such cell lines with the polynucleotide molecule encoding the virus can be confirmed if desired, for example, by testing exhausted medium excreted by the cell line for a PRRS virus antigen using an immunofluorescent antibody test. Antibodies which are specific for PRRS virus antigens are known in the art (see, e.g., Collins, E. J., et al., WO 93/03760 Mar. 4, 1993).

In another embodiment, a plasmid of the present invention comprising a nucleotide sequence encoding a North American PRRS virus is suitable for in vivo expression of the North American PRRS virus, i.e. expression in a living organism. Plasmids which can be used for preparing recombinant plasmids for in vivo expression of a North American PRRS virus include, but are not limited to the plasmids capable of transfecting eukaryotic cells described above, such as pCMVbeta.

Animals that can be transfected with plasmids of the present invention include mammals and birds. If the animal is other than a porcine animal, for example, a mallard duck, then the plasmid can comprise a nucleotide sequence encoding a North American PRRS virus comprising further antigenic epitopes from pathogens which are capable of pathogenically infecting the animal; in such a case, the plasmid will encode a North American PRRS virus serving as a vector for transporting epitopes into the animal. If the animal is a porcine animal, then the plasmid can usefully encode any of the North American PRRS viruses described herein, including the genetically-modified North American PRRS viruses described herein.

E. Viral Vectors Encoding a North American PRRS Virus, Including Viral Vectors Encoding Genetically Modified North American PRRS Viruses:

The present invention also provides viral vectors comprising a DNA sequence encoding an infectious RNA molecule encoding any of the North American PRRS viruses described herein, including the genetically-modified North American PRRS viruses described herein. Such viral vectors are useful for transfecting eukaryotic cells for production of PRRS viruses of the present invention outside of a living organism, or for transfecting swine, or other mammals, or avians, with the sequence encoding the North American PRRS virus, for in vivo expression of the North American PRRS virus therein.

Some examples of viruses that can be used as vectors for preparing the viral vectors of the present invention include, but are not limited to, swine viruses such as, but not limited to, swine pox virus, pseudorabies virus, or African swine fever virus. Such swine viruses can be obtained from The National Veterinary Services Laboratories (Ames, Iowa, USA) of the United States Department of Agriculture; the American Type Culture Collection, otherwise known as the ATCC (Manassas, Va., USA); and other known sources. Recombinant viral vectors based on suitable swine viruses such as the aforementioned swine viruses are useful for transfecting swine animals with a nucleotide sequence encoding a North American PRRS virus of the present invention.

Viral vectors comprising a DNA sequence encoding an infectious RNA molecule encoding a North American PRRS virus of the present invention based on these and other viruses can be prepared using known recombinant techniques described in texts such as those cited previously in this application.

F. Transfected Host Cells Encoding or a Genetically Modified North American PRRS Viruses.

The present invention also provides transfected host cells that comprise a DNA sequence encoding an infectious RNA molecule encoding any of the North American PRRS viruses described herein, including the genetically-modified North American PRRS viruses described herein, which transfected host cells are capable of expressing the North American PRRS virus. Such transfected host cells are useful for producing North American PRRS viruses of the present invention. Examples of transfected host cells of the present invention include the transfected porcine alveolar macrophage cells and the transfected MARC-145 cells described above.

Other transfected host cells of the invention include, but are not limited to, transfected MA-104 cells and other derivatives of MA-104 cells that are transfected; transfected Baby Hamster Kidney (BHK) cells; transfected Chinese Hamster Ovary (CHO) cells; and African Green Monkey kidney cells other than MA-104 cells or MARC-145 cells, such as VERO cells; that are transfected.

G. North American PRRS Viruses, Including Genetically Modified North American PRRS Viruses:

The present invention also provides North American PRRS viruses as described herein, including genetically-modified North American PRRS viruses as described herein, expressed and/or encoded by any of the above-described isolated polynucleotide molecules, RNA molecules, plasmids, viral vectors, or transfected host cells.

In certain situations, for example where the North American PRRS virus is to be used in a vaccine for swine and the North American PRRS virus has not been genetically modified as described above so as to be unable to cause PRRS, it is desirable to treat the North American PRRS virus, for example by inactivating or attenuating it, so that it is unable to cause PRRS in swine to which it is administered. Known methods can be used to inactivate a North American PRRS virus of the present invention so that it is unable to cause PRRS in an animal. Examples of such methods include, but are not limited to, treatment with formaldehyde, BEI (binary ethyleneimine), or BPL (beta-propiolactone). Methods of attenuation are also known in the art, and such methods can be used to attenuate a North American PRRS virus of the present invention. A North American PRRS virus of the present invention can, for example, be attenuated by serial passage in cell culture.

If a North American PRRS virus of the present invention is for use in an animal other than a porcine animal, or if it has been genetically modified as described herein so that it is unable to produce PRRS in a porcine animal, then it is not necessary to treat the virus as described in the preceding paragraph prior to using it in a vaccine.

The following examples are provided to merely illustrate aspects of the subject invention. They are not intended, and should not be construed, to limit the invention set forth in the claims and more fully described herein.

EXAMPLES

Example I

Preparation of an Infectious cDNA Clone of a North American PRRS Virus Isolate Source of PRRS virus and MARC-145 cells: A North American PRRS virus isolate designated P129 was obtained from Drs. Gregory W. Stevenson, William G. Van Alstine, and Charles L. Kanitz of Purdue University's Animal Disease Diagnostic Laboratory in West Lafayette, Ind. The P129 virus was originally isolated in the autumn of 1995 from a swine herd in southern Indiana experiencing a severe PRRS outbreak. This farm had no previous history of PRRS problems or PRRS vaccination. The P129 isolate was more virulent than several other field isolates from the same time period and geographic area, in that it produced more severe and more consistent respiratory disease in young pigs. The virus was initially isolated on primary porcine alveolar macrophage (the natural host cell), and subsequently passaged on MARC-145 cells (Kim et al., 1993). Genes encoding structural proteins of P129 were found to be homologous to corresponding known North American PRRS gene sequences.

The MARC-145 cell line that was used to propagate PRRS viruses is a clone of the MA-104 Rhesus Macaque Monkey Kidney cell line. The MARC-145 cells were obtained from the National Veterinary Services Laboratories (NVSL, Ames, Iowa) of the USDA. These cells have been tested and found negative for mycoplasmas and for common porcine extraneous agents. MARC-145 cells are routinely grown at 37 C in OptiMEM (Life Technologies Inc.) with 2% fetal bovine serum and antibiotics.

Five biological clones were plaque purified from the P129 virus stock, and these were designated P129A through P129E. Plaque purification was carried out by infecting monolayers of MARC-145 cells with P129 virus, adding an overlay of OptiMEM containing 1.25% SeaPlaque agarose (FMC BioProducts), 2% fetal bovine serum, and antibiotics. Plaques were clearly visible following incubation for 7 days, when 5 well-isolated plaques were picked and passaged onto fresh MARC-145 monolayers. When cytopathic effect (virus induced cell death) became apparent the progeny virus from each of these cultures was subjected to another round of plaque purification. One well-isolated plaque from each of the five clones was picked and expanded to produce large stocks. The 5 clones were tested for virulence in young pigs, either individually (clones A and E) or in combination (clones B-D, or clones A-E). In all cases, the plaque purified virus replicated well in pigs and caused clinical disease. The severity of clinical symptoms was less than that caused by the uncloned P129 virus, even when all five clones were used together. P129A was chosen for sequencing, and was used in subsequent molecular manipulations.

Determination of the Genome Sequence of P129A:

Plaque purified virus P129A was used for sequence determination after 10 serial passages from the pig (including two plaque purifications and one subsequent passage). SEQ ID NO:1 shows the cDNA sequence corresponding to the P129A RNA genome. The genome is 15,395 nucleotides in length (excluding the polyadenosine tail), begins with ATGACGTA, and ends with CCGCAATT. A typical polyadenosine tail of 55 residues is also provided in SEQ ID NO:1.

For the structural genes of P129A (ORFs 2 through 7), which comprise the 3' 20% of the genome, various PCR primers were chosen based on several partial cDNA sequences of other North American PRRS virus isolates available in the public DNA sequence database GenBank (for example PRU00153). Purified viral RNA was reverse transcribed into cDNA using reverse transcriptase and random hexamer primers. This cDNA was then used in PCR with gene-specific primers. PCR products were excised from gels and T/A cloned into plasmid pCR2.1 (Invitrogen). For each primer pair, multiple plasmids (from independent PCR reactions) were DNA sequenced. Sequences were assembled using the Seqman program from the Lasergene package (DNASTAR, Inc). This permitted completing the sequence of positions 11,992 through 15,347 of the P129A genome.

Also in the GenBank database are a series of short sequences (approximately 218 nucleotides total) which comprise a portion of the ORF 1b gene of several isolates of PRRS virus. One of these (PPSSEQB) was used to design PCR primers (forward 5'-ACAGTTTGGTGATCTATG-3' (SEQ ID NO:10), corresponding to positions 9063-9080; reverse 5'-CAGATTCAGATGTTCAA-3' (SEQ ID NO:11), corresponding to positions 9252-9268). These amplified a 206 nucleotide fragments, which includes 171 nucleotides of new sequence from the P129A ORF1b gene, corresponds to positions 9081 to 9251. A new forward primer was designed within this region (5'-ACCTCGTGCTGTATGCCGAATCTC-3' (SEQ ID NO:12), positions 9201-9224), and a matching primer was designed within ORF1b immediately upstream of ORF2 (5'-TCAGGCCTAAAGTTGGTTCAATGA-3' (SEQ ID NO:13), positions 12,027-12,050). These primers were used in RT-PCR to amplify a 2850 nucleotide fragment of ORF1b, corresponding to positions 9201-12,050 of the P129A genome.

During RT-PCR amplification of ORF5 of another North American field isolate of PRRS virus, a minor band was seen which was smaller than the expected size. This was sequenced and found to have limited homology with ORF1a of Lelystad virus (resulting from false priming). New primers within this region were chosen to amplify P129A (forward 5'-GATGACTGGGCTACTGACGAGGAT-3' (SEQ ID NO:14), corresponding to positions 1587-1610; reverse 5'-AGAGCGGCTGGGATGACACTG-3' (SEQ ID NO:15), corresponding to positions 1877-1897). In addition to the product of 311 nucleotides (266 nucleotides of new P129A sequence between the primers corresponding to positions 1611-1876), a larger minor PCR product of 701 nucleotides was cloned and sequenced (656 nucleotides of new P129A sequence between the primers corresponding to positions 1611-2264). The larger band results from false priming of the reverse primer at positions 2265-2269.

The extreme 5' end of the genome of P129A was determined by 5' RACE (rapid amplification of cDNA ends) using a commercially available kit (Life Technologies Inc). Two nested reverse primers were chosen from within the known ORF1a sequence ("RACE2" 5'-CCGGGGAAGCCAGACGATTGAA-3' (SEQ ID NO:16), positions 1917-1938; and "RACE3" 5'-AGGGGGAGCAAAGAAGGGGTCATC-3' (SEQ ID NO:17), positions 1733-1756). RACE2 was used to prime cDNA synthesis, while RACE3 was used in PCR. The resulting PCR products were cloned and sequenced. The two longest products ended at precisely the same base (position 1 in SEQ ID NO:1).

The large gap between known sequence in ORF1a and ORF1b was bridged using long RT-PCR. Two new primers were used (forward 5'-AGCACGCTCTGGTGCAACTG-3' (SEQ ID NO:18), positions 1361-1380; reverse 5'-GC-CGCGGCGTAGTATTCAG-3' (SEQ ID NO:19), positions 9420-9438). The resulting 8078 nucleotide RT-PCR product was cloned and sequenced.

The extreme 3' end of the genome of P129A was determined by ligating the 3' and 5' ends of the viral RNA together and using RT-PCR to amplify the junction fragment. The resulting junction fragments were cloned and sequenced. Briefly, RNA extracted from pelleted virions was treated with tobacco acid pyrophosphatase (to remove 5' cap structures), then self-ligated then self-ligated with T4 RNA ligase (both from Epicentre Technologies). The primers used were 5'-CGCGTCACAGCATCACCCTCAG-3' (SEQ ID NO:20) (forward, positions 15,218-15,239) and either 5'-CGGTAG-GTTGGTTAACACATGAGTT-3' (SEQ ID NO:21) (reverse, positions 656-680) or 5'-TGGCTCTTCGGGC-CTATAAAATA-3'(SEQ ID NO:22) (reverse, positions 337-359). All of the resulting clones were truncated at the 5' end of the genome (the most complete came to within 57 nucleotides of the actual 5' end, as revealed by 5' RACE), however two of these clones contained the complete 3' end of the genome including the polyadenosine tail (42 and 55 adenosine residues in length). This completed the sequencing of the cDNA 15,450 base genome of PRRS isolate P129A, including polyA tail, as shown in SEQ ID NO:1.

Creation of an Infectious Full-Length cDNA Clone of P129A:

A full-length infectious cDNA clone of P129A, designated pT7P129A, was assembled from four overlapping cloned RT-PCR products. The four RT-PCR products were first T/A cloned into plasmid pCR2.1 (Invitrogen) and transfected into *Escherichia coli* strain DH5-alpha. Bacterial colonies were screened, and those which contained inserts of the expected sizes in the "T7 to M13" orientation were chosen for sequencing and further manipulation. All four cloned RT-PCR products contained one or more non-silent mutations (deviations from the consensus nucleotide sequence for P129A of SEQ ID NO:1 which would result in a change in amino acid sequence of the encoded ORFs). These non-silent mutations (save one at position 12,622 in ORF 2) were repaired by subcloning fragments from other cloned RT-PCR products. The four repaired subgenomic clones were assembled into a full-length clone in a stepwise manner, using available restriction sites (see FIG. 1). The 5' and 3' ends of the cDNA corresponding to the P129A genome in pT7P129A were modified by the addition of a T7 promoter and appropriate restriction endonuclease sites. The construction of pT7P129A is described in further detail in the following paragraphs:

The 5' end of the genome (positions 1-1756), generated by 5'-RACE and cloned into pCR2.1 as described above, was modified to include a T7 promoter immediately upstream of the cDNA corresponding to the P129A genome and a PacI site for future cloning. A 3-way ligation was performed using the 1216 bp DsaI-BseRI fragment of this plasmid (containing bases 27-1242 of P129A), the 4407 bp BseRI-XbaI fragment of the same plasmid (containing bases 1243-1756 of P129A and the entire plasmid vector up to the XbaI site), and the following synthetic double-stranded adapter (SEQ ID NO: 23, first below and SEQ ID NO: 24, second below):

```
5'-CTAGATTAATTAATACGACTCACTATAGGGATGACGTATAGGTGTTGGCTCTATGC-3'

3'-TAATTAATTATGCTGAGTGATATCCCTACTGCATATCCACAACCGAGATACGGTGC-5'
XbaI             T7 promoter                              DsaI
          PacI                           P129A genome
```

The predicted transcript from the T7 promoter includes a single "G" residue from the promoter immediately upstream of the first "A" of the viral genome. A non-silent mutation at position 1230 (A to G) was repaired by replacing the 906 bp AatII-SacII fragment (bases 740-1645) with the same fragment from another clone. This plasmid was designated "pT7R3A-2".

The 8078 nucleotide PCR product described above was used to cover bases 1361-9438 of the P129A genome. A 58 bp deletion (positions 2535-2592) and 7 non-silent point mutations were corrected by subcloning fragments from other cloned RT-PCR products, yielding plasmid "pGAP10B-4". The 7837 bp Bsu36I-SpeI fragment from this plasmid was ligated to the 5482 bp Bsu36I-SpeI fragment from pT7R3A-2. The resulting plasmid "pT7RG" contains the first 9438 bases of the P129A genome behind the T7 promoter.

The 2850 nucleotide fragment of ORF1b described above (genome positions 9201-12,050) was corrected to repair non-silent mutations and designated "p1B3A-2". The 2682 bp NdeI-SpeI fragment of this plasmid was ligated to the 13,249 bp NdeI-SpeI fragment of pT7RG to yield plasmid "pT71A1B", which contains the first 12,050 bases of the P129A genome.

The fourth and final fragment of the P129A genome was derived by RT-PCR of ORFs 2 through 7, including the 3' non-translated region and a portion of the polyA tail. The forward primer was 5'-ACTCAGTCTAAGTGCTG-GAAAGTTATG-3' (SEQ ID NO:25) (positions 11,504-11,530) and the reverse primer was 5'-GGGATTTAAATATG-CATTTTTTTTTTTTTTT TTTTTTAATTGCGGCCGCATGGTTCTCG-3' (SEQ ID NO:26). The reverse primer contains the last 22 bases of the P129A genome (positions 15,374-15,395), a polyA tail of 21 bases, an NsiI site (ATGCAT) and a SwaI site (ATTTAAAT). Non-silent point mutations and a single base deletion were repaired by subcloning fragments from other clones. An additional non-silent point mutation at position 12,622 (A to G) was inadvertently introduced at this stage. This results in a change from glutamine to arginine near the C-terminus of the ORF2 protein (amino acid residue 189 of the 256 amino acids in ORF2, which does not affect the overlapping ORF 3). This mutation had no apparent influence on viral growth, in cell culture or in pigs, and was not repaired. This mutation served as a genetic marker to distinguish virus derived from the cDNA clone from possible contamination with parental P129A or other PRRS viruses. The plasmid was designated "p2_7D-4". The structural genes of P129A were added to the rest of the genome by ligating the 3678 bp Eco47III-SpeI fragment of p2_7D-4 to the 15,635 bp Eco47III-SpeI fragment of pT71A1B.

This yields the final construct "pT7P129A", which comprises cDNA corresponding almost identically to the entire genome of P129A (however, with only a 21 base polyA tail, as opposed to 55 base polyA tail) behind a T7 promoter, cloned into the pCR2.1 vector between unique restriction enzyme sites (PacI and SwaI). The total length of pTP7129A is 19,313 bp, and it is stable in *E. coli* strain DH5-alpha. pT7P129A contains an A to G non-silent point mutation at position 12,622 that results in an arginine at position 189 of ORF2 rather than a glutamine (as is encoded by SEQ ID NO:1) and a silent C to T mutation at position 1559. Neither of these mutations affected viral growth under the conditions examined, both in cell culture and in pigs culture and in pigs. For example, pT7P129A was used for in vitro transcription and the resulting RNA transcripts produced live North American PRRS virus when transfected into MARC-145 cells, thus demonstrating that this full-length clone is infectious.

In Vitro Transcription and Transfection of RNA Transcripts:

In plasmid pT7P129A there are two T7 promoters in tandem upstream of the viral genome. One of these is positioned immediately upstream of the viral genome and was built into the PCR primer as described above. The other is present in the pCR2.1 cloning vector and is located outside of the multiple cloning site (initiating transcription 44 bases upstream of the viral genome). PacI was used to cut between these T7 promoters prior to in vitro transcription to generate a transcript that is closer to authentic viral RNA (a single extra G immediately upstream the viral genome, as opposed to 44 extra bases from the distal T7 promoter). In addition, pT7P129A was cut with SwaI prior to in vitro transcription. The resulting run-off transcripts include a 21 base long polyA tail and nine non-PRRS nucleotides, including an NsiI site (which was not used to linearize the plasmid, since the site also occurs once in the viral genome). The digested plasmid was purified by phenol extraction and ethanol precipitation prior to use.

A commercial kit (T7 Cap-Scribe, Boehringer Mannheim) was used for in vitro transcription. The DNA pellet from above, containing about 0.6 μg of PacI/SwaI digested pT7P129A, was resuspended in 20 μl of T7 Cap-Scribe buffer/T7 polymerase and incubated at 37° C. for 30 minutes. A portion of the reaction was analyzed by agarose gel electrophoresis and shown to contain full-length RNA transcripts in addition to the expected DNA bands of 15,445 bp and 3868 bp. The in vitro transcription reaction was used fresh, immediately following incubation, without purification. Freshly confluent monolayers of MARC-145 cells were washed once in OptiMEM (without serum), and covered with 1 ml per 35 mm well of OptiMEM (without serum) containing 500 μg/ml DEAE dextran (molecular weight approx. 500,000, Pharmacia Biotech). In vitro transcription reaction (15 μl) was added immediately. After 1 hour at 37° C., the transfection mixture was removed, monolayers were washed once with PBS and overlaid with 1.25% SeaPlaque agarose (FMC corporation) in OptiMEM with 2% fetal bovine serum and antibiotics. After 5 days at 37° C., a single plaque was visible. This virus was designated "rP129A-1" and was expanded on MARC-145 cells and characterized in cell culture and in pigs. Subsequent transfections of in vitro transcribed RNA from pT7P129A, using both DEAE dextran and electroporation, have yielded many additional plaques.

Characterization of Recombinant Virus rP129A-1:

There are no apparent differences in growth kinetics, yield, or plaque morphology between cDNA-derived recombinant virus rP129A-1 and its non-recombinant parent P129A. As discussed above, there are two differences in nucleotide sequence between the coding sequence of pT7P129A and the consensus sequence of P129A (shown in SEQ ID NO:1). Firstly, at position 1559 pT7P129A contains a T, whereas P129A contains a C (this is a silent mutation). Secondly, at position 12,622 pT7P129A contains a G, whereas P129A contains an A (this is the glutamine to arginine change in ORF2 described above). In order to rule out the possibility that rP129A-1 is actually a non-recombinant PRRS virus contaminant, RT-PCR and sequencing were performed on the regions surrounding these performed on the regions surrounding these two differences. In the case of both genetic markers, rP129A-1 was identical to plasmid pT7P129A and different from parental virus P129A, thus confirming that rP129A-1 is derived from the infectious cDNA clone.

Figure 2:
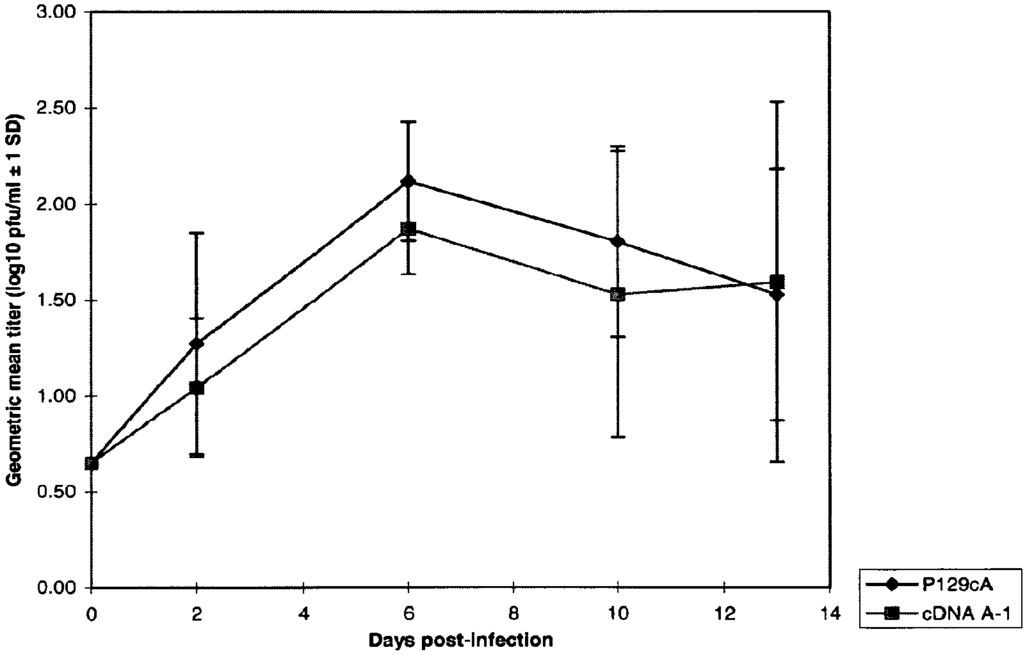
FIG. 2: Serum viremia following infection with P129A or recombinant PRRS virus rP129A-1. Determined by plaque assay on MARC-145 cells. The lower limit of detection is 5 pfu/ml (or 0.7 on the log scale).
Figure 3:
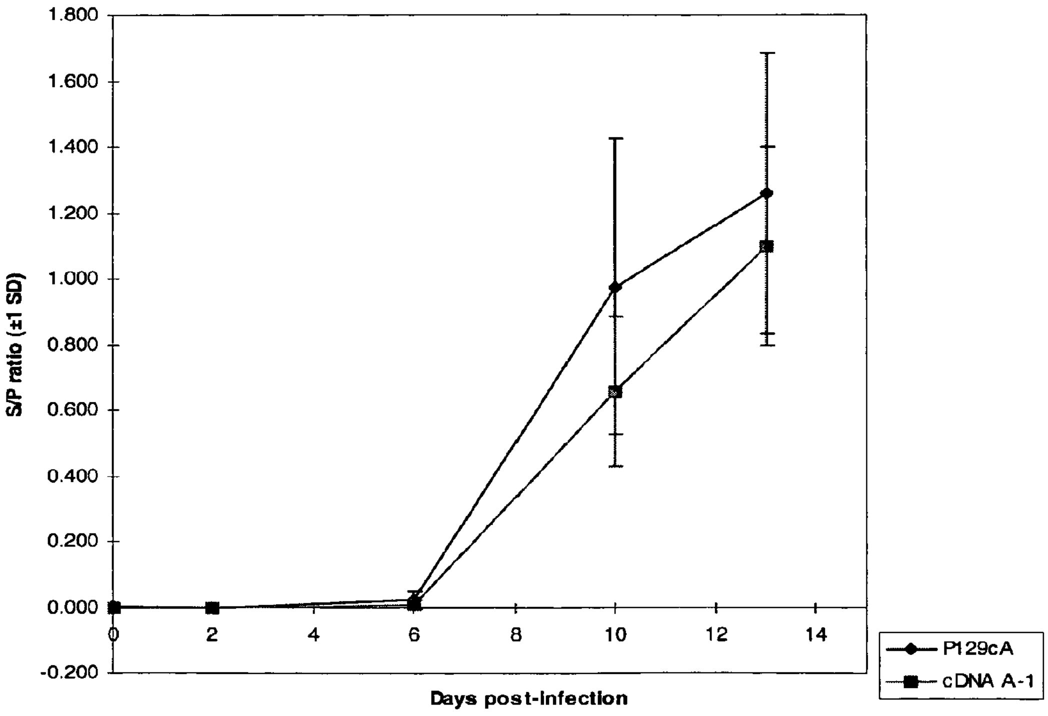
FIG. 3: Anti-PRRS virus serum antibody following infection with P129A or recombinant PRRS virus rP129A-1. Determined by HerdChek PRRS ELISA assay (IDEXX (Westbrook, Me., USA)).

Characterization of Recombinant Virus rP129A-1 in Pigs:

The cDNA-derived virus rP129A-1 was compared to its non-recombinant parent P129A for its ability to infect and cause clinical disease in young pigs. Three groups of 10 pigs each from a PRRS-negative herd were infected at 4 weeks of age with either P129A, rP129A-1, or mock-infected with cell culture medium. Clinical signs, rectal temperatures, and body weights were monitored. Blood was collected on days 0, 2, 6, 10, and 13 post-infection for determination of serum viremia (by plaque assay on MARC-145 cells, FIG. 2) and serum antibody (by ELISA using HerdChek PRRS from IDEXX, FIG. 3). Gross and microscopic lesions of the lung were observed upon necropsy. There were no significant differences between the two virus-infected groups, indicating that rP129A-1 replicates in pigs and causes clinical disease which is quantitatively and qualitatively similar to its non-recombinant parent virus.

Example II

Deletion of ORF7 (Nucleocapsid Gene) from the North American PRRS Virus; Preparation of a Negatively-Marked, Replication-Defective Vaccine Thereby The viral nucleocapsid gene (ORF7) was partially deleted from an infectious cDNA clone of the PRRS virus of the present invention. The resulting recombinant modified PRRS virus would be expected to be replication-defective in pigs. This recombinant modified PRRS virus can be used as a vaccine to induce an immune response to the other PRRS virus proteins without the risks of clinical disease, spread to non-vaccinated animals, or reversion to virulence associated with attenuated live vaccines. In addition to being very safe, such a vaccine virus would also be "negatively marked", in the sense that it would allow exposure to field isolates of PRRS virus to be determined serologically, even in the presence of antibody to the vaccine virus. Antibodies to the ORF7 protein are commonly found in the sera of PRRS virus-infected pigs, whereas pigs vaccinated with an ORF7-deleted PRRSV would lack antibodies to the ORF7 protein.

Deletion of ORF7 from an infectious clone was accomplished as follows: Plasmid p2_7D-4 (see FIG. 1) was used as template in PCR to amplify the 5' and 3' flanking regions upstream and downstream of ORF7. The upstream flank forward primer 5'-ATTAGATCTTGC CACCATGGTGGGGAAATGCTTGAC-3' (SEQ ID NO:27) (which binds to genome positions 13,776-13,791 near the beginning of ORF5 and contains additional restriction sites which are irrelevant to the current cloning) and the upstream flank reverse primer 5'-CTTTACGCGTTTG CTTAAGTTATTTGGCGTATTTGACAAGGTTTAC-3' (SEQ ID NO:28) (which binds to genome positions 14,857-14,902 at the junction of ORFs 6 and 7) amplified a fragment of 1147 bp. The reverse primer introduced MluI and AflII sites and a single base change at position 14,874, destroying the ATG start codon for ORF7 without altering the tyrosine encoded in the overlapping ORF6. For the downstream flank, the forward primer 5'-CAACAC GCGTCAGCAAAAGAAAAAGAAGGGG-3'

(SEQ ID NO:29) (positions 14,884-14,914 near the 5' end of ORF7, introduced an MluI site) and reverse primer 5'-GCGCGTTGGCCGATTC ATTA-3' ATTA-3' (SEQ ID NO:30) (downstream of the viral genome in the pCR2.1 plasmid) amplified a 462 bp fragment. A 3-way ligation was performed, using the 611 bp BstEII-MluI fragment of the upstream flank PCR product, the 575 bp MluI-SpeI fragment of the downstream flank PCR product, and the 6653 bp BstEII-SpeI fragment from plasmid p2_7D-4 (all fragments were gel purified following digestion). The resulting plasmid p2_7Ddelta7+7023 was deleted in the first seven amino acids of ORF7, and lacks a functional ATG start codon. Two new restriction sites which are absent in both the viral genome and the plasmid backbone, AflII and MluI, have been inserted to facilitate directional cloning of foreign genes into the space previously occupied by the 5' end of ORF7.

The changes made in p2_7Ddelta7+7023 were incorporated into a full-length genomic clone by ligating the 3683 bp Eco47III-SpeI fragment of p2_7Ddelta7+7023 with the 15,214 bp Eco47III-SpeI fragment of pCMV-S-p129. The resulting plasmid pCMV-S-p129delta7+7023 was used to transfect cells.

Since nucleocapsid is essential for viral growth, it is necessary to provide this protein in order to allow generation and replication of an ORF7-deficient PRRS virus. This can be accomplished using a helper virus or a complementing cell line, for example. ORF7-expressing MARC-145 cell lines can be created by stably transfecting cells with a plasmid containing both the ORF7 gene from P129A and the neomycin resistance gene. After selecting for neomycin resistance using the antibiotic G418, single-cell colonies can then be expanded and characterized. Clonal MARC-145-derived cell lines that are positive for ORF7 expression by both immunofluorescence and RT-PCR can be transfected with RNA from pT7P129delta7 in order to generate ORF7-deficient P129 virus.

Similar strategies can be used to generate PRRS viruses deficient in other structural genes (ORFs 2, 3, 4, 5, or 6), or deficient in all or portions of non-structural genes 1a and 1b. In addition, multiple deletions can be engineered into a single PRRS virus, and these can be grown in complementing cells which provide all necessary functions. Such gene-deficient PRRS viruses are likely to be either partially or completely attenuated in pigs, making them useful as vaccines against PRRS. They can also be used to distinguish vaccinated animals from animals infected with a wild-type PRRS virus as discussed above and/or as vectors for vaccinating animals with epitopes of other porcine pathogens (see Example III, below).

Example III

Insertion of Heterologous Genes into the North American PRRS Virus Genome; Use of PRRS Virus as a Vector, and a Positively-Marked North American PRRS Virus In Example II, above, AflII and MluI restriction enzyme sites were inserted into the region formerly occupied by the 5' end of ORF7. These sites are absent in the P129A genome and in the pCR2.1 and pCMV plasmids, and can be used in the directional cloning of foreign (heterologous) genes into the viral genome for expression. Potential leader-junction sites for transcription of the ORF7 subgenomic RNA at positions 14,744-14,749 (ATAACC) and 14,858-14,863 (TAAACC) are not affected by deletion of the ORF7 coding sequence, and can function in transcription of a foreign gene. Foreign (heterologous) genes can include genes from other genes from other PRRS virus isolates or genotypes, and/or genes from other non-PRRS pathogens, either pathogens that infect swine or pathogens that infect mammals other than swine, or avians.

In addition, these foreign genes (or portions thereof) can provide antigenic epitopes which are not normally found in swine. Such epitopes can be used to "positively mark" a vaccine, so that successful vaccination can be monitored serologically, even in the presence of antibody to field or conventional vaccine strains of PRRS virus. A positive marker needs not be a separate expression cassette. An antigenic epitope can be fused to a structural gene of the PRRS virus. For example, the upstream flank reverse primer described in Example I, above, can be extended in such a way as to add a carboxyl-terminal fusion of a non-PRRS virus antigenic epitope to the ORF6 membrane protein. The presence of antibody to this epitope in swine indicates successful vaccination.

Example IV

Cellular Expression of a PRRS Virus by Direct Transfection of cDNA into Cells

The eukaryotic expression vector pCMV-MC1 (SEQ ID NO:31) was derived from the commercially available plasmid pCMVbeta (Clontech) by replacing the LacZ coding sequence between two Not I sites with a linker containing Not I, EcoR V, Avr II, Bgl II, C/a I, Kpn I, Pac I, Nhe I, Swa I, Sma I, Spe I and Not I sites. Modification of the human CMV immediate early promoter was accomplished by substituting the sequence between the Sac I and the second Not I sites of pCMV-MC1 with a synthetic linker (shown below). The linker contains a half site for Sac I following by Pac I, Spe I and a half site for Not I. After annealing the two single stranded oligonucletides, the linker was cloned into pCMV-MC1 between the Sac I and Not I sites, and a selected clone was designated pCMV-S1. The Spe I site of pCMV-S1 could not be cut, possibly due to a mistake in the oligo sequence. Therefore, the fragment between Pac I and Hind III in pCMV-S1 was replaced with Pac I (at position 877)-Hind III (at position 1162) fragment from pCMV-MC1. Thus, a Spe I site was regained. This final construct (pCMV-S) was used to clone the full length P129 genome.

Linker sequence (SEQ ID NO: 32, first below and SEQ ID NO: 33, second below):

```
5' CGTTAATTAAACCGACTAGTGC 3'

3' TCGAGCAATTAATTTGGCTGATCACGCCGG 5'
         Pac I      Spe I
   Sac I                       Not I
```

The sequence immediately upstream of the 5' end of the P129 genome was modified to contain proper spacing and a convenient restriction enzyme site (Pac I). This was done by designing appropriate PCR primers (SEQ ID NO:34 and SEQ ID NO:35) for amplification from pT7P129. After digestion with Pac I and Aat II, this PCR fragment was subcloned into the Pac I and Aat II sites of pT7RG (FIG. 1). The resulting plasmid was designated pT7RG-deltaT7.

The final construction was completed by subcloning the viral sequences from pT7RG-deltaT7 at the Pac I and Nde I sites into pT7P129, creating pT7P129-deltaT7. The full length P129 genome was digested from pT7P129-deltaT7 at Pac I and Spe I and transferred into pCMV-S at the Pac I and Spe I sites. This constructed was named pCMV-S-P129.

The sequence of the region of modification between the CMV promoter TATA box and the 5' end of the P129 sequence in pCMV-S-P129 is shown in SEQ ID NO:36 and schematically presented below:

```
  TATATAAGCAGAGCTCGTTAATTAAACCGTCATGACGTATAGGTGTTGGC
5' TATA box  Sac I  Pac I         Start  of  P129     3'
```

To test the use of the CMV promoter to initiate PRRS virus infection in cells, pCMV-S-P129 plasmid DNA (0.5 or 1.0 μg) was transfected into MARC-145 cells by lipofection using Lipofectamine™ (Life Technologies Inc.). PRRS virus specific cytopathic effect was observed after transfection and the presence of PRRS virus antigen was determined by the immunofluorescent antibody test.

PRRS virus was generated efficiently from pCMV-S-P129, and the progeny virus can be passaged on MARC-145 cells. This demonstrates that a PRRS virus infection can be initiated directly from a plasmid cDNA encoding a PRRS virus, without an in vitro transcription step. Furthermore, pCMV-S-P129 generated a greater amount of progeny virus compared to plasmids wherein the 3' end of the pCMV promoter was not immediately in front of the start of the sequence encoding the North American PRRS virus.

Example V

Deletion of ORF4 from the North American PRRS Virus; Preparation of a Replication-Defective Vaccine Thereby A portion of the gene for ORF4, which encodes a membrane glycoprotein, was deleted from an infectious cDNA clone of the PRRS virus of the present invention. The resulting recombinant modified PRRS virus is expected to be replication-defective in pigs and to induce an immune response to the other PRRS virus proteins without the risks of clinical disease; spread to non-vaccinated animals, or reversion to virulence associated with attenuated live vaccines.

Deletion of ORF4 from an infectious clone was accomplished as follows. Plasmid p2_7D-4 (see FIG. 1) was used as template in PCR to amplify the 5' and 3' flanking regions upstream and downstream of ORF4. The upstream flank forward primer was 5'-AGGTCGAC GGCGGCAATTGGTTTCACCTAGAGTGGCTGCGTCCCTTCT-3' (SEQ ID NO:37). This primer binds to genome positions 13194-13241, near the beginning of ORF4, and introduces a mutation at position 13225 which destroys the ATG start codon of ORF4 without altering the overlapping amino acid sequence of ORF3. The upstream flank reverse primer was 5'-TCTTAAGCATTGGCTGTGATGGTGATATAC-3' (SEQ ID NO:38). This primer binds to genome positions 13455-13477 within the ORF4 coding region, downstream of ORF3, and introduces an AflII site. For the downstream flanking region, the forward primer was 5'-CTTC TTAAGTCCACGCGTTTTCTTCTTGCCTTTTCTATGCTTCT-3' (SEQ ID NO:39). This primer binds to genome positions 13520-13545 in the middle of ORF4, and introduces AflII and MluI sites for directional cloning of foreign genes. The reverse primer was 5'-TGCCCGGTCCCTT GCCTCT3' (SEQ ID NO:40). This primer binds to genome positions 14981-14999 in the ORF7 coding sequence. A three-way ligation was performed using the SalI-AflII fragment of the upstream flank PCR product, the AflII-BstEII fragment of the downstream flank PCR product, and the SalI-BstEII fragment from plasmid p2_7D-4. All fragments were gel-purified following digestion. The resulting plasmid p2_7D-4-delta4N has 42 bases of the central portion of ORF4 deleted and replaced with a 15 base artificial cloning site. The cloning site contains two restriction sites (AflII and MluI) that are absent from both the viral genome and the plasmid backbone. These can be used to facilitate directional cloning of foreign genes into the space previously occupied by ORF4. The cloning site also contains a stop codon (TAA) that is in frame with ORF4 and further assures that functional ORF4 protein is not produced.

It was found that a more extensive deletion of the ORF4 coding sequence can be made without interfering with expression of the downstream ORF5 envelope gene. In this case a shorter downstream flanking region was amplified by PCR using the same template and reverse primer, and using forward primer 5'-GTTTACGCGTCGCTCCTTGGTGGTCG-3' (SEQ ID NO:41). This primer binds to genome positions 13654-13669 near the 3' end of ORF4, and contains an AflII site. Two-way ligation between the AflII-BstEII fragment of the downstream flank PCR product and the AflII-BstEII fragment from plasmid p2_7D-4-delta4N yielded the new plasmid p2_7D-4-delta4NS. This plasmid has 176 bases of the ORF4 coding sequence deleted and replaced with the 15 base cloning site.

The changes made in p2_7D-4-delta4N and p2_7Ddelta4NS were incorporated into the full-length genomic clone by replacing the BsrGI-SpeI fragment from pCMV-S-P129 with the modified BsrGI-SpeI fragments from p2_7D-4-delta4N and p2_7D-4-delta4NS. The resulting plasmids pCMV-S-P129delta4N and pCMV-S-P129delta4NS were used to transfect cells.

In contrast to pCMV-S-P129, transfection of MARC-145 cells with plasmids pCMV-S-P129delta4N or pCMV-S-P129delta4NS did not result in viral plaques or fluorescent foci. Individual transfected cells can be seen to be producing the ORF7 nucleocapsid protein, suggesting that the ORF4 gene product is not required for RNA replication or expression of viral genes, but is essential for release of infectious progeny virus. Since deletion of ORF4 is lethal to virus replication, it is necessary to provide this protein. This can be accomplished by using a complementing cell line. We created ORF4-expressing MARC-145 cell lines by stable transfecting cells with a plasmid containing both ORF4 and the neomycin resistance gene. After selection for neomycin resistance using the antibiotic G418, single-cell colonies were expanded and characterized. After transfection with pCMV-S-P129delta4NS, three ORF4-expressing cell clones yielded live virus that can be propagated in these cells but not in MARC-145 cells. One of these, MARC400E9, was further characterized. Immunofluorescent staining for viral nucleocapsid in MARC400E9 cells transfected with plasmid pCMV-S-P129delta4NS was positive.

Virus derived by transfecting MARC400E9 cells with the pCMV-S-P129delta4NS plasmid (designated P129delta4NS) was amplified by passaging several times on MARC400E9 cells and was used to vaccinate pigs against a virulent PRRSV challenge. Live virus was formulated with one of three different types of adjuvant or used without adjuvant, and was delivered in two doses by one of two vaccination routes (intranasal followed by intramuscular, or intramuscular followed by a second intramuscular dose).

At approximately three weeks (Day 0) and five weeks (Day 14) of age, seronegative conventional pigs were vaccinated according to the Table 2, below. The pigs in Group J were considered sentinel pigs and were necropsied approximately one week prior to challenge to evaluate the health status of all pigs.

TABLE 2

Test groups selected for vaccination derived from P129delta4NS

| Group | Vaccine | N | Route* | Adjuvant |
|---|---|---|---|---|
| A | P129delta4NS | 10 | IN/IM | None |
| B | P129delta4NS | 10 | IM/IM | None |
| C | P129delta4NS | 10 | IN/IM | rmLT** |
| D | P129delta4NS | 10 | IM/IM | rmLT |
| E | P129delta4NS | 10 | IN/IM | QuilA/Cholesterol |
| F | P129delta4NS | 10 | IM/IM | QuilA/Cholesterol |
| G | P129delta4NS | 10 | IN/IM | Amphigen |
| H | P129delta4NS | 10 | IM/IM | Amphigen |
| I | PBS only | 10 | IM/IM | None |
| J | None | 10 | NA | NA |

*IN—intranasal; IM—intramuscular.

**recombinant mutant heat-labile enterotoxin from *E. coli*.

The first and second intramuscular vaccinations were administered in the left and right sides of the neck, respectively. On Days 0, 13, 21 and 28, blood samples were collected for serology (IDEXX HerdChek PRRS ELISA). At approximately three weeks following the second vaccination (Day 35), all pigs were challenged with 1 mL of parental P129 virus instilled drop-wise in each nostril (a total of 2 mL/pig or $1.2\times10^5$ pfu). On Days 35, 38, 42 and 45, blood samples were collected from all pigs for serology and for PRRSV titration (by TCID50 assay). On Days 45 and 46, pigs were euthanized and necropsied. Lungs were removed from the chest cavity, examined for PRRS lesions, and photographed. Necropsies were performed at the Animal Disease Research and Diagnostic Laboratory (ADRDL) at South Dakota State University, Brookings, S. Dak.

The serological results showed induction of anti-PRRSV antibody in several of the vaccinated groups prior to challenge, and priming of the humoral immune system for a rapid post-challenge antibody response in all vaccinated groups. Immediately before challenge (Day 35), the average S/P ratio (Sample/Positive control ratio) value in the unvaccinated controls (group I) was 0.003. All eight of the vaccinated groups had higher values, ranging from 0.005 (group B) up to 0.512 (group H). By one week after challenge (Day 42), the control group was group was beginning to mount an antibody response to the challenge virus (S/P value of 0.171). All eight vaccinated groups had much higher antibody levels, ranging from 0.858 (group B) to 1.191 (group G). This represents an increase in anti-PRRSV antibodies of approximately 5- to 10-fold as a result of priming of the humoral immune system.

TABLE 3

Anti-PRRSV antibody levels (S/P ratios)

| | | Day-1 | Day-13 | Day-21 | Day-28 | Day-35 | Day-38 | Day-42 | Day-45 |
|---|---|---|---|---|---|---|---|---|---|
| Group A | None/IN | 0.003 | 0.008 | 0.004 | 0.002 | 0.015 | 0.102 | 0.862 | 2.270 |
| Group B | None/IM | 0.005 | 0.015 | 0.024 | 0.022 | 0.005 | 0.105 | 0.858 | 2.053 |
| Group C | rmLT/IN | 0.002 | 0.030 | 0.015 | 0.021 | 0.016 | 0.108 | 1.219 | 2.653 |
| Group D | rmLT/IM | 0.002 | 0.042 | 0.143 | 0.149 | 0.138 | 0.229 | 1.271 | 2.679 |
| Group E | QuilA/IN | 0.015 | 0.039 | 0.084 | 0.048 | 0.013 | 0.097 | 1.217 | 2.299 |
| Group F | QuilA/IM | 0.001 | 0.020 | 0.104 | 0.115 | 0.085 | 0.109 | 1.240 | 2.593 |
| Group G | Amph/IN | 0.002 | 0.001 | 0.047 | 0.051 | 0.061 | 0.080 | 1.919 | 3.484 |
| Group H | Amph/IM | 0.022 | 0.006 | 0.460 | 0.531 | 0.512 | 0.492 | 1.601 | 3.371 |
| Group I | PBS only | 0.008 | 0.020 | 0.001 | 0.001 | 0.003 | 0.053 | 0.171 | 0.881 |

Following challenge with virulent PRRSV, serum viremia was determined. At three days post challenge (Day 38) the titer of virus in the unvaccinated control group had reached 2.58 logs. All eight of the vaccinated groups showed reduced viremia, ranging from 2.52 (group E) down to 1.07 logs (group H). This represents more than a 30-fold reduction in virus levels relative to the control group, see Table 4.

TABLE 4

| Serum viremia (log 10 TCID50 titers) on day 38 (three days post challenge) | | |
|---|---|---|
| Group A | None/IN | 2.18 |
| Group B | None/IM | 1.98 |
| Group C | rmLT/IN | 2.15 |
| Group D | rmLT/IM | 2.48 |
| Group E | QuilA/IN | 2.52 |
| Group F | QuilA/IM | 1.65 |
| Group G | Amph/IN | 1.74 |
| Group H | Amph/IM | 1.07 |
| Group I | PBS only | 2.58 |

At necropsy, all pigs were examined for the presence of macroscopic lung lesions resulting from the PRRS challenge virus. In the unvaccinated control group, 90% of the animals showed lung lesions. In contrast, all eight of the vaccinated groups showed reduced levels of lung lesions (ranging from 80% in group D down to 22% in group A). Vaccination reduces damage to the lungs that result from PRRSV infection. See Table 5.

TABLE 5

| Number of pigs with macroscopic lung lesions/total pigs (percent positive) | | |
|---|---|---|
| Group A | None/IN | 2/9 (22%) |
| Group B | None/IM | 7/10 (70%) |
| Group C | rmLT/IN | 6/10 (60%) |
| Group D | rmLT/IM | 8/10 (80%) |
| Group E | QuilA/IN | 5/10 (50%) |
| Group F | QuilA/IM | 4/10 (40%) |
| Group G | Amph/IN | 7/10 (70%) |
| Group H | Amph/IM | 5/9 (56%) |
| Group I | PBS only | 9/10 (90%) |

The above swine data demonstrates the process of vaccinating swine with the recombinant North American PRRS virion containing the ORF 4 deletion. The results of the above data illustrate that the P129delta4NS virus, which is deleted in ORF4, is useful as a vaccine to protect pigs from disease caused by the PRRS virus. Efficacy of the vaccine may be increased by formulation with various adjuvants and by changing the route of administration.

Example VI

Use of Gene-Deleted PRRS Virus as a Vector for Expression of Foreign Genes

In order to determine whether heterologous genes can be expressed from a gene-deleted PRRS virus, we inserted a copy of green fluorescent protein (GFP) into the site of ORF4 deletion in plasmid pCMV-S-P129delta4N. The GFP gene was amplified from a commercially available plasmid vector using PCR primers that introduced an AflII site at the 5' end of the gene and an MluI site at the 3' end of the gene. The resulting plasmid pCMV-S-P129delta4N-GFP was used to transfect MARC-145 and MARC400E9 cells. As anticipated, MARC-145 cells did not support replication of the ORF4-deleted virus. Single green cells resulting from primary transfection were seen under the UV scope, indication that GFP was being expressed, but the virus did not spread to neighboring cells and no CPE was observed. In contrast, large green foci were observed in transfected MARC400E9 cells. Visible plaques formed and merged, destroying the monolayer. These results indicate that foreign genes can be expressed from ORF4-deleted PRRS virus, and that increasing the size of the viral genome by 692 bases (4.5%) does not interfere with packaging of the viral RNA into infectious particles.

Example VII

Use of Replication-Competent PRRS Virus as a Vector for Expression of Foreign Genes In order to determine whether heterologous genes can be expressed from a replication-competent PRRS virus, we inserted a copy of GFP into the region between ORF1b and ORF2. Since the leader/junction (L/J) sequence for ORF2 lies within ORF1b, this L/J sequence was used to drive expression of the GFP gene and a copy of the ORF6 L/J sequence was inserted downstream from GFP to drive expression of ORF2.

Plasmid p2__7D-4 (see FIG. 1) was used as template in PCR to amplify the 5' and 3' flanking regions upstream and downstream of the insertion site. The upstream flank forward primer was 5'-AACAGAAGAGTTGTCGGGTCCAC-3' (SEQ ID NO:42). This primer binds to genome positions 11699-11721 in ORF1b. The upstream flank reverse primer was 5'-GCTTT GACGCGTCCCCACTTAAGTTCAATTCAGGCCTAAAGTTGGTTCA-3' (SEQ ID NO:43). This primer binds to genome positions 12031-12055 in ORF1b and adds AflII and MluI sites for directional cloning of foreign genes between ORF1b and ORF2. The downstream flank forward primer was 5'-GCGACGCGTGTTCCGTGGCAACCCCTTTAACCAGAGTTTCAGCGG AACAATGAAATGGGGTCTATACAAAGCCTCTTCGACA-3' (SEQ ID NO:44). This primer binds to genome positions 12056-12089 in ORF2 and contains an MluI site followed by the 40 bases that precede the start of ORF6 (containing the ORF6 L/J sequence). The downstream flank reverse primer was 5'-AACAGAACGGCACGATACACCACAAA-3' (SEQ ID NO:45). This primer binds to genome positions 13819-13844 in ORF5. A three-way ligation was performed using the Eco47II-MluI fragment of the upstream flank PCR product, the MluI-BsrGI fragment from the downstream flank PCR product, and the Eco47II-BsrGI fragment from pCMV-S-P129. The resulting plasmid pCMV-S-P129-1bMCS2 contains the entire P129 genome with a cloning site and an additional L/J site between ORF1b and ORF2. The plasmid produces functionally normal virus when transfected into MARC-145 cells.

The GFP gene from a commercially available plasmid was PCR amplified using primers that add an AflII site to the 5' end and an MluI site to the 3' end of the gene. After digestion of the PCR fragment and PCMV-SP129-1bMCS2 with AflII and MluI, the insert was ligated into the vector to yield plasmid pCMV-S-P129-1bGFP2. This plasmid produced green plaques when transfected into MARC-145 cells. The resulting virus can be passaged onto MARC-145 cells and continued to produce green plaques when observed under the UV scope. Thus, foreign genes may be expressed from replication-competent PRRS virus vectors. The P129-1 bGFP2 virus contains a genome which is 774 bases (5%) longer than that of its P129 parent, yet it is packaged normally.

Example VIII

Deletion of ORF 2 (Minor Structural Protein) from the North American PRRS Virus; Preparation of a Replication-Defective Vaccine The following example illustrates the preparation of the North American PRRS virions containing the ORF 2 deletion.

The viral minor structural protein encoded by ORF2 is deleted from an infectious cDNA clone of the PRRS virus of the present invention. The resulting recombinant modified PRRS virus is replication-defective in pigs and can induce an immune response to the other PRRS virus proteins without the risks of clinical disease, spread to non-vaccinated animals, or reversion to virulence associated with attenuated live vaccines.

Deletion of ORF2 from an infectious clone was accomplished as follows. Plasmid p2__7D-4 (see FIG. 1) was used as template in PCR to amplify the 5' and 3' flanking regions upstream and downstream of ORF2. The upstream flank forward primer was 5'-CAAAGGGC GAAAAACCGTCTATCA-3' (SEQ ID NO:46), which binds within the cloning vector. The upstream flank reverse primer was 5'-CCCCACTTAAGTTCAATTCAGGC-3' (SEQ ID NO:47), which binds to genome positions 12045-12067 near the beginning of ORF2. The downstream flank forward primer was 5'-GCTCCTTAAGAACAACGCGTCGCCATTGAAGCCGAGA-3' (SEQ ID NO:48), which binds to genome positions 12492-12528. The downstream flank reverse primer was 5'-GCAAGCCTAATAACGAAGCAAATC (SEQ ID NO:49), which binds to genome positions 14131-14154. A 3-way ligation was performed, using the XhoI-AflII fragment of the 5' flanking PCR product, the AflII-BsrGI fragment of the 3' flanking PCR product, and the large XhoI-BsrGI fragment from plasmid p2__7D-4. All fragments were gel purified following restriction enzyme digestion. The resulting plasmid p2__7D4delta2 was deleted in the region of ORF2 that does not overlap ORF3 or it's 5' transcriptional regulatory sequences. Two restriction sites that are absent in both the viral genome and the plasmid backbone, AflII and MluI, have been introduced to facilitate directional cloning of foreign genes into the space previously occupied by ORF2.

The changes made in p2__7D4delta2 were incorporated into a full-length genomic clone by replacing the AfeI-BsrGI fragment from pCMV-S-P129 with the modified sequence from p2__7D4delta2. The resulting plasmid pCMV-S-P129delta2 was used for transfections.

Since the deletion of ORF2 is lethal to virus replication, it is necessary to provide this protein in trans to allow generation of ORF2-deficient PRRS virus. This can be accomplished by using a complementing cell line. We created ORF2-expressing MARC-145 cell lines were created by stably transfecting cells with a plasmid containing both the ORF2 gene from P129A and the neomycin resistance gene. After selecting for neomycin resistance using the antibiotic G418, single-cell colonies were expanded and characterized. After transfecting with pCMV-S-P129delta2, three cell clones yielded live viruses that can be propagated and passed only in these ORF2-expressing cells. This virus was designated P129delta2.

Recombinant virus P129delta2 was used to vaccinate groups of 20 sero-negative conventional pigs. At three weeks of age (Day 0) and six weeks of age (Day 20), pigs were vaccinated according to Table 6, below. Controls were mock vaccinated with phosphate buffered saline (PBS). Amphigen adjuvant was not viricidal to the live vaccine virus.

TABLE 6

Various groups of 20 sero-negative conventional pigs vaccinated with P129delta2.

| Treatment Group | Route* | Adjuvant | Titer/Dose (log10 $TCID_{50}$) |
|---|---|---|---|
| P129delta2 IM | IM/IM | 5% Amphigen | 5.8 |
| P129delta2 IT | IT/IT | None | 5.7 |
| Mock vaccinated (PBS) Controls | IT/IT | None | NA |

*IM—intramuscular; IT—intratracheal.

At three weeks following second vaccination (Day 42, 9 weeks of age), pigs were challenged with approximately 2.8 mL of virulent P129 challenge virus ($3.41\times10^5$ $TCID_{50}$/mL) in each nostril, to achieve a total challenge volume of 5.6 mL ($1.91\times10^6$ $TCID_{50}$). Pigs were bled periodically for determination of anti-PRRSV antibody (IDEXX HerdChek PRRS ELISA) and serum viremia ($TCID_{50}$ assay).

TABLE 7

Anti-PRRSV antibody levels (S/P ratios)

| | Day 2 | Day 19 | Day 28 | Day 34 | Day 42 | Day 52 | Day 55 | Day 63 |
|---|---|---|---|---|---|---|---|---|
| P129delta2 IM | 0.026 | 0.132 | 1.265 | 1.319 | 1.389 | 1.995 | 2.322 | 2.02 |
| P129delta2 IT | 0.011 | 0.004 | 0.026 | 0.115 | 0.036 | 1.306 | 1.584 | 1.501 |
| Mock vaccinated (PBS) Controls | 0.001 | 0.002 | 0.071 | 0.003 | 0.004 | 0.763 | 1.362 | 1.395 |

Two vaccinations with live Amphigen-adjuvanted P129delta2 intramuscularly resulted in a marked increase in anti-PRRSV antibody in the serum prior to challenge, as well as an anamnestic response following challenge. Two intratracheal vaccinations with unadjuvanted P129delta2 were less effective, but nevertheless resulted in a slight increase in antibody level prior to challenge and a more rapid response following challenge, relative to the mock-vaccinated control group.

TABLE 8

Results from two vaccinations with live Amphigen-adjuvanted P129delta2 and control.
Serum titer (log 10 $TCID_{50}$) and number of positive pigs following PRRSV challenge

| | | Days post-challenge | | | | | |
|---|---|---|---|---|---|---|---|
| Treatment | | 0 | 5 | 8 | 10 | 14 | 21 |
| P129delta2 IM | Titer | 0.0 | 1.5 | 0.3 | 0.0 | 0.0 | 0.0 |
| | Positive/Total | 0/19 | 13/18 | 4/18 | 1/18 | 0/8 | 0/8 |
| | (%) | (0%) | (72%) | (22%) | (6%) | (0%) | (0%) |
| P129delta2 IT | Titer | 0.0 | 2.3 | 2.1 | 1.5 | 0.5 | 0.2 |
| | Positive/Total | 0/20 | 19/20 | 19/20 | 17/20 | 4/10 | 1/10 |
| | (%) | (0%) | (95%) | (95%) | (85%) | (40%) | (10%) |
| Mock vaccinated | Titer | 0.0 | 2.4 | 2.0 | 1.4 | 0.3 | 0.0 |
| (PBS) Controls | Positive/Total | 0/20 | 19/19 | 19/19 | 16/19 | 3/9 | 0/9 |
| | (%) | (0%) | (100%) | (100%) | (84%) | (33%) | (0%) |

Intramuscular vaccination with two doses of live Amphigen-adjuvanted P129delta2 virus resulted in a reduction of the number of viremic pigs (from 100% to 72%), reduction in the duration of viremia (from about 21 days to about 14 days), and reduction in the average serum virus load of nearly one log at 5 days post-infection (the peak of viremia) and more than one log at later times. Intratracheal vaccination with unadjuvanted P129delta2 showed little or no reduction in viremia relative to the mock-vaccinated control group.

Example IX

Insertion of Unique MluI and SgrAI Restriction Sites into the PRRS Virus Genome within Nsp2

The QuikChange® II XL Site-Directed Mutagenesis kit (Stratagene; La Jolla, Calif.) was used to introduce a unique MluI restriction enzyme site into the PRRS virus genome at nucleotide position 3,219 using plasmid pCMV-S-P129 as template. Genome position 3,219 lies within the nonstructural protein 2 (nsp2) coding region, which is part of ORF1a (FIG. 5). This site is located within the hypervariable C-terminal portion of nsp2. The sequence of the parental parental virus beginning at genome position 3,219 (ACACGC) is such that changing only two nucleotides (ACGCGT) allows the introduction of an MluI site without altering the encoded amino acid sequence. The mutagenic primers used to insert the MluI site (MluI F and MluI R) are shown in Table 1. QuikChange II XL reactions were as recommended by the manufacturer and contained 150 picomoles of each primer and 10 ng of plasmid DNA as template. Reaction conditions were as follows: initial denaturation at 95° C. for 60 seconds, 18 cycles of 95° C. denaturation for 50 seconds, 60° C. annealing for 50 seconds, and 68° C. extension for 20 minutes, concluding with a 7 minute incubation at 68° C. Successful introduction of the new site was determined based on the ability of the resulting plasmid to be cut with MluI, and confirmed by DNA sequencing. The new plasmid was named pCMV-S-P129-Nsp2-Mlu, and was used as a backbone for the insertion foreign DNA fragments.

A unique SgrAI restriction enzyme site was inserted into plasmid pCMV-S-P129-Nsp2-Mlu as follows. A 4500 bp PCR product (genome positions 3201-7700) was amplified using template pCMV-S-P129-Nsp2-Mlu, primers Mlu-F and 7700-R (Table 1), and ExTaq™ polymerase (TakaRa Mirus Bio; Madison, Wis.) according to the manufacturer's directions. The forward primer Mlu-F contains the unique MluI site added in the previous step, and the reverse primer 7700-R contains a unique PmeI site to be used in a subsequent cloning step. Reactions conditions were: initial denaturation at 95° C. for 120 seconds, 30 cycles of 94° C. denaturation for 35 seconds, 58° C. annealing for 35 seconds, and 72° C. extension for 4.5 minutes. The resulting PCR product was cloned the TOPO PCR XL cloning kit (Invitrogen Corp.; Carlsbad, Calif.). The QuikChange II XL Site-Directed Mutagenesis Kit was used to introduce a unique SgrAI site beginning at genome position 3614 according to the manufacturer's directions. The original sequence TACCGGTG was changed to CACCGGTG without altering the encoded amino acid sequence, using primers SgrAI-F and SgrAI-R (Table 1). Reactions conditions were: initial denaturation at 95° C. for 60 seconds, 18 cycles of 95° C. denaturation for 50 seconds, 60° C. annealing for 50 seconds, and 68° C. extension for 9 minutes, followed by a 68° C. polishing reaction for 7 minutes. After transformation, plasmids containing the new SgrAI site were selected by restriction digestion and sequence analysis. The 4,456 bp Mlui-PmeI fragment from this plasmid was ligated to the 14,436 bp MluI-PmeI fragment of PCMV-S-P129-Nsp2-Mlu to yield pCMV-S-P129-Nsp2-Mlu/SgrA. This plasmid was transfected into MARC-145 cells using Lipofectamine 2000 (Invitrogen Corp.; Carlsbad, Calif.) according to the manufacturer's instructions. Three days post-transfection lysates were titrated by limiting dilution. Infectious virus was recovered from plasmid pCMV-S-P129-Nsp2-Mlu/SgrA at levels that were similar to plasmids pCMV-S-P129 and pCMV-S-P129-Nsp2-Mlu.

Example X

Insertion of Green Fluorescent Protein (GFP) into Nsp2

MluI sites were placed on the 5' and 3' ends of GFP, amplified by PCR from plasmid pEGFP-C3 (Clontech, Mountain View, Calif.), using gene-specific PCR primers GFP-Mlu-F and GFP-Mlu-R (Table 1). ExTaq™ polymerase (TakaRa Mirus Bio; Madison, Wis.) was used according to the manufacturer's recommendation. Reactions conditions were: initial denaturation at 95° C. for 120 seconds, 30 cycles of 94° C. denaturation for 35 seconds, 56° C. annealing for 35 seconds, and 72° C. extension for 60 seconds. The PCR product was digested with MluI and ligated into MluI-digested pCMV-S-P129-Nsp2-Mlu. DNA sequencing confirmed that GFP had been inserted in-frame, in the forward orientation, into nsp2. The new plasmid was designated pCMV-S-P129-Nsp2-Mlu-GFP.

Plasmids pCMV-S-P129, pCMV-S-P129-Nsp2-Mlu, and pCMV-S-P129-Nsp2-Mlu-GFP were transfected into the MARC-145 monkey kidney cell line in order to generate infectious virus. Cell lines were maintained at 37° C., 5% $CO_2$ in modified Eagle's medium (MEM) supplemented with 8% fetal bovine serum, 0.008% Fungizone and 0.01% penicillin/streptomycin. Approximately one day prior to transfection, $2\times10^5$ cells/well were seeded into a 12-well plate. Transfection of infectious cDNA clones was performed using Lipofectamine 2000 (Invitrogen, Carlsbad, Calif.) according to the manufacturer's instructions. At 4 days post-transfection, virus was harvested by subjecting the infected cells to three freeze-thaw cycles. Cell debris was removed by centrifugation at 1000×g for 10 minutes, and virus-containing culture supernatants collected. Recombinant viruses rescued from plasmids pCMV-S-P129, pCMV-S-P129-Nsp2-Mlu, and pCMV-S-P129-Nsp2-Mlu-GFP were designated P129, P129-Nsp2-Mlu, and P129-Nsp2-Mlu-GFP, respectively.

To determine virus titer, end-point dilutions were performed on MARC-145 cells in 96 well plates. Titrations were performed in triplicate and results presented as $TCID_{50}$/ml. Cells were fixed at 3 days post-transfection and immunostained either directly with the nucleocapsid-specific monoclonal antibody SDOW-17 conjugated to FITC, or indirectly with the nucleocapsid-specific primary monoclonal antibodies SR30 or JP24 followed by Alexaflour 594-conjugated goat anti-mouse IgG secondary antibody (Molecular Probes/Invitrogen Corp.; Carlsbad, Calif.). Titers of P129 and P129-Nsp2-Mlu were similar, while the titer of P129-Nsp2-Mlu-GFP was slightly lower. The P129-Nsp2-Mlu-GFP virus-expressed GFP and formed fluorescent green foci. Within the focus of infection, cells with perinuclear green fluorescence are seen, due to expression of the Nsp2-GFP fusion peptide.

For western blot analysis, cells were lysed with 100 ul of 2× Laemmli sample buffer and boiled for 10 min. Proteins were fractionated on SDS-polyacrylamide gels (Bio-Rad; Hercules, Calif.) under reducing conditions. Proteins were transferred onto nitrocellulose membranes and processed at room temperature. Membranes were blocked for 1 hr with 5% nonfat dry milk in washing solution (0.2% Tween 20 in PBS). Affinity purified goat anti-GFP antibody (Rockland Immunochemicals Inc., Gilbertsville, Pa.) was diluted 1:1000 in blocking buffer and incubated with membranes for 1 hr. Membranes were washed three times for 15 minutes with TBS-Tween. Rabbit anti-goat horseradish peroxidase-conjugated antibody (Rockland) was diluted 1:1000 in blocking buffer and incubated with membranes for 1 hr. Membranes were washed three times for 15 minutes with TBS-Tween.

Peroxidase activity was detected using the Supersignal West Pico Chemiluminescent substrate (Pierce Chemical Company; Rockford, Ill.). Western blots identified a 70 kDa peptide from P129-Nsp2-Mlu-GFP infected cells that reacted with anti-GFP antibody. Using a similar procedure, the GFP gene was also inserted into nsp2 at the SgrAI site in the plasmid pCMV-S-P129-Nsp2-Mlu/SgrA. Primers GFP-SgrA-F and GFP-SgrA-R (Table 1) were used to add SgrAI sites to the ends of the GFP gene, using plasmid pEGFP-C3 as template. ExTaq™ polymerase (TakaRa Mirus Bio; Madison, Wis.) was used according to the manufacturer's recommendation. Reactions conditions were: initial denaturation at 95° C. for 120 seconds, 30 cycles of 94° C. denaturation for 35 seconds, 55° C. annealing for 35 seconds, and 72° C. extension for 35 seconds. The PCR product was digested with SgrAI and ligated into SgrAI-digested pCMV-S-P129-Nsp2-Mlu/SgrA. DNA sequencing confirmed that GFP had been inserted in-frame, in the forward orientation, into nsp2. The new plasmid was designated pCMV-S-P129-Nsp2-SgrA-GFP. This plasmid produced infectious virus and fluorescent green foci when transfected into MARC-145 cells.

TABLE 9

PCR primers used to introduce the heterologous genes.

| Primer (genome position) | Sequence | Orientation | SEQ ID NO |
|---|---|---|---|
| MluI-F (3201-3242 | CTGTCAAGTGTTAGGATCACGCGTCCAAAATACTCAGC CAA | Forward | 50 |
| MluI-R (3201-3242 | TTGAGCTGAGTATTTTGGACGCGTGATCCTAACACTTG CAG | Reverse | 51 |
| GFP-Mlu-F | GCCACGCGTGCCACCATGGTGAGCAAGGGCGAG | Forward | 52 |
| GFP-Mlu-R | GCCACGCGTGTTATCTAGATCCGGTGGATCC | Reverse | 53 |
| 7700-R (7661-770 | CTCAAGCCGCTGGCGGCTAGCAGTTTAAACACTGCTCC TTA | Reverse | 54 |
| SgrAI-F (3597-3637) | CTCGGGAAAATAGAAAACACCGGTGAGATGATCAACCA GGG | Forward | 55 |
| SgrAI-R (3597-3637) | CCCTGGTTGATCATCTCACCGGTGTTTTCTATTTTCCC GAG | Reverse | 56 |
| GFP-SgrA-F | GCCGCCCACCGGTGAGGTGAGCAAGGGCGAGGAGCT( TTC | Forward | 57 |
| GFP-SgrA-R | GCCGCCCACCGGTGTTGTTATCTAGATCCGGTGGATC | Reverse | 58 |

All sequences are 5' to 3'. Restriction sites are underlined. Nucleotide positions are based on the sequence of PRRSV strain P129.

Example XI

Construction of PRRS Viruses Having a Deleted Portion of Nsp2

The previously made plasmid pCMV-S-P129-Mlu/SgrA (see Example IX) was used as the backbone plasmid for construction of recombinant PRRS viruses lacking a 132 amino acid region of nsp2, and with either green fluorescent protein (GFP) or the influenza hemagglutinin (HA) tag inserted into the deleted region.

The enhanced GFP gene from a commercially available plasmid (pEGFP-C3, Clontech) was PCR amplified using primers that add MluI and SgrAI restriction enzyme recognition sites to the 5' and 3' ends, respectively. The forward primer was GFP-MLU-F2 (5'-GCC ACGCGTGTGAGCAAGGGCGAGGAGCTG-3') SEQ ID NO. 59 and the reverse primer was GFP-SgrA-R (5'-GCC CACCGGTGTTGTTATCTAGATCCGGTGGATC-3') SEQ ID NO. 58. PCR reactions used ExTaq polymerase (TakaRa Mirus Bio, Madison, Wis.) according to the manufacturer's instructions. Reaction conditions included an initial 120 second denaturation at 95 C, followed by 30 cycles of denaturation at 94 C for 35 seconds, annealing at 55 C for 35 seconds, and extension at 72 C for 35 seconds. After digestion of the PCR fragment and of pCMV-S-P129-Mlu/SgrA with MluI and SgrAI, the insert was ligated into the vector to yield plasmid pCMV-S-P129-Mlu-GFP-SgrA. Deletion of the 132 amino acid region and insertion of GFP (257 amino acids) was confirmed by DNA sequencing. This plasmid produced viable virus, which in turn produced green fluorescent foci of infection when transfected into MARC-145 cells and observed under a fluorescence microscope. This virus was designated P129-Mlu-GFP-SgrA.

The HA tag is a small peptide epitope (YPYDVPDYA), derived from the influenza virus hemagglutinin gene, that reacts with commercially available monoclonal antibodies. A synthetic adapter was created by heating and slowly annealing two phosphorylated oligonucleotides, designated "HA tag F" (5'-CGCGTATACCCATACGACGTCCCAGACTACGCA-3') SEQ ID NO. 60 and "HA tag R" (5'-CCGGTGCGTAGTCTGGGACGTCGTATGGGTATA-3') SEQ ID NO. 61. This adapter, with MluI and SgrAI half-sites, was then ligating into pCMV-S-P129-Mlu/SgrA which was previously digested with MluI and SgrAI. The structure of the resulting plasmid, pCMV-S-P129-Mlu-HA-SgrA, was confirmed by DNA sequencing. An in-frame fusion of the HA tag peptide 9-mer replaces the 132 amino acid deletion in nsp2. The plasmid produced viable virus when transfected into MARC-145 cells. This virus was designated P129-Mlu-HA-SgrA.

In a separate experiment, a simple deletion of the same region (without a simultaneous insertion) was engineered into a different infectious cDNA clone, using a different methodology. The plasmid pCMV-S-P129-PK contains a full-length infectious cDNA clone of the P129 isolate of PRRS virus that was isolated from the serum of an infected pig on primary porcine alveolar macrophage cells, and subsequently passaged 16 times on the porcine kidney cell line PK.9. The PK.9 cell line expresses the CD163 PRRS virus receptor, and is fully permissive to PRRSV infection. A precise deletion of 396 nucleotides, which encodes the 132 amino acid region described above, was generated in pCMV-S-P129-PK using the QuikChange II XL Site-Directed Mutagenesis kit (Stratagene; La Jolla, Calif.) and mutagenic primers P129-PK-3199F (5'-CCCTGTCAAGTGTTAAGATCACAGGTGAGATGATCAACC-3') SEQ ID NO. 62 and P129-PK-3637R (5'-CCCTGGTTGATCATCTCACCTGTGATCTTAACACTTGACAG-3') SEQ ID NO. 63. The resulting plasmid pCMV-S-P129-PK-dnsp2 contained a deletion of nsp2 amino acids 628-759 (confirmed by sequencing), and produced viable progeny virus when transfected into PK.9 transfected into PK.9 cells. This virus was designated P129-PK-dnsp2.

Example XII

Development of an ELISA for the Detection of Serum Antibodies to a 132-Amino Acid Portion of Nsp2

The 132 amino acid portion of nsp2 that is deleted in viruses P129-Mlu-GFP-SgrA and P129-Mlu-HA-SgrA is designated P129-nsp2 (628-759). This peptide, RPKYSAQAIIDLGGPCSGHLQREKEACLRIMREACDAAKLSDPATQEWLSRMWDRVDMLTWR NTSAYQAFRTLDGRFGFLPKMILETPPPYPCGFVMLPHTPAPSVSAESDLTIGSVATEDIPRILGK IENT) (SEQ ID NO. 64) was expressed as a recombinant peptide in *Escherichia coli*, using the pHUE system (Catanzariti A M, Soboleva T A, Jans D A, Board P G, Baker R T. 2004. An efficient system for high-level expression and easy purification of authentic recombinant proteins. Protein Sci. 13:1331-1339). In this expression system, the peptide of interest is cloned and expressed as a histidine-tagged/ubiquitin/PRRS peptide fusion (25 kDa apparent molecular weight on SDS-PAGE). After an initial round of purification by nickel ion affinity chromatography, the histidine-tagged/ubiquitin/PRRS peptide is optionally incubated with histidine-tagged/deubiquinating enzyme to cleave histidine-tagged/ubiquitin from the PRRS peptide. In a second round of nickel ion affinity chromatography, the histidine-tagged/ubiquitin and the histidine-tagged/deubiquinating enzyme are retained on the nickel ion affinity column and the free PRRS peptide is eluted.

The ubiquitin-conjugated P129-nsp2 (628-759) peptide from the first nickel affinity chromatography step was coated on ELISA plates (0.1 ug/ml). Plates were blocked with 10% goat serum. Dilutions of sera from infected and non-infected pigs were made in PBS with 10% goat serum, and added to the blocked plates. After incubation and washing, bound porcine antibodies were detected using biotin-labeled goat anti-swine antibody, followed by avidin-peroxidase. Peroxidase activity was detected using a chromagenic substrate.

Serum from an uninfected control pig was serially diluted from 1:10 to 1:20,480 and applied to the ELISA plates for analysis. Optical density (OD) was below 0.4 in all cases. In contrast, serum from a pig that had previously been infected with the heterologous PRRS virus isolate VR2332 about 200 days earlier reacted in a dilution-dependent manner, giving OD values in excess of 1.2 at 1:10 and 1:20 dilutions, and dropping below an OD of 0.4 only after reaching a 1:640 dilution. The VR2332 virus is quite divergent from the P129 isolate, and the 132 amino acid nsp2 (628-759) peptide from VR2332 (RPKYSAQAIIDSGGPCSGHLQEVKETCLSVMREACDATKLDDPATQEWLSRMWDRVDMLTW RNTSVYQAICTLDGRLKFLPKMILETPPPYPCEFVMMPHTPAPSVGAESDLTIGSVATEDVPRILE KIENV) (SEQ. ID NO. 65) shares only 85.6% identity with its homolog that was used in the ELISA assay. This suggests that antigenic epitopes are shared, and that an ELISA of this sort is likely to be robust enough to detect infection with most, if not all, type II ("North American" genotype) PRRS viruses. In addition, the ELISA is sensitive enough to show a strong positive reaction with serum from a pig whose antibody levels have been waning for a long period of time (200 days post infection).

Pigs vaccinated with a virus that lacks the nsp2 (628-759) peptide, due to genetic deletion, are not expected to induce antibodies to this region. It is this ability to differentiate vaccinated and naïve (negative) pigs from pigs that have been exposed to field strains of the PRRS virus (positive) that form the basis of the utility of this invention. Pigs that test positive can be removed from the herd or placed in isolation, thus aiding in the management and possible eradication of the PRRS virus.

Alternatively to the peptides disclosed above, peptides representing the corresponding region from other PRRS viruses can be employed in a diagnostic assay. Numerous examples of such peptides are provided for by the sequences disclosed in SEQ ID. NOs 66-115. That is 50 examples of similarly suitable peptides are provided by the polypeptides disclosed in SEQ ID. NOs 66-115 In addition to those examples, fragments of any of the peptides described can be used as a reagent. Fragments can be as short as ten amino acids, capable of forming and being recognized as an epitope by an antibody molecule, or as long as the entire region. For example, the peptide can comprise amino acids 1-10 of the respective 132 amino acid nsp2 peptide. The peptide can comprise amino acids 2-11 of the peptide. The peptide can comprise amino acids 3-12 of the peptide. Peptides are selected in this fashion by progressively "walking" down the amino acid sequence of the nsp2 fragment, all of the way through to amino acid 132, generating 123 possible 10-mer peptides.

In addition to 10-mer peptides, the fragment can be 11 amino acid residues in length. Beginning with a fragment comprising amino acid 1-11, and progressing to the C-terminal residue, 122 different peptides are possible for the corresponding 132 amino acid region in nsp2. Similarly, the fragment can be 12, 13, 14, 15, 16, 17, 18, 19, 20 or more residues in length, up to 131 residues in length, and such peptides are readily identifiable by beginning at residue 1 and "walking" down the amino acid sequence of the corresponding peptide. There are 7626 such fragments in a peptide of 132 amino acid residues (including the full length peptide). Such a strategy can be applied to the corresponding nsp2 sequence from any strain of PRRS virus, making it possible to have a diagnostic kit specific for that and possibly other related strains of PRRS virus.

Example XIII

Infection of Pigs with Recombinant Viruses

To establish the level of attenuation achieved by the deletion of the nsp2 (628-759) peptide, and to evaluate the ability of the deletion to serve as a serological marker, young pigs are infected with the undeleted parental virus P129-Mlu/SgrA, P129-Mlu-GFP-SgrA or P129-Mlu-HA-SgrA. Three groups of 10 conventional weaned pigs, 3 weeks of age, are housed separately. A mock-infected group (6 pigs) is included in the study, and naïve pigs (contact controls, 2 per vaccine group) are commingled with infected pigs in order to evaluate the ability of the viruses to spread. After a week of acclimation, at about 4 weeks of age, pigs are infected with the three viruses, or mock infected, by delivering 2 ml of a diluted virus stock (at $1\times10^4$ $TCID_{50}$/ml) intramuscularly and 1 ml intranasally to each nostril (total dose is $4\times10^4$ $TCID_{50}$/ml). Pigs are monitored daily for clinical signs of disease from day −3 to day 10 (general condition, (general condition, depression, loss of appetite, sneezing, coughing, and respiratory distress), and rectal temperatures are taken on day −1, 3, 7, and 10. On day 10, half of the pigs in each group (selected by prior allotment) are necropsied in order to examine lung lesions and to sample tissues for virus isolation and histopathology. The remaining pigs are necropsied on day 28. All pigs are weighed on arrival, on day −1 or 0, and at necropsy (day 10 or 28).

Blood (10 ml) is collected from all pigs on days −1 or 0, 3, 7, 10, 14, 21, and 28, into serum separator tubes. Sera are frozen at −80 C until used for the determination of anti-PRRSV antibodies (by IDEXX HerdChek ELISA), neutralizing antibodies (by serum neutralization assay), and virus isolation (titration of virus infectivity by $TCID_{50}$ assay). In addition, sera will be assayed for antibodies against the nsp2 (628-759) peptide using the ELISA described in Example XII above. Also, the induction of serum antibodies to GFP or to the HA tag can be determined using commercial kits or reagents.

The viruses with nsp2 (628-759) deleted are attenuated (less virulent) relative to the parental virus P129-Mlu/SgrA, as evidenced by a combination of one or more of the following characteristics in infected pigs: (1) reduced clinical signs, (2) reduced fever, (3) increased weight gain, (4) reduced number or severity of lung lesions, (5) increased neutralizing antibody levels, (6) decreased level or duration of viremia in serum, lung, and/or tonsil tissue, or (7) reduced spread to naïve contact control pigs. Attenuated viruses with these characteristics are useful as live vaccines.

All infected pigs test positive for anti-PRRSV antibodies using a commercial ELISA (IDEXX HerdChek), with seroconversion occurring no later than 21 days post-infection. Only those pigs infected with undeleted parental virus P129-Mlu/SgrA are expected to have antibodies specific to the nsp2 (628-759) peptide, as measured using the ELISA described in Example XII. Such a vaccine virus is useful for differentiating infected from vaccinated animals (DIVA), otherwise known as a negatively marked vaccine.

Sera from pigs infected with P129-Mlu-GFP-SgrA or P129-Mlu-HA-SgrA are assayed for antibodies to GFP and the HA tag, respectively, by detecting these antibodies using commercially available reagents and kits. Such positive serological markers or "compliance markers", when incorporated into a vaccine, are useful for determining which pigs in a herd have been successfully immunized with the vaccine. In addition, the waning of antibodies against the marker can be used as surrogate for the waning of antibodies against the PRRS virus, giving an indication of when to revaccinate.

In a separate pig study, the ability of an nsp2 (628-759)-deleted PRRS virus to function as a vaccine is tested directly. The P129-PK-dnsp2 virus (Example XI) is used to immunize 4 week old pigs by delivering 2 ml of virus at $2\times10^4$ $TCID_{50}$/ml intramuscularly. After 28 days, these pigs are challenged by infection with a virulent PRRS isolate (NADC20). The severity of the disease induced by the NADC20 virus is compared to disease induced in non-vaccinated (naïve) pigs. A useful vaccine will result in at least partial reduction of disease caused by NADC20, including clinical signs, fever, reduced weight gain, lung lesions, persistent viremia, and spread to contact control pigs.

DEPOSIT OF BIOLOGICAL MATERIALS

The following biological material was deposited with the American Type Culture Collection (ATCC) at 10801 University Blvd., Manassas, Va., 20110-2209, USA, on Nov. 19, 1998 and were assigned the following accession numbers:

| Plasmid | Accession No. |
|---|---|
| pT7P129A | 203488 |
| pCMV-S-P129 | 203489 |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention claimed is:

1. An isolated polynucleotide molecule comprising a DNA sequence encoding an infectious RNA molecule encoding a North American PRRS virus wherein said DNA sequence is SEQ ID NO:1, or a sequence that has at least 70% identity to SEQ ID NO:1, or that hybridizes to the complement of SEQ ID NO:1 under highly stringent conditions which comprise hybridization to filter bound DNA in 0.5M $NaHPO_4$, 7% SDS, 1 mM EDTA at 65° C., and washing in 0.1×SSC/0.1% SDS at 68° C., wherein said molecule lacks at least one DNA sequence encoding a detectable antigenic epitope of North American PRRS virus in the nonstructural protein 2 coding region of ORF1a within said DNA sequence, and wherein said isolated polynucleotide molecule does not comprises a nucleotide sequence, within said PRRS encoding sequence, that encodes a detectable heterologous antigenic epitope.

2. The isolated polynucleotide molecule of claim 1, wherein said molecule lacks at least one DNA sequence encoding a detectable antigenic epitope of North American PRRS virus in the hypervariable region (genomic nucleotides 2720-3980) in the nonstructural protein 2 coding region of ORF1a within said DNA sequence.

3. The isolated polynucleotide molecule of claim 2, wherein said molecule lacks at least one DNA sequence encoding a detectable antigenic epitope of North American PRRS virus between amino acids from 616 to 752 in the hypervariable region in the nonstructural protein 2 coding region of ORF1a within said DNA sequence.

4. The isolated polynucleotide molecule of claim 2, wherein said molecule lacks the DNA sequence encoding amino acids 628 and 759 in the hypervariable region in the nonstructural protein 2 coding region of ORF1a within said DNA sequence.

5. The isolated polynucleotide molecule according to claim 1 that is genetically modified such that when it infects a porcine animal it is unable to produce PRRS in the animal yet able to elicit an effective immunoprotective response against a PRRS virus in the porcine animal.

6. An isolated polynucleotide molecule according to claim 1 that is at least 75% identical to SEQ ID NO:1.

7. An isolated polynucleotide molecule according to claim 1 that is at least 85% identical to SEQ ID NO:1.

* * * * *

SEQUENCE LISTING

```
<160> NUMBER OF SEQ ID NOS: 115

<210> SEQ ID NO 1
<211> LENGTH: 15450
<212> TYPE: DNA
<213> ORGANISM: Porcine reproductive and respiratory syndrome virus

<400> SEQUENCE: 1

atgacgtata ggtgttggct ctatgccacg gcatttgtat tgtcaggagc tgtgaccatt      60

ggcacagccc aaaacttgct gcacggaaaa cgcccttctg tgacagcctt cttcagggga     120

gcttaggggt ctgtccctag caccttgctt ctggagttgc actgctttac ggtctctcca     180
```

-continued

```
cccctttaac catgtctggg atacttgatc ggtgcacgtg cacccccaat gccagggtgt    240
ttatggcgga gggccaagtc tactgcacac gatgtctcag tgcacggtct ctccttcctc    300
tgaatctcca agttcctgag cttggggtgc tgggcctatt ttataggccc gaagagccac    360
tccggtggac gttgccacgt gcattcccca ctgtcgagtg ctcccccgcc ggggcctgct    420
ggctttctgc gatctttcca attgcacgaa tgaccagtgg aaacctgaac tttcaacaaa    480
gaatggtgcg ggttgcagct gagatttaca gagccggcca actcacccct gcagttttga    540
aggctctaca agtttatgaa cggggttgtc gctggtaccc cattgtcgga cctgtccctg    600
gagtggccgt tcacgccaac tccctacatg tgagtgacaa acctttcccg ggagcaactc    660
atgtgttaac caacctaccg ctcccgcaga ggcccaagcc tgaagacttt tgcccttttg    720
agtgtgctat ggctgacgtc tatgacatta gccatgacgc cgtcatgtat gtggccagag    780
ggaaagtctc ctgggcccct cgtggcgggg atgaagtgaa atttgaaacc gtccccgaag    840
agttgaagtt gattgcgaac cgactccaca tctccttccc gccccaccac gcagtggaca    900
tgtctgagtt tgccttcata gcccctggga gtggtgtctc cttgcgggtc gagcaccaac    960
acggttgcct tcccgctgat actgtccctg aagggaactg ctggtggtgc ttgtttgact   1020
tgctcccacc ggaagttcag aataaagaaa ttcgccgtgc taaccaattt ggctatcaaa   1080
ccaagcatgg tgtccctggc aagtacctac agcggaggct gcaagttaat ggtctccgag   1140
cagtgactga tacagatgga cctattgtcg tacagtactt ctctgttagg gagagttgga   1200
tccgccactt cagactggcg gaagaaccta gcctccctgg gtttgaagac ctcctcagaa   1260
taagggtaga gcctaatacg tcgccattgg gtggcaaggg tgaaaaaatc ttccggtttg   1320
gcagtcacaa gtggtacggt gctggaaaga gagcaaggag agcacgctct ggtgcaactg   1380
ccacggtcgc tcactgcgct ttgcccgctc gcgaagccca gcaggccaag aagctcgagg   1440
ttgccagcgc caacagggct gagcatctca agtactattc cccgcctgcc gacgggaact   1500
gtggttggca ctgcatttcc gccattacca accggatggt gaattccaaa tttgaaacca   1560
ctcttcccga gagagtgaga ccttcagatg actgggctac tgacgaggat cttgtgaata   1620
ccatccaaat cctcaggctc cccgcggcct tggacaggaa cggtgcttgt gctggcgcca   1680
agtacgtgct caagctggaa ggtgagcact ggaccgtctc tgtgacccct gggatgaccc   1740
cttctttgct ccccccttgaa tgtgttcagg gttgttgtga gcataagagc ggtcttggtt   1800
tcccagacgt ggtcgaagtt tccggatttg accctgcctg tcttgaccga cttgctgaga   1860
taatgcactt acctagcagt gtcatcccag ctgctctggc cgagatgtcc gacgacttca   1920
atcgtctggc ttccccggcc gccactgtgt ggactgtttc gcaattcttt gcccgccaca   1980
gaggaggaga gcatcctgac caggtgtgct tagggaaaat tatcaacctt tgtcaggtga   2040
ttgaggaatg ctgctgttcc cggaacaaag ccaaccgggc taccccggaa gaggttgcgg   2100
caaaagttga ccagtacctc cgtggtgcag caagccttgg agaatgcttg gccaagcttg   2160
agagggctcg cccgccgagc gcgatggaca cctcctttga ttggaatgtt gtgcttcctg   2220
gggttgagac ggcggatcag acaaccaaac agctccatgt caaccagtgc cgcgctctgg   2280
ttcctgtcgt gactcaagag cctttggaca gagactcggt ccctctgacc gccttctcgc   2340
tgtccaattg ctactaccct gcacaaggtg acgaggtccg tcaccgtgag aggctaaact   2400
ccgtgctctc taagttggag ggggttgttc gtgaggaata tgggctcacg ccaactggac   2460
ctggcccgcg acccgcactg ccgaacgggc tcgacgagct taaagaccag atggaggagg   2520
atctgctgaa attagtcaac gcccaggcaa cttcagaaat gatggcctgg gcagccgagc   2580
```

```
aggttgatct aaaagcttgg gtcaaaaatt acccacggtg gacaccgcca cccccctccac   2640
caagagttca gcctcgaaaa acgaagtctg tcaagagctt gctagagaac aagcctgtcc   2700
ctgctccgcg caggaaggtc agatctgatt atggcagccc gattttgatg ggcgacaatg   2760
ttcctaacgg ttgggaagat tcgactgttg gtggtcccct tgacctttcg gcaccatccg   2820
agccgatgac acctctgagt gagcctgtac ttatttccag gccagtgaca tctttgagtg   2880
tgccggcccc agttcctgca ccgcgtagag ctgtgtctcg accgatgacg ccctcgagtg   2940
agccaatttt tgtgtctgca ctgcgacaca aatttcagca ggtggaaaaa gcaaatctgg   3000
cggcagcagc gccgatgtac caggacgaac ccttagattt gtctgcatcc tcacagactg   3060
aatatggggc ttctcccccta acaccaccgc agaacgtggg cattctggag gtaagggggc   3120
aagaagctga ggaagttctg agtgaaatct cggatattct gaatgatacc aaccctgcac   3180
ctgtgtcatc aagcagctcc ctgtcaagtg ttaggatcac acgcccaaaa tactcagctc   3240
aagccattat cgacttgggc gggccctgca gtgggcacct ccaaagggaa aaagaagcat   3300
gcctccgcat catgcgtgag gcttgtgatg cggccaagct tagtgaccct gccacgcagg   3360
aatggctttc tcgcatgtgg gatagggtgg acatgctgac ttggcgcaac acgtctgctt   3420
accaggcgtt tcgcacctta gatggcaggt ttgggtttct cccaaagatg atactcgaga   3480
cgccgccgcc ctacccgtgt gggtttgtga tgttgcctca caccccctgca ccttccgtga   3540
gtgcagagag cgaccttacc atcggttcag tcgccactga agatattcca cgcatcctcg   3600
ggaaaataga aaataccggt gagatgatca accagggacc cttggcatcc tctgaggaag   3660
aaccggtata caaccaacct gccaaagact cccggatatc gtcgcggggg tctgacgaga   3720
gcacagcagc tccgtccgca ggtacaggtg gcgccggctt atttactgat ttgccacctt   3780
cagacggcgt agatgcggac ggtgggggc cgttgcagac ggtaagaaag aaagctgaaa   3840
ggctcttcga ccaattgagc cgtcaggttt ttaacctcgt ctcccatctc cctgttttct   3900
tctcacacct cttcaaatct gacagtggtt attctccggg tgattggggt tttgcagctt   3960
ttactctatt ttgcctcttt ttgtgttaca gctacccatt cttcggtttc gttcccctct   4020
tgggtgtatt ttctgggtct tctcggcgtg tgcgcatggg ggtttttggc tgctggctgg   4080
cttttgctgt tggcctgttc aagcctgtgt ccgacccagt cggcactgct tgtgagtttg   4140
actcgccaga gtgtaggaac gtccttcatt cttttgagct tctcaaacct tgggaccctg   4200
ttcgcagcct tgttgtgggc cccgtcggtc tcggtcttgc cattcttggc aggttactgg   4260
gcggggcacg ctacatctgg catttttttgc ttaggcttgg cattgttgca gattgtatct   4320
tggctggagc ttatgtgctt tctcaaggta ggtgtaaaaa gtgctgggga tcttgtataa   4380
gaactgctcc taatgaaatc gccttcaacg tgttcccttt tacacgtgcg accaggtcgt   4440
cactcatcga cctgtgcgat cggttttgtg cgccaaaagg catggacccc attttcctcg   4500
ccactgggtg gcgtgggtgc tggaccggcc gaagtcccat tgagcaaccc tctgaaaaac   4560
ccatcgcgtt cgcccagttg gatgaaaaga ggattacggc tagaactgtg gtcgctcagc   4620
cttatgatcc taatcaagcc gtaaagtgct tgcgggtgtt acaggcgggt ggggcgatgg   4680
tggccgaggc agtcccaaaa gtggtcaaag tttctgctat tccattccga gcccccctttt   4740
ttcccaccgg agtgaaagtt gatcccgagt gcaggatcgt ggtcgacccc gatactttta   4800
ctacagccct ccggtctggt tactctacca caaacctcgt ccttggtgtg ggggactttg   4860
cccagctgaa tggactaaag atcaggcaaa tttccaagcc ttcgggagga ggcccacacc   4920
tcattgctgc cctgcatgtt gcctgctcga tggcgttgca catgcttgct ggggtttatg   4980
```

-continued taacttcagt ggggtcttgc ggtgccggca ccaacgatcc atggtgcact aatccgtttg 5040
ccgttcctgg ctacggacca ggctctctct gcacgtccag attgtgcatc tcccaacatg 5100
gccttaccct gcccttgaca gcacttgtgg cgggattcgg tcttcaggaa atcgccttgg 5160
tcgttttgat tttcgtttcc atcggaggca tggctcatag gttgagttgt aaggctgata 5220
tgctgtgcat cttacttgca atcgccagct atgtttgggt accccttacc tggttgcttt 5280
gtgtgtttcc ttgttggttg cgctggttct ctttgcaccc cctcaccatc ctatggttgg 5340
tgtttttctt gatttctgta aatatgcctt cgggaatctt ggccgtggtg ttattggttt 5400
ctctttggct tttgggacgt tatactaaca ttgctggtct tgtcaccccc tatgatattc 5460
atcattacac cagtggcccc cgcggtgttg ccgccttagc taccgcacca gatggaacct 5520
acttggctgc cgtccgccgc gctgcgttga ctggtcgcac catgctgttc accccgtctc 5580
agcttgggtc ccttcttgag ggcgctttca gaactcgaaa gccctcactg aacaccgtca 5640
atgtggttgg gtcctccatg ggctctggtg gagtgttcac catcgacggg aaaattaggt 5700
gcgtgactgc cgcacatgtc cttacgggta attcggctag ggtttccgga gtcggcttca 5760
atcaaatgct tgactttgat gtgaaagggg acttcgccat agctgattgc ccgaattggc 5820
aaggagctgc tcccaagacc caattctgcg aggatggatg ggctggccgt gcctattggc 5880
tgacatcctc tggcgtcgaa cccggtgtta ttgggaatgg attcgccttc tgcttcaccg 5940
cgtgcggcga ttccgggtcc ccagtgatca ccgaagctgg tgagcttgtc ggcgttcaca 6000
caggatcaaa taaacaagga ggtggcatcg tcacgcgccc ttcaggccag ttttgtaacg 6060
tggcacccat caagctgagc gaattaagtg aattctttgc tggacccaag gtcccgctcg 6120
gtgatgtgaa ggttggcagc cacataatta aagatacgtg cgaagtacct tcagatcttt 6180
gcgccttgct tgctgccaaa cctgaactgg agggaggcct ctccaccgtc caacttctgt 6240
gtgtgttttt cctactgtgg agaatgatgg gacatgcctg gacgcccttg gttgctgtgg 6300
ggtttttcat tctgaatgag gttctcccag ctgtcctggt tcggagtgtt ttctcctttg 6360
ggatgtttgt gctatcttgg ctcacaccat ggtctgcgca agttctgatg atcaggcttc 6420
taacagcagc tcttaacagg aacagatggt cacttgcctt ttacagcctt ggtgcggtga 6480
ccggttttgt cgcagatctt gcggcaactc aagggcaccc gttgcaggca gtaatgaatt 6540
tgagcaccta tgccttcctg cctcggatga tggttgtgac ctcaccagtc ccagtgattg 6600
cgtgtggtgt tgtgcaccta cttgccatca ttttgtactt gttcaagtac cgcggcctgc 6660
acaatgttct tgttggtgat ggagcgtttt ctgcagcttt cttcttgcga tactttgccg 6720
agggaaagtt gagggaaggg gtgtcgcaat cctgcggaat gaatcatgag tcattaactg 6780
gtgccctcgc tatgagactc aatgacgagg acttggactt ccttacgaaa tggactgatt 6840
ttaagtgctt tgtttctgcg tccaacatga ggaatgcagc aggccaattc atcgaggctg 6900
cctatgcaaa agcacttaga attgaacttg cccagttggt gcaggttgat aaggttcgag 6960
gtactttggc caagcttgag gcttttgctg ataccgtggc accccaactc tcgcccggtg 7020
acattgttgt tgctcttggc catacgcctg ttggcagcat cttcgaccta aaggttggtg 7080
gtaccaagca tactctccaa gtcattgaga ccagagtcct tgccgggtcc aaaatgaccg 7140
tggcgcgcgt cgttgaccca acccccacgc ccccacccgc acccgtgccc atcccccctcc 7200
caccgaaagt tctagagaat ggtcccaacg cctgggggga tggggaccgt ttgaataaga 7260
agaagaggcg taggatggaa accgtcggca tctttgtcat gggtgggaag aagtaccaga 7320
aattttggga caagaattcc ggtgatgtgt tttacgagga ggtccatgac aacacagatg 7380

```
cgtgggagtg cctcagagtt ggtgaccctg ccgactttga ccctgagaag ggaactctgt   7440
gtgggcatac tactattgaa gataaggatt acaaagtcta cgcctcccca tctggcaaga   7500
agttcctggt ccccgtcaac tcagagagcg gaagagccca atgggaagct gcaaagcttt   7560
ccgtggagca ggcccttggc atgatgaatg tcgacggtga actgacggcc aaagaagtgg   7620
agaaactgaa aagaataatt gacaaacttc agggcctgac taaggagcag tgtttaaact   7680
gctagccgcc agcggcttga cccgctgtgg tcgcggcggc ttggttgtta ctgagacagc   7740
ggtaaaaata gtcaaatttc acaaccggac tttcacccta gggcctgtga atttaaaagt   7800
ggccagtgag gttgagctga aagacgcggt cgagcacaac caacacccgg ttgcaagacc   7860
ggttgacggt ggtgttgtgc tcctgcgttc cgcagttcct tcgcttatag atgtcctgat   7920
ctccggtgct gacgcatctc ctaagttact cgctcgtcac gggccgggga acactgggat   7980
cgatggcacg ctttgggact ttgaggccga ggccaccaaa gaggaaattg cactcagtgc   8040
gcaaataata caggcttgtg acattaggcg cggcgacgca cctgaaattg gtctccctta   8100
caagctgtac cctgttaggg gcaaccctga gcgggtaaaa ggagttttac agaatacaag   8160
gtttggagac ataccttaca aaacccccag tgacactgga agcccagtgc acgcggctgc   8220
ctgcctcacg cccaatgcca ctccggtgac tgatgggcgc tctgtcttgg ctactaccat   8280
gccctccggt tttgaattgt atgtaccgac cattccagcg tctgtccttg attatcttga   8340
ctctaggcct gactgcccca aacagttgac agagcacggc tgtgaggatg ccgcattgag   8400
agacctctcc aagtatgact tgtccaccca aggctttgtt ttacctgggg ttcttcgcct   8460
tgtgcgtaag tacctgtttg cccatgtggg taagtgcccg cccgttcatc ggccttccac   8520
ttaccctgcc aagaattcta tggctggaat aaatgggaac aggtttccaa ccaaggacat   8580
tcagagcgtc cctgaaatcg acgttctgtg cgcacaggcc gtgcgagaaa actggcaaac   8640
tgttacccct tgtaccctca agaaacagta ttgtgggaag aagaagacta ggacaatact   8700
cggcaccaat aatttcattg cgttggccca ccgggcagcg ttgagtggtg tcacccaggg   8760
cttcatgaaa aaggcgttta actcgcccat cgccctcggg aaaaacaaat ttaaggagct   8820
acagactccg gtcttaggca ggtgccttga agctgatctt gcatcctgtg atcgatccac   8880
acctgcaatt gtccgctggt ttgccgccaa tcttctttat gaacttgcct gtgctgaaga   8940
gcacctaccg tcgtacgtgc tgaactgctg ccatgaccta ttggtcacgc agtccggcgc   9000
agtgactaag aggggtggcc tatcgtctgg cgacccgatc acttctgtgt ctaacaccat   9060
ttacagcttg gtgatatatg cacagcacat ggtgcttagt tactttaaaa gtggtcaccc   9120
tcatggcctt ctgttcctac aagaccagct gaagttcgag gacatgctca aagtccaacc   9180
cctgatcgtc tattcggacg acctcgtgct gtatgccgaa tctcccacca tgccgaacta   9240
ccactggtgg gtcgaacatc tgaatttgat gctgggtttt cagacggacc caaagaagac   9300
agccataacg gactcgccat catttctagg ctgtaggata ataaatggac gccagctagt   9360
ccccaaccgt gacaggatcc tcgcggccct cgcttaccat atgaaggcaa gcaatgtttc   9420
tgaatactac gccgcggcgg ctgcaatact catggacagc tgtgcttgtt tagagtatga   9480
tcctgaatgg tttgaagagc ttgtggttgg gatagcgcag tgcgcccgca aggacggcta   9540
cagctttccc ggcccgccgt tcttcttgtc catgtgggaa aaactcagat ccaatcatga   9600
ggggaagaag tccagaatgt gcgggtattg cggggccccg gctccgtacg ccactgcctg   9660
tggcctcgac gtctgtattt accacaccca cttccaccag cattgtccag tcataatctg   9720
gtgtggccac ccggctggtt ctggttcttg tagtgagtgc aaaccccccc tagggaaagg   9780
```

-continued

```
cacaagccct ctagatgagg tgttagaaca agtcccgtat aagcctccac ggactgtaat   9840
catgcatgtg gagcagggtc tcacccctct tgacccaggc agataccaga ctcgccgcgg   9900
attagtctcc gttaggcgtg gcatcagagg aaacgaagtt gacctaccag acggtgatta   9960
tgctagcacc gccctactcc ccacttgtaa agagatcaac atggtcgctg tcgcctctaa  10020
tgtgttgcgc agcaggttca tcatcggtcc gcccggtgct gggaaaacat actggctcct  10080
tcagcaggtc caggatggtg atgtcattta cacaccgact caccagacca tgctcgacat  10140
gattagggct ttggggacgt gccggttcaa cgtcccagca ggtacaacgc tgcaattccc  10200
tgccccctcc cgtaccggcc cgtgggttcg catcctggcc ggcggttggt gtcctggtaa  10260
gaattccttc ctggatgaag cagcgtattg taatcacctt gatgtcttga ggctccttag  10320
caaaaccacc cttacctgtc tgggagactt caaacaactc cacccagtgg gttttgattc  10380
tcattgctat gtttttgaca tcatgcctca gacccagttg aagaccatct ggagattcgg  10440
acagaacatc tgtgatgcca tccaaccaga ttacagggac aaacttgtgt ccatggtcaa  10500
cacaacccgt gtaacctaca tggaaaaacc tgtcaagtat gggcaagtcc tcacccctta  10560
ccacagggac cgagaggacg gcgccatcac aattgactcc agtcaaggcg ccacatttga  10620
tgtggttaca ctgcatttgc ccactaaaga ttcactcaac aggcaaagag cccttgttgc  10680
tatcaccagg gcaagacatg ctatctttgt gtatgaccca cacaggcaat tgcagagcat  10740
gtttgatctt cctgcgaagg gcacacccgt caacctcgca gtgcaccgtg atgagcagct  10800
gatcgtactg gatagaaata ataaagaatg cacagttgct caggctatag gcaacggaga  10860
taaattcagg gccaccgaca agcgcgttgt agattctctc cgcgccattt gtgctgatct  10920
ggaagggtcg agctccccgc tccccaaggt cgcacacaac ttgggatttt atttctcacc  10980
tgatttgaca cagtttgcta aactcccggt agaccttgca ccccactggc ccgtggtgac  11040
aacccagaac aatgaaaagt ggccggatcg gctggttgcc agccttcgcc ctgtccataa  11100
gtatagccgt gcgtgcattg gtgccggcta tatggtgggc ccctcggtgt ttctaggcac  11160
ccctggggtc gtgtcatact acctcacaaa atttgtcaag ggcgaggctc aagtgcttcc  11220
ggagacagtc ttcagcaccg gccgaattga ggtggattgc cgggagtatc ttgatgacag  11280
ggagcgagaa gttgctgagt ccctcccaca tgccttcatt ggcgacgtca aaggcaccac  11340
cgttgggggga tgtcatcatg tcacctccaa ataccttccg cgcttccttc ccaaggaatc  11400
agtcgcggta gtcggggttt cgagccccgg gaaagccgca aaagcagtgt gcacattgac  11460
ggatgtgtac ctcccagacc ttgaggccta cctccaccca gagactcagt ctaagtgctg  11520
gaaagttatg ttggacttca aggaagttcg actgatggtc tggaaagaca agacggccta  11580
tttccaactt gaaggccgct atttcacctg gtatcagctt gcaagctacg cctcgtacat  11640
ccgtgttcct gtcaactcca cggtgtatct ggacccctgc atgggccctg ccctttgcaa  11700
cagaagagtt gtcgggtcca cccattgggg agctgacctc gcagtcaccc cttatgatta  11760
cggtgctaaa atcatcttgt ctagcgctta ccatggtgaa atgcctcctg gatacaagat  11820
tctggcgtgc gcggagttct cgctcgacga cccagtcaag tacaaacaca cctggggttt  11880
tgaatcggat acagcgtatc tgtatgagtt caccggaaac ggtgaggact gggaggatta  11940
caatgatgcg tttcgtgcgc gccagaaagg gaaaatttat aaggccactg ctaccagcat  12000
gaagttttat tttcccccgg gccccgtcat tgaaccaact ttaggcctga attgaaatga  12060
aatggggtct atacaaagcc tcttcgacaa aattggccag ctttttgtgg atgctttcac  12120
ggaatttttg gtgtccattg ttgatatcat catatttttg gccattttgt ttggcttcac  12180
```

-continued

```
catcgccggt tggctggtgg tcttttgcat cagattggtt tgctccgcgg tattccgtgc  12240
gcgccctgcc attcaccctg agcaattaca gaagatccta tgaggccttt ctttctcagt  12300
gccgggtgga cattcccacc tggggggtaa aacacccttt ggggatgttt tggcaccata  12360
aggtgtcaac cctgattgat gaaatggtgt cgcgtcgaat gtaccgcatc atggaaaaag  12420
cagggcaagc tgcctggaaa caggtggtga gcgaggctac gctgtctcgc attagtagtt  12480
tggatgtggt ggctcatttt caacatcttg ccgccattga agccgagacc tgtaaatatt  12540
tggcttctcg actgcccatg ctacacaacc tgcgcatgac agggtcaaat gtaaccatag  12600
tgtataatag cactttaaat caggtgtttg ctatttttcc aacccctggt tcccggccaa  12660
agcttcatga ttttcagcaa tggctaatag ctgtacattc ctccatattt tcctctgttg  12720
cagcttcttg tactcttttt gttgtgctgt ggttgcgggt tccaatgcta cgtactgttt  12780
ttggtttccg ctggttaggg gcaatttttc tttcgaactc atggtgaatt acacggtgtg  12840
tccaccttgc ctcacccgac aagcagccgc tgaggtcctt gaacccggta ggtctctttg  12900
gtgcaggata gggcatgacc gatgtgggga ggacgatcac gacgaactag ggttcatggt  12960
tccgcctggc ctctccagcg aaagccactt gaccagtgtt tacgcctggt tggcgttcct  13020
gtccttcagc tacacggccc agttccatcc cgagatattt gggataggga acgtgagtga  13080
agtttatgtt gacatcaagc accaattcat ctgcgccgtt catgacgggc agaacaccac  13140
cttgcctcgc catgacaata tttcagccgt atttcagacc tactatcaac atcaggtcga  13200
cggcggcaat tggtttcacc tagaatggct gcgtcccttc ttttcctctt ggttggtttt  13260
aaatgtttcg tggtttctca ggcgttcgcc tgcaagccat gtttcagttc gagtctttca  13320
gacatcaaaa ccaacactac cgcagcatca ggctttgttg tcctccagga catcagctgc  13380
cttaggcatg gcgactcgtc ctttccgacg attcgcaaaa gctctcaatg ccgcacggcg  13440
atagggacac ccgtgtatat caccatcaca gccaatgtga cagatgagaa ttacttacat  13500
tcttctgatc tcctcatgct ttcttcttgc cttttctatg cttctgagat gagtgaaaag  13560
ggattcaagg tggtgtttgg caatgtgtca ggcatcgtgg ctgtgtgtgt caactttacc  13620
agctacgtcc aacatgtcaa agagtttacc caacgctcct tggtggtcga tcatgtgcgg  13680
ctgcttcatt tcatgacacc tgagaccatg aggtgggcaa ccgttttagc ctgtcttttt  13740
gccatcctac tggcaatttg aatgttcaag tatgttgggg aaatgcttga ccgcgggctg  13800
ttgctcgcga ttgctttctt tgtggtgtat cgtgccgttc tgttttgctg tgctcggcag  13860
cgccaacagc agcagcagct ctcattttca gttgatttat aacttgacgc tatgtgagct  13920
gaatggcaca gattggctgg cagaaaaatt tgattgggca gtggagactt ttgtcatctt  13980
tcccgtgttg actcacattg tttcctatgg tgcactcacc accagccatt tccttgacac  14040
agttggtctg gttactgtgt ccaccgccgg gttttatcac gggcggtatg tcttgagtag  14100
catctacgcg gtctgtgctc tggctgcgtt gatttgcttc gttattaggc ttgcgaagaa  14160
ctgcatgtcc tggcgctact cttgtaccag atataccaac ttccttctgg acactaaggg  14220
cagactctat cgttggcggt cgcccgttat catagaaaaa gggggtaagg ttgaggtcga  14280
aggtcacctg atcgacctca aaagagttgt gcttgatggt tccgtggcaa ccccttttaac  14340
cagagtttca gcggaacaat ggggtcgtct ctagacgact tttgccatga tagcacggct  14400
ccacaaaagg tgcttttggc gttttccatt acctacacgc cagtaatgat atatgctcta  14460
aaggtaagtc gcggccgact actagggctt ctgcaccttt tgatctttct gaattgtgct  14520
tttaccttcg ggtacatgac attcgagcac tttcagagca caaatagggt cgcgctcact  14580
```

atgggagcag tagttgcact tctttggggg gtgtactcag ccatagaaac ctggaaattc 14640
atcacctcca gatgccgttt gtgcttgcta ggccgcaagt acattctggc ccctgcccac 14700
cacgtcgaaa gtgccgcggg ctttcatccg attgcggcaa atgataacca cgcatttgtc 14760
gtccggcgtc ccggctccac tacggttaac ggcacattgg tgcccgggtt gaaaagcctc 14820
gtgttgggtg gcagaaaagc tgttaaacag ggagtggtaa accttgtcaa atatgccaaa 14880
taacaacggc aagcagcaaa agaaaaagaa ggggaatggc cagccagtca atcagctgtg 14940
ccagatgctg ggtaaaatca tcgcccagca aaaccagtcc agaggcaagg gaccgggcaa 15000
gaaaagtaag aagaaaaacc cggagaagcc ccattttcct ctagcgaccg aagatgacgt 15060
caggcatcac ttcacccctg gtgagcggca attgtgtctg tcgtcgatcc agactgcctt 15120
taaccagggc gctggaactt gtaccctgtc agattcaggg aggataagtt acactgtgga 15180
gtttagtttg ccgacgcatc atactgtgcg cctgatccgc gtcacagcat caccctcagc 15240
atgatgggct ggcattcttt aggcacctca gtgtcagaat tggaagaatg tgtggtggat 15300
ggcactgatt gacattgtgc ctctaagtca cctattcaat tagggcgacc gtgtgggggt 15360
aaaatttaat tggcgagaac catgcggccg caattaaaaa aaaaaaaaaa aaaaaaaaaa 15420
aaaaaaaaaa aaaaaaaaaa aaaaaaaaaa 15450

<210> SEQ ID NO 2
<211> LENGTH: 7494
<212> TYPE: DNA
<213> ORGANISM: Porcine reproductive and respiratory syndrome virus

<400> SEQUENCE: 2
atgtctggga tacttgatcg gtgcacgtgc acccccaatg ccagggtgtt tatggcggag 60
ggccaagtct actgcacacg atgtctcagt gcacggtctc tccttcctct gaatctccaa 120
gttcctgagc ttggggtgct gggcctattt tataggcccg aagagccact ccggtggacg 180
ttgccacgtg cattccccac tgtcgagtgc tcccccgccg gggcctgctg gctttctgcg 240
atctttccaa ttgcacgaat gaccagtgga aacctgaact ttcaacaaag aatggtgcgg 300
gttgcagctg agatttacag agccggccaa ctcacccctg cagttttgaa ggctctacaa 360
gtttatgaac ggggttgtcg ctggtacccc attgtcggac ctgtccctgg agtggccgtt 420
cacgccaact ccctacatgt gagtgacaaa cctttcccgg gagcaactca tgtgttaacc 480
aacctaccgc tcccgcagag gcccaagcct gaagactttt gcccttttga gtgtgctatg 540
gctgacgtct atgacattag ccatgacgcc gtcatgtatg tggccagagg gaaagtctcc 600
tgggcccctc gtggcgggga tgaagtgaaa tttgaaaccg tccccgaaga gttgaagttg 660
attgcgaacc gactccacat ctccttcccg ccccaccacg cagtggacat gtctgagttt 720
gccttcatag cccctgggag tggtgtctcc ttgcgggtcg agcaccaaca cggttgcctt 780
cccgctgata ctgtccctga agggaactgc tggtggtgct tgtttgactt gctcccaccg 840
gaagttcaga ataaagaaat tcgccgtgct aaccaatttg gctatcaaac caagcatggt 900
gtccctggca agtacctaca gcggaggctg caagttaatg gtctccgagc agtgactgat 960
acagatggac ctattgtcgt acagtacttc tctgttaggg agagttggat ccgccacttc 1020
agactggcgg aagaacctag cctccctggg tttgaagacc tcctcagaat aagggtagag 1080
cctaatacgt cgccattggg tggcaagggt gaaaaaatct tccggtttgg cagtcacaag 1140
tggtacggtg ctggaaagag agcaaggaga gcacgctctg gtgcaactgc cacggtcgct 1200
cactgcgctt tgcccgctcg cgaagcccag caggccaaga agctcgaggt tgccagcgcc 1260
aacagggctg agcatctcaa gtactattcc ccgcctgccg acgggaactg tggttggcac 1320
tgcatttccg ccattaccaa ccggatggtg aattccaaat ttgaaaccac tcttcccgag 1380
agagtgagac cttcagatga ctgggctact gacgaggatc ttgtgaatac catccaaatc 1440
ctcaggctcc ccgcggcctt ggacaggaac ggtgcttgtg ctggcgccaa gtacgtgctc 1500
aagctggaag gtgagcactg gaccgtctct gtgacccctg ggatgacccc ttctttgctc 1560
ccccttgaat gtgttcaggg ttgttgtgag cataagagcg gtcttggttt cccagacgtg 1620
gtcgaagttt ccggatttga ccctgcctgt cttgaccgac ttgctgagat aatgcactta 1680
cctagcagtg tcatcccagc tgctctggcc gagatgtccg acgacttcaa tcgtctggct 1740
tccccggccg ccactgtgtg gactgtttcg caattctttg cccgccacag aggaggagag 1800
catcctgacc aggtgtgctt agggaaaatt atcaaccttt gtcaggtgat tgaggaatgc 1860
tgctgttccc ggaacaaagc caaccgggct accccggaag aggttgcggc aaaagttgac 1920
cagtacctcc gtggtgcagc aagccttgga gaatgcttgg ccaagcttga gagggctcgc 1980
ccgccgagcg cgatggacac ctcctttgat tggaatgttg tgcttcctgg ggttgagacg 2040
gcggatcaga caaccaaaca gctccatgtc aaccagtgcc gcgctctggt tcctgtcgtg 2100
actcaagagc ctttggacag agactcggtc cctctgaccg ccttctcgct gtccaattgc 2160
tactaccctg cacaaggtga cgaggtccgt caccgtgaga ggctaaactc cgtgctctct 2220
aagttggagg gggttgttcg tgaggaatat gggctcacgc caactggacc tggcccgcga 2280
cccgcactgc cgaacgggct cgacgagctt aaagaccaga tggaggagga tctgctgaaa 2340
ttagtcaacg cccaggcaac ttcagaaatg atggcctggg cagccgagca ggttgatcta 2400
aaagcttggg tcaaaaatta cccacggtgg acaccgccac cccctccacc aagagttcag 2460
cctcgaaaaa cgaagtctgt caagagcttg ctagagaaca agcctgtccc tgctccgcgc 2520
aggaaggtca gatctgatta tggcagcccg attttgatgg gcgacaatgt tcctaacggt 2580
tgggaagatt cgactgttgg tggtcccctt gacctttcgg caccatccga gccgatgaca 2640
cctctgagtg agcctgtact tatttccagg ccagtgacat ctttgagtgt gccggcccca 2700
gttcctgcac cgcgtagagc tgtgtctcga ccgatgacgc cctcgagtga gccaattttt 2760
gtgtctgcac tgcgacacaa atttcagcag gtggaaaaag caaatctggc ggcagcagcg 2820
ccgatgtacc aggacgaacc cttagatttg tctgcatcct cacagactga atatggggct 2880
tctcccctaa caccaccgca gaacgtgggc attctggagg taagggggca agaagctgag 2940
gaagttctga gtgaaatctc ggatattctg aatgatacca accctgcacc tgtgtcatca 3000
agcagctccc tgtcaagtgt taggatcaca cgcccaaaat actcagctca agccattatc 3060
gacttgggcg ggccctgcag tgggcacctc caaagggaaa aagaagcatg cctccgcatc 3120
atgcgtgagg cttgtgatgc ggccaagctt agtgaccctg ccacgcagga atggctttct 3180
cgcatgtggg atagggtgga catgctgact tggcgcaaca cgtctgctta ccaggcgttt 3240
cgcaccttag atggcaggtt tgggtttctc ccaaagatga tactcgagac gccgccgccc 3300
tacccgtgtg ggtttgtgat gttgcctcac acccctgcac cttccgtgag tgcagagagc 3360
gaccttacca tcggttcagt cgccactgaa gatattccac gcatcctcgg gaaaatagaa 3420
aataccggtg agatgatcaa ccagggaccc ttggcatcct ctgaggaaga accggtatac 3480
aaccaacctg ccaaagactc ccggatatcg tcgcgggggt ctgacgagag cacagcagct 3540
ccgtccgcag gtacaggtgg cgccggctta tttactgatt tgccaccttc agacggcgta 3600
gatgcggacg gtggggggcc gttgcagacg gtaagaaaga aagctgaaag gctcttcgac 3660
caattgagcc gtcaggtttt taacctcgtc tcccatctcc ctgttttctt ctcacacctc 3720
ttcaaatctg acagtggtta ttctccgggt gattggggtt ttgcagcttt tactctattt 3780
tgcctctttt tgtgttacag ctacccattc ttcggtttcg ttcccctctt gggtgtattt 3840
tctgggtctt ctcggcgtgt gcgcatgggg gtttttggct gctggctggc ttttgctgtt 3900
ggcctgttca agcctgtgtc cgacccagtc ggcactgctt gtgagtttga ctcgccagag 3960
tgtaggaacg tccttcattc ttttgagctt ctcaaacctt gggaccctgt tcgcagcctt 4020
gttgtgggcc ccgtcggtct cggtcttgcc attcttggca ggttactggg cggggcacgc 4080
tacatctggc atttttgct taggcttggc attgttgcag attgtatctt ggctggagct 4140
tatgtgcttt ctcaaggtag gtgtaaaaag tgctggggat cttgtataag aactgctcct 4200
aatgaaatcg ccttcaacgt gttccctttt acacgtgcga ccaggtcgtc actcatcgac 4260
ctgtgcgatc ggttttgtgc gccaaaaggc atggacccca ttttcctcgc cactgggtgg 4320
cgtgggtgct ggaccggccg aagtcccatt gagcaaccct ctgaaaaacc catcgcgttc 4380
gcccagttgg atgaaaagag gattacggct agaactgtgg tcgctcagcc ttatgatcct 4440
aatcaagccg taaagtgctt gcgggtgtta caggcgggtg ggcgatggt ggccgaggca 4500 gtcccaaaag tggtcaaagt ttctgctatt ccattccgag ccccctttt tcccaccgga 4560 gtgaaagttg atcccgagtg caggatcgtg gtcgaccccg atacttttac tacagccctc 4620
cggtctggtt actctaccac aaacctcgtc cttggtgtgg gggactttgc ccagctgaat 4680
ggactaaaga tcaggcaaat ttccaagcct tcgggaggag gcccacacct cattgctgcc 4740
ctgcatgttg cctgctcgat ggcgttgcac atgcttgctg ggtttatgt aacttcagtg 4800 gggtcttgcg gtgccggcac caacgatcca tggtgcacta atccgtttgc cgttcctggc 4860
tacggaccag gctctctctg cacgtccaga ttgtgcatct cccaacatgg ccttaccctg 4920
cccttgacag cacttgtggc gggattcggt cttcaggaaa tcgccttggt cgttttgatt 4980
ttcgtttcca tcggaggcat ggctcatagg ttgagttgta aggctgatat gctgtgcatc 5040
ttacttgcaa tcgccagcta tgtttgggta ccccttacct ggttgctttg tgtgtttcct 5100
tgttggttgc gctggttctc tttgcacccc ctcaccatcc tatggttggt gtttttcttg 5160
atttctgtaa atatgccttc gggaatcttg gccgtggtgt tattggtttc tctttggctt 5220
ttgggacgtt atactaacat tgctggtctt gtcacccct atgatattca tcattacacc 5280
agtggccccc gcggtgttgc cgccttagct accgcaccag atggaaccta cttggctgcc 5340
gtccgccgcg ctgcgttgac tggtcgcacc atgctgttca ccccgtctca gcttgggtcc 5400
cttcttgagg gcgctttcag aactcgaaag ccctcactga acaccgtcaa tgtggttggg 5460
tcctccatgg gctctggtgg agtgttcacc atcgacggga aaattaggtg cgtgactgcc 5520
gcacatgtcc ttacgggtaa ttcggctagg gtttccggag tcggcttcaa tcaaatgctt 5580
gactttgatg tgaaagggga cttcgccata gctgattgcc cgaattggca aggagctgct 5640
cccaagaccc aattctgcga ggatggatgg gctggccgtg cctattggct gacatcctct 5700
ggcgtcgaac ccggtgttat tgggaatgga ttcgccttct gcttcaccgc gtgcggcgat 5760
tccgggtccc cagtgatcac cgaagctggt gagcttgtcg gcgttcacac aggatcaaat 5820
aaacaaggag gtggcatcgt cacgcgccct tcaggccagt tttgtaacgt ggcacccatc 5880
aagctgagcg aattaagtga attctttgct ggacccaagg tcccgctcgg tgatgtgaag 5940
gttggcagcc acataattaa agatacgtgc gaagtacctt cagatctttg cgccttgctt 6000
gctgccaaac ctgaactgga gggaggcctc tccaccgtcc aacttctgtg tgtgtttttc 6060
ctactgtgga gaatgatggg acatgcctgg acgcccttgg ttgctgtggg gtttttcatt 6120
ctgaatgagg ttctcccagc tgtcctggtt cggagtgttt tctcctttgg gatgtttgtg 6180
ctatcttggc tcacaccatg gtctgcgcaa gttctgatga tcaggcttct aacagcagct 6240
cttaacagga acagatggtc acttgccttt tacagccttg gtgcggtgac cggttttgtc 6300
gcagatcttg cggcaactca agggcacccg ttgcaggcag taatgaattt gagcacctat 6360
gccttcctgc ctcggatgat ggttgtgacc tcaccagtcc cagtgattgc gtgtggtgtt 6420
gtgcacctac ttgccatcat tttgtacttg ttcaagtacc gcggcctgca caatgttctt 6480
gttggtgatg gagcgttttc tgcagctttc ttcttgcgat actttgccga gggaaagttg 6540
agggaagggg tgtcgcaatc ctgcggaatg aatcatgagt cattaactgg tgccctcgct 6600
atgagactca atgacgagga cttggacttc cttacgaaat ggactgattt taagtgcttt 6660
gtttctgcgt ccaacatgag gaatgcagca ggccaattca tcgaggctgc ctatgcaaaa 6720
gcacttagaa ttgaacttgc ccagttggtg caggttgata aggttcgagg tactttggcc 6780
aagcttgagg cttttgctga taccgtggca ccccaactct cgcccggtga cattgttgtt 6840
gctcttggcc atacgcctgt tggcagcatc ttcgacctaa aggttggtgg taccaagcat 6900
actctccaag tcattgagac cagagtcctt gccgggtcca aaatgaccgt ggcgcgcgtc 6960
gttgacccaa cccccacgcc cccacccgca cccgtgccca tccccctccc accgaaagtt 7020
ctagagaatg gtcccaacgc ctggggggat ggggaccgtt tgaataagaa gaagaggcgt 7080
aggatggaaa ccgtcggcat ctttgtcatg ggtgggaaga agtaccagaa attttgggac 7140
aagaattccg gtgatgtgtt ttacgaggag gtccatgaca acacagatgc gtgggagtgc 7200
ctcagagttg gtgaccctgc cgactttgac cctgagaagg gaactctgtg tgggcatact 7260
actattgaag ataaggatta caaagtctac gcctccccat ctggcaagaa gttcctggtc 7320
cccgtcaact cagagagcgg aagagcccaa tgggaagctg caaagctttc cgtggagcag 7380
gcccttggca tgatgaatgt cgacggtgaa ctgacggcca aagaagtgga gaaactgaaa 7440
agaataattg acaaacttca gggcctgact aaggagcagt gtttaaactg ctag 7494

<210> SEQ ID NO 3
<211> LENGTH: 4392
<212> TYPE: DNA
<213> ORGANISM: Porcine reproductive and respiratory syndrome virus

<400> SEQUENCE: 3
ggagcagtgt ttaaactgct agccgccagc ggcttgaccc gctgtggtcg cggcggcttg 60
gttgttactg agacagcggt aaaaatagtc aaatttcaca accggacttt caccctaggg 120
cctgtgaatt taaaagtggc cagtgaggtt gagctgaaag acgcggtcga gcacaaccaa 180
cacccggttg caagaccggt tgacggtggt gttgtgctcc tgcgttccgc agttccttcg 240
cttatagatg tcctgatctc cggtgctgac gcatctccta agttactcgc tcgtcacggg 300
ccggggaaca ctgggatcga tggcacgctt tgggactttg aggccgaggc caccaaagag 360
gaaattgcac tcagtgcgca aataatacag gcttgtgaca ttaggcgcgg cgacgcacct 420
gaaattggtc tcccttacaa gctgtaccct gttaggggca accctgagcg ggtaaaagga 480
gttttacaga atacaaggtt tggagacata ccttacaaaa cccccagtga cactggaagc 540
ccagtgcacg cggctgcctg cctcacgccc aatgccactc cggtgactga tgggcgctct 600
gtcttggcta ctaccatgcc ctccggtttt gaattgtatg taccgaccat tccagcgtct 660
gtccttgatt atcttgactc taggcctgac tgccccaaac agttgacaga gcacggctgt 720

-continued gaggatgccg cattgagaga cctctccaag tatgacttgt ccacccaagg ctttgtttta 780
cctggggttc ttcgccttgt gcgtaagtac ctgtttgccc atgtgggtaa gtgcccgccc 840
gttcatcggc cttccactta ccctgccaag aattctatgg ctggaataaa tgggaacagg 900
tttccaacca aggacattca gagcgtccct gaaatcgacg ttctgtgcgc acaggccgtg 960
cgagaaaact ggcaaactgt taccccttgt accctcaaga aacagtattg tgggaagaag 1020
aagactagga caatactcgg caccaataat ttcattgcgt tggcccaccg ggcagcgttg 1080
agtggtgtca cccagggctt catgaaaaag gcgtttaact cgcccatcgc cctcgggaaa 1140
aacaaattta aggagctaca gactccggtc ttaggcaggt gccttgaagc tgatcttgca 1200
tcctgtgatc gatccacacc tgcaattgtc cgctggtttg ccgccaatct tctttatgaa 1260
cttgcctgtg ctgaagagca cctaccgtcg tacgtgctga actgctgcca tgacctattg 1320
gtcacgcagt ccggcgcagt gactaagagg ggtggcctat cgtctggcga cccgatcact 1380
tctgtgtcta acaccattta cagcttggtg atatatgcac agcacatggt gcttagttac 1440
tttaaaagtg gtcaccctca tggccttctg ttcctacaag accagctgaa gttcgaggac 1500
atgctcaaag tccaacccct gatcgtctat tcggacgacc tcgtgctgta tgccgaatct 1560
cccaccatgc cgaactacca ctggtgggtc gaacatctga atttgatgct gggttttcag 1620
acggacccaa agaagacagc cataacggac tcgccatcat ttctaggctg taggataata 1680
aatggacgcc agctagtccc caaccgtgac aggatcctcg cggccctcgc ttaccatatg 1740
aaggcaagca atgtttctga atactacgcc gcggcggctg caatactcat ggacagctgt 1800
gcttgtttag agtatgatcc tgaatggttt gaagagcttg tggttgggat agcgcagtgc 1860
gcccgcaagg acggctacag ctttcccggc ccgccgttct tcttgtccat gtgggaaaaa 1920
ctcagatcca atcatgaggg gaagaagtcc agaatgtgcg ggtattgcgg ggccccggct 1980
ccgtacgcca ctgcctgtgg cctcgacgtc tgtatttacc acacccactt ccaccagcat 2040
tgtccagtca taatctggtg tggccacccg gctggttctg gttcttgtag tgagtgcaaa 2100
ccccccctag ggaaaggcac aagccctcta gatgaggtgt tagaacaagt cccgtataag 2160
cctccacgga ctgtaatcat gcatgtggag cagggtctca cccctcttga cccaggcaga 2220
taccagactc gccgcggatt agtctccgtt aggcgtggca tcagaggaaa cgaagttgac 2280
ctaccagacg gtgattatgc tagcaccgcc ctactcccca cttgtaaaga gatcaacatg 2340
gtcgctgtcg cctctaatgt gttgcgcagc aggttcatca tcggtccgcc cggtgctggg 2400
aaaacatact ggctccttca gcaggtccag gatggtgatg tcatttacac accgactcac 2460
cagaccatgc tcgacatgat tagggctttg ggacgtgcc ggttcaacgt cccagcaggt 2520
acaacgctgc aattccctgc cccctcccgt accggcccgt gggttcgcat cctggccggc 2580
ggttggtgtc ctggtaagaa ttccttcctg gatgaagcag cgtattgtaa tcaccttgat 2640
gtcttgaggc tccttagcaa aaccaccctt acctgtctgg gagacttcaa acaactccac 2700
ccagtgggtt ttgattctca ttgctatgtt tttgacatca tgcctcagac ccagttgaag 2760
accatctgga gattcggaca gaacatctgt gatgccatcc aaccagatta cagggacaaa 2820
cttgtgtcca tggtcaacac aacccgtgta acctacatgg aaaaacctgt caagtatggg 2880
caagtcctca ccccttacca cagggaccga gaggacggcg ccatcacaat tgactccagt 2940
caaggcgcca catttgatgt ggttacactg catttgccca ctaaagattc actcaacagg 3000
caaagagccc ttgttgctat caccagggca agacatgcta tctttgtgta tgacccacac 3060
aggcaattgc agagcatgtt tgatcttcct gcgaagggca cacccgtcaa cctcgcagtg 3120

-continued caccgtgatg agcagctgat cgtactggat agaaataata aagaatgcac agttgctcag 3180
gctataggca acggagataa attcagggcc accgacaagc gcgttgtaga ttctctccgc 3240
gccatttgtg ctgatctgga agggtcgagc tccccgctcc ccaaggtcgc acacaacttg 3300
ggattttatt tctcacctga tttgacacag tttgctaaac tcccggtaga ccttgcaccc 3360
cactggcccg tggtgacaac ccagaacaat gaaaagtggc cggatcggct ggttgccagc 3420
cttcgccctg tccataagta tagccgtgcg tgcattggtg ccggctatat ggtgggcccc 3480
tcggtgtttc taggcacccc tggggtcgtg tcatactacc tcacaaaatt tgtcaagggc 3540
gaggctcaag tgcttccgga gacagtcttc agcaccggcc gaattgaggt ggattgccgg 3600
gagtatcttg atgacaggga gcgagaagtt gctgagtccc tcccacatgc cttcattggc 3660
gacgtcaaag gcaccaccgt tgggggatgt catcatgtca cctccaaata ccttccgcgc 3720
ttccttccca aggaatcagt cgcggtagtc ggggtttcga gccccgggaa agccgcaaaa 3780
gcagtgtgca cattgacgga tgtgtacctc ccagaccttg aggcctacct ccacccagag 3840
actcagtcta agtgctggaa agttatgttg gacttcaagg aagttcgact gatggtctgg 3900
aaagacaaga cggcctattt ccaacttgaa ggccgctatt tcacctggta tcagcttgca 3960
agctacgcct cgtacatccg tgttcctgtc aactccacgg tgtatctgga cccctgcatg 4020
ggccctgccc tttgcaacag aagagttgtc gggtccaccc attggggagc tgacctcgca 4080
gtcacccctt atgattacgg tgctaaaatc atcttgtcta gcgcttacca tggtgaaatg 4140
cctcctggat acaagattct ggcgtgcgcg gagttctcgc tcgacgaccc agtcaagtac 4200
aaacacacct ggggttttga atcggataca gcgtatctgt atgagttcac cggaaacggt 4260
gaggactggg aggattacaa tgatgcgttt cgtgcgcgcc agaaagggaa aatttataag 4320
gccactgcta ccagcatgaa gttttatttt cccccgggcc ccgtcattga accaacttta 4380
ggcctgaatt ga 4392

<210> SEQ ID NO 4
<211> LENGTH: 771
<212> TYPE: DNA
<213> ORGANISM: Porcine reproductive and respiratory syndrome virus

<400> SEQUENCE: 4
atgaaatggg gtctatacaa agcctcttcg acaaaattgg ccagcttttt gtggatgctt 60
tcacggaatt tttggtgtcc attgttgata tcatcatatt tttggccatt ttgtttggct 120
tcaccatcgc cggttggctg gtggtctttt gcatcagatt ggtttgctcc gcggtattcc 180
gtgcgcgccc tgccattcac cctgagcaat tacagaagat cctatgaggc ctttctttct 240
cagtgccggg tggacattcc cacctggggg gtaaaacacc ctttggggat gttttggcac 300
cataaggtgt caaccctgat tgatgaaatg gtgtcgcgtc gaatgtaccg catcatggaa 360
aaagcagggc aagctgcctg gaaacaggtg gtgagcgagg ctacgctgtc tcgcattagt 420
agtttggatg tggtggctca ttttcaacat cttgccgcca ttgaagccga gacctgtaaa 480
tatttggctt ctcgactgcc catgctacac aacctgcgca tgacagggtc aaatgtaacc 540
atagtgtata atagcacttt aaatcaggtg tttgctattt ttccaacccc tggttcccgg 600
ccaaagcttc atgattttca gcaatggcta atagctgtac attcctccat attttcctct 660
gttgcagctt cttgtactct tttgttgtg ctgtggttgc gggttccaat gctacgtact 720
gtttttggtt tccgctggtt aggggcaatt tttctttcga actcatggtg a 771

-continued

<210> SEQ ID NO 5
<211> LENGTH: 765
<212> TYPE: DNA
<213> ORGANISM: Porcine reproductive and respiratory syndrome virus

<400> SEQUENCE: 5

```
atggctaata gctgtacatt cctccatatt ttcctctgtt gcagcttctt gtactctttt     60
tgttgtgctg tggttgcggg ttccaatgct acgtactgtt tttggtttcc gctggttagg    120
ggcaattttt ctttcgaact catggtgaat tacacggtgt gtccaccttg cctcacccga    180
caagcagccg ctgaggtcct tgaacccggt aggtctcttt ggtgcaggat agggcatgac    240
cgatgtgggg aggacgatca cgacgaacta gggttcatgg ttccgcctgg cctctccagc    300
gaaagccact tgaccagtgt ttacgcctgg ttggcgttcc tgtccttcag ctacacggcc    360
cagttccatc ccgagatatt tgggataggg aacgtgagtg aagtttatgt tgacatcaag    420
caccaattca tctgcgccgt tcatgacggg cagaacacca ccttgcctcg ccatgacaat    480
atttcagccg tatttcagac ctactatcaa catcaggtcg acggcggcaa ttggtttcac    540
ctagaatggc tgcgtccctt cttttcctct tggttggttt taaatgtttc gtggtttctc    600
aggcgttcgc ctgcaagcca tgtttcagtt cgagtctttc agacatcaaa accaacacta    660
ccgcagcatc aggctttgtt gtcctccagg acatcagctg ccttaggcat ggcgactcgt    720
cctttccgac gattcgcaaa agctctcaat gccgcacggc gatag                    765
```

<210> SEQ ID NO 6
<211> LENGTH: 537
<212> TYPE: DNA
<213> ORGANISM: Porcine reproductive and respiratory syndrome virus

<400> SEQUENCE: 6

```
atggctgcgt cccttctttt cctcttggtt ggttttaaat gtttcgtggt ttctcaggcg     60
ttcgcctgca agccatgttt cagttcgagt ctttcagaca tcaaaaccaa cactaccgca    120
gcatcaggct ttgttgtcct ccaggacatc agctgcctta ggcatggcga ctcgtccttt    180
ccgacgattc gcaaaagctc tcaatgccgc acggcgatag ggacacccgt gtatatcacc    240
atcacagcca atgtgacaga tgagaattac ttacattctt ctgatctcct catgctttct    300
tcttgccttt tctatgcttc tgagatgagt gaaaagggat tcaaggtggt gtttggcaat    360
gtgtcaggca tcgtggctgt gtgtgtcaac tttaccagct acgtccaaca tgtcaaagag    420
tttacccaac gctccttggt ggtcgatcat gtgcggctgc ttcatttcat gacacctgag    480
accatgaggt gggcaaccgt tttagcctgt ctttttgcca tcctactggc aatttga       537
```

<210> SEQ ID NO 7
<211> LENGTH: 603
<212> TYPE: DNA
<213> ORGANISM: Porcine reproductive and respiratory syndrome virus

<400> SEQUENCE: 7

```
atgttgggga aatgcttgac cgcgggctgt tgctcgcgat tgctttcttt gtggtgtatc     60
gtgccgttct gttttgctgt gctcggcagc gccaacagca gcagcagctc tcattttcag    120
ttgatttata acttgacgct atgtgagctg aatggcacag attggctggc agaaaaattt    180
gattgggcag tggagacttt tgtcatcttt cccgtgttga ctcacattgt ttcctatggt    240
gcactcacca ccagccattt ccttgacaca gttggtctgg ttactgtgtc caccgccggg    300
ttttatcacg ggcggtatgt cttgagtagc atctacgcgg tctgtgctct ggctgcgttg    360
atttgcttcg ttattaggct tgcgaagaac tgcatgtcct ggcgctactc ttgtaccaga    420
```

tataccaact tccttctgga cactaagggc agactctatc gttggcggtc gcccgttatc 480
atagaaaaag gggtaaggt tgaggtcgaa ggtcacctga tcgacctcaa aagagttgtg 540
cttgatggtt ccgtggcaac ccctttaacc agagtttcag cggaacaatg ggtcgtctc 600 tag 603

<210> SEQ ID NO 8
<211> LENGTH: 525
<212> TYPE: DNA
<213> ORGANISM: Porcine reproductive and respiratory syndrome virus

<400> SEQUENCE: 8
atggggtcgt ctctagacga cttttgccat gatagcacgg ctccacaaaa ggtgcttttg 60
gcgttttcca ttacctacac gccagtaatg atatatgctc taaaggtaag tcgcggccga 120
ctactagggc ttctgcacct tttgatcttt ctgaattgtg cttttacctt cgggtacatg 180
acattcgagc actttcagag cacaaatagg gtcgcgctca ctatgggagc agtagttgca 240
cttctttggg gggtgtactc agccatagaa acctggaaat tcatcacctc cagatgccgt 300
ttgtgcttgc taggccgcaa gtacattctg gcccctgccc accacgtcga aagtgccgcg 360
ggctttcatc cgattgcggc aaatgataac cacgcatttg tcgtccggcg tcccggctcc 420
actacggtta acggcacatt ggtgcccggg ttgaaaagcc tcgtgttggg tggcagaaaa 480
gctgttaaac agggagtggt aaaccttgtc aaatatgcca aataa 525

<210> SEQ ID NO 9
<211> LENGTH: 372
<212> TYPE: DNA
<213> ORGANISM: Porcine reproductive and respiratory syndrome virus

<400> SEQUENCE: 9
atgccaaata acaacggcaa gcagcaaaag aaaaagaagg ggaatggcca gccagtcaat 60
cagctgtgcc agatgctggg taaaatcatc gcccagcaaa accagtccag aggcaaggga 120
ccgggcaaga aaagtaagaa gaaaaacccg gagaagcccc atttcctctc agcgaccgaa 180
gatgacgtca ggcatcactt cacccctggt gagcggcaat tgtgtctgtc gtcgatccag 240
actgccttta accagggcgc tggaacttgt accctgtcag attcagggag gataagttac 300
actgtggagt ttagtttgcc gacgcatcat actgtgcgcc tgatccgcgt cacagcatca 360
ccctcagcat ga 372

<210> SEQ ID NO 10
<211> LENGTH: 18
<212> TYPE: DNA
<213> ORGANISM: Porcine reproductive and respiratory syndrome virus

<400> SEQUENCE: 10
acagtttggt gatctatg 18

<210> SEQ ID NO 11
<211> LENGTH: 17
<212> TYPE: DNA
<213> ORGANISM: Porcine reproductive and respiratory syndrome virus

<400> SEQUENCE: 11
cagattcaga tgttcaa 17

<210> SEQ ID NO 12
<211> LENGTH: 24

<212> TYPE: DNA
<213> ORGANISM: Porcine reproductive and respiratory syndrome virus

<400> SEQUENCE: 12
acctcgtgct gtatgccgaa tctc 24

<210> SEQ ID NO 13
<211> LENGTH: 24
<212> TYPE: DNA
<213> ORGANISM: Porcine reproductive and respiratory syndrome virus

<400> SEQUENCE: 13
tcaggcctaa agttggttca atga 24

<210> SEQ ID NO 14
<211> LENGTH: 24
<212> TYPE: DNA
<213> ORGANISM: Porcine reproductive and respiratory syndrome virus

<400> SEQUENCE: 14
gatgactggg ctactgacga ggat 24

<210> SEQ ID NO 15
<211> LENGTH: 21
<212> TYPE: DNA
<213> ORGANISM: Porcine reproductive and respiratory syndrome virus

<400> SEQUENCE: 15
agagcggctg ggatgacact g 21

<210> SEQ ID NO 16
<211> LENGTH: 22
<212> TYPE: DNA
<213> ORGANISM: Porcine reproductive and respiratory syndrome virus

<400> SEQUENCE: 16
ccggggaagc cagacgattg aa 22

<210> SEQ ID NO 17
<211> LENGTH: 24
<212> TYPE: DNA
<213> ORGANISM: Porcine reproductive and respiratory syndrome virus

<400> SEQUENCE: 17
agggggagca aagaaggggt catc 24

<210> SEQ ID NO 18
<211> LENGTH: 20
<212> TYPE: DNA
<213> ORGANISM: Porcine reproductive and respiratory syndrome virus

<400> SEQUENCE: 18
agcacgctct ggtgcaactg 20

<210> SEQ ID NO 19
<211> LENGTH: 19
<212> TYPE: DNA
<213> ORGANISM: Porcine reproductive and respiratory syndrome virus

<400> SEQUENCE: 19
gccgcggcgt agtattcag 19

<210> SEQ ID NO 20
<211> LENGTH: 22

<212> TYPE: DNA
<213> ORGANISM: Porcine reproductive and respiratory syndrome virus

<400> SEQUENCE: 20
cgcgtcacag catcaccctc ag 22

<210> SEQ ID NO 21
<211> LENGTH: 25
<212> TYPE: DNA
<213> ORGANISM: Porcine reproductive and respiratory syndrome virus

<400> SEQUENCE: 21
cggtaggttg gttaacacat gagtt 25

<210> SEQ ID NO 22
<211> LENGTH: 23
<212> TYPE: DNA
<213> ORGANISM: Porcine reproductive and respiratory syndrome virus

<400> SEQUENCE: 22
tggctcttcg ggcctataaa ata 23

<210> SEQ ID NO 23
<211> LENGTH: 56
<212> TYPE: DNA
<213> ORGANISM: Porcine reproductive and respiratory syndrome virus

<400> SEQUENCE: 23
ctagattaat taatacgact cactataggg atgacgtata ggtgttggct ctatgc 56

<210> SEQ ID NO 24
<211> LENGTH: 56
<212> TYPE: DNA
<213> ORGANISM: Porcine reproductive and respiratory syndrome virus

<400> SEQUENCE: 24
taattaatta tgctgagtga tatccctact gcatatccac aaccgagata cggtgc 56

<210> SEQ ID NO 25
<211> LENGTH: 27
<212> TYPE: DNA
<213> ORGANISM: Porcine reproductive and respiratory syndrome virus

<400> SEQUENCE: 25
actcagtcta agtgctggaa agttatg 27

<210> SEQ ID NO 26
<211> LENGTH: 59
<212> TYPE: DNA
<213> ORGANISM: Porcine reproductive and respiratory syndrome virus

<400> SEQUENCE: 26
gggatttaaa tatgcatttt tttttttttt tttttttaat tgcggccgca tggttctcg 59

<210> SEQ ID NO 27
<211> LENGTH: 36
<212> TYPE: DNA
<213> ORGANISM: Porcine reproductive and respiratory syndrome virus

<400> SEQUENCE: 27
attagatctt gccaccatgg tggggaaatg cttgac 36

<210> SEQ ID NO 28
<211> LENGTH: 46

<212> TYPE: DNA
<213> ORGANISM: Porcine reproductive and respiratory syndrome virus

<400> SEQUENCE: 28
ctttacgcgt ttgcttaagt tatttggcgt atttgacaag gtttac 46

<210> SEQ ID NO 29
<211> LENGTH: 31
<212> TYPE: DNA
<213> ORGANISM: Porcine reproductive and respiratory syndrome virus

<400> SEQUENCE: 29
caacacgcgt cagcaaaaga aaaagaaggg g 31

<210> SEQ ID NO 30
<211> LENGTH: 20
<212> TYPE: DNA
<213> ORGANISM: Porcine reproductive and respiratory syndrome virus

<400> SEQUENCE: 30
gcgcgttggc cgattcatta 20

<210> SEQ ID NO 31
<211> LENGTH: 37
<212> TYPE: DNA
<213> ORGANISM: Porcine reproductive and respiratory syndrome virus

<400> SEQUENCE: 31
ctcgttaatt aaaccgtcat gacgtatagg tgttggc 37

<210> SEQ ID NO 32
<211> LENGTH: 3796
<212> TYPE: DNA
<213> ORGANISM: Porcine reproductive and respiratory syndrome virus

<400> SEQUENCE: 32
gaattcgagc ttgcatgcct gcaggtcgtt acataactta cggtaaatgg cccgcctggc 60
tgaccgccca acgacccccg cccattgacg tcaataatga cgtatgttcc catagtaacg 120
ccaataggga ctttccattg acgtcaatgg gtggagtatt tacggtaaac tgcccacttg 180
gcagtacatc aagtgtatca tatgccaagt acgcccccta ttgacgtcaa tgacggtaaa 240
tggcccgcct ggcattatgc ccagtacatg accttatggg actttcctac ttggcagtac 300
atctacgtat tagtcatcgc tattaccatg gtgatgcggt tttggcagta catcaatggg 360
cgtggatagc ggtttgactc acggggattt ccaagtctcc accccattga cgtcaatggg 420
agtttgtttt ggcaccaaaa tcaacgggac tttccaaaat gtcgtaacaa ctccgcccca 480
ttgacgcaaa tgggcggtag gcgtgtacgg tgggaggtct atataagcag agctcgttta 540
gtgaaccgtc agatcgcctg gagacgccat ccacgctgtt ttgacctcca tagaagacac 600
cgggaccgat ccagcctccg gactctagag gatccggtac tcgaggaact gaaaaaccag 660
aaagttaact ggtaagttta gtctttttgt cttttatttc aggtcccgga tccggtggtg 720
gtgcaaatca aagaactgct cctcagtgga tgttgccttt acttctaggc ctgtacggaa 780
gtgttacttc tgctctaaaa gctgcggaat tgtacccgcg gccgcaagat atcgccctag 840
gaagatctcg atcgattggt accaatccgc gacccettaa ttaacagcta gcggatttaa 900
atcagggccc gggatactag tgagcggccg cggggatcca gacatgataa gatacattga 960
tgagtttgga caaaccacaa ctagaatgca gtgaaaaaaa tgctttattt gtgaaatttg 1020
tgatgctatt gctttatttg taaccattat aagctgcaat aaacaagtta acaacaacaa 1080

-continued

```
ttgcattcat tttatgtttc aggttcaggg ggaggtgtgg gaggtttttt cggatcctct   1140
agagtcgacc tgcaggcatg caagcttggc gtaatcatgg tcatagctgt ttcctgtgtg   1200
aaattgttat ccgctcacaa ttccacacaa catacgagcc ggaagcataa agtgtaaagc   1260
ctggggtgcc taatgagtga gctaactcac attaattgcg ttgcgctcac tgcccgcttt   1320
ccagtcggga aacctgtcgt gccagctgca ttaatgaatc ggccaacgcg cggggagagg   1380
cggtttgcgt attgggcgct cttccgcttc ctcgctcact gactcgctgc gctcggtcgt   1440
tcggctgcgg cgagcggtat cagctcactc aaaggcggta atacggttat ccacagaatc   1500
aggggataac gcaggaaaga acatgtgagc aaaaggccag caaaaggcca ggaaccgtaa   1560
aaaggccgcg ttgctggcgt ttttccatag gctccgcccc cctgacgagc atcacaaaaa   1620
tcgacgctca agtcagaggt ggcgaaaccc gacaggacta taaagatacc aggcgtttcc   1680
ccctggaagc tccctcgtgc gctctcctgt tccgaccctg ccgcttaccg gatacctgtc   1740
cgcctttctc ccttcgggaa gcgtggcgct ttctcatagc tcacgctgta ggtatctcag   1800
ttcggtgtag gtcgttcgct ccaagctggg ctgtgtgcac gaaccccccg ttcagcccga   1860
ccgctgcgcc ttatccggta actatcgtct tgagtccaac ccggtaagac acgacttatc   1920
gccactggca gcagccactg gtaacaggat tagcagagcg aggtatgtag gcggtgctac   1980
agagttcttg aagtggtggc ctaactacgg ctacactaga aggacagtat ttggtatctg   2040
cgctctgctg aagccagtta ccttcggaaa aagagttggt agctcttgat ccggcaaaca   2100
aaccaccgct ggtagcggtg gtttttttgt ttgcaagcag cagattacgc gcagaaaaaa   2160
aggatctcaa gaagatcctt tgatcttttc tacggggtct gacgctcagt ggaacgaaaa   2220
ctcacgttaa gggattttgg tcatgagatt atcaaaaagg atcttcacct agatcctttt   2280
aaattaaaaa tgaagtttta aatcaatcta aagtatatat gagtaaactt ggtctgacag   2340
ttaccaatgc ttaatcagtg aggcacctat ctcagcgatc tgtctatttc gttcatccat   2400
agttgcctga ctccccgtcg tgtagataac tacgatacgg gagggcttac catctggccc   2460
cagtgctgca atgataccgc gagacccacg ctcaccggct ccagatttat cagcaataaa   2520
ccagccagcc ggaagggccg agcgcagaag tggtcctgca actttatccg cctccatcca   2580
gtctattaat tgttgccggg aagctagagt aagtagttcg ccagttaata gtttgcgcaa   2640
cgttgttgcc attgctacag gcatcgtggt gtcacgctcg tcgtttggta tggcttcatt   2700
cagctccggt tcccaacgat caaggcgagt tacatgatcc cccatgttgt gcaaaaaagc   2760
ggttagctcc ttcggtcctc cgatcgttgt cagaagtaag ttggccgcag tgttatcact   2820
catggttatg gcagcactgc ataattctct tactgtcatg ccatccgtaa gatgcttttc   2880
tgtgactggt gagtactcaa ccaagtcatt ctgagaatag tgtatgcggc gaccgagttg   2940
ctcttgcccg gcgtcaatac gggataatac cgcgccacat agcagaactt taaaagtgct   3000
catcattgga aaacgttctt cggggcgaaa actctcaagg atcttaccgc tgttgagatc   3060
cagttcgatg taacccactc gtgcacccaa ctgatcttca gcatctttta ctttcaccag   3120
cgtttctggg tgagcaaaaa caggaaggca aaatgccgca aaaaagggaa taagggcgac   3180
acggaaatgt tgaatactca tactcttcct ttttcaatat tattgaagca tttatcaggg   3240
ttattgtctc atgagcggat acatatttga atgtatttag aaaaataaac aaataggggt   3300
tccgcgcaca tttccccgaa aagtgccacc tgacgtctaa gaaaccatta ttatcatgac   3360
attaacctat aaaaataggc gtatcacgag gccctttcgt ctcgcgcgtt tcggtgatga   3420
cggtgaaaac ctctgacaca tgcagctccc ggagacggtc acagcttgtc tgtaagcgga   3480
```

tgccgggagc agacaagccc gtcagggcgc gtcagcgggt gttggcgggt gtcggggctg 3540
gcttaactat gcggcatcag agcagattgt actgagagtg caccatatgc ggtgtgaaat 3600
accgcacaga tgcgtaagga gaaaataccg catcaggcgc cattcgccat tcaggctgcg 3660
caactgttgg gaagggcgat cggtgcgggc ctcttcgcta ttacgccagc tggcgaaagg 3720
gggatgtgct gcaaggcgat taagttgggt aacgccaggg ttttcccagt cacgacgttg 3780
taaaacgacg gccagt 3796

<210> SEQ ID NO 33
<211> LENGTH: 22
<212> TYPE: DNA
<213> ORGANISM: Porcine reproductive and respiratory syndrome virus

<400> SEQUENCE: 33
cgttaattaa accgactagt gc 22

<210> SEQ ID NO 34
<211> LENGTH: 30
<212> TYPE: DNA
<213> ORGANISM: Porcine reproductive and respiratory syndrome virus

<400> SEQUENCE: 34
tcgagcaatt aatttggctg atcacgccgg 30

<210> SEQ ID NO 35
<211> LENGTH: 24
<212> TYPE: DNA
<213> ORGANISM: Porcine reproductive and respiratory syndrome virus

<400> SEQUENCE: 35
cggggacggt ttcaaatttc actt 24

<210> SEQ ID NO 36
<211> LENGTH: 50
<212> TYPE: DNA
<213> ORGANISM: Porcine reproductive and respiratory syndrome virus

<400> SEQUENCE: 36
tatataagca gagctcgtta attaaaccgt catgacgtat aggtgttggc 50

<210> SEQ ID NO 37
<211> LENGTH: 48
<212> TYPE: DNA
<213> ORGANISM: Porcine reproductive and respiratory syndrome virus

<400> SEQUENCE: 37
aggtcgacgg cggcaattgg tttcacctag agtggctgcg tcccttct 48

<210> SEQ ID NO 38
<211> LENGTH: 30
<212> TYPE: DNA
<213> ORGANISM: Porcine reproductive and respiratory syndrome virus

<400> SEQUENCE: 38
tcttaagcat tggctgtgat ggtgatatac 30

<210> SEQ ID NO 39
<211> LENGTH: 44
<212> TYPE: DNA
<213> ORGANISM: Porcine reproductive and respiratory syndrome virus

<400> SEQUENCE: 39
cttcttaagt ccacgcgttt tcttcttgcc ttttctatgc ttct 44

<210> SEQ ID NO 40
<211> LENGTH: 19
<212> TYPE: DNA
<213> ORGANISM: Porcine reproductive and respiratory syndrome virus

<400> SEQUENCE: 40
tgcccggtcc cttgcctct 19

<210> SEQ ID NO 41
<211> LENGTH: 26
<212> TYPE: DNA
<213> ORGANISM: Porcine reproductive and respiratory syndrome virus

<400> SEQUENCE: 41
gtttacgcgt cgctccttgg tggtcg 26

<210> SEQ ID NO 42
<211> LENGTH: 23
<212> TYPE: DNA
<213> ORGANISM: Porcine reproductive and respiratory syndrome virus

<400> SEQUENCE: 42
aacagaagag ttgtcgggtc cac 23

<210> SEQ ID NO 43
<211> LENGTH: 49
<212> TYPE: DNA
<213> ORGANISM: Porcine reproductive and respiratory syndrome virus

<400> SEQUENCE: 43
gctttgacgc gtccccactt aagttcaatt caggcctaaa gttggttca 49

<210> SEQ ID NO 44
<211> LENGTH: 82
<212> TYPE: DNA
<213> ORGANISM: Porcine reproductive and respiratory syndrome virus

<400> SEQUENCE: 44
gcgacgcgtg ttccgtggca accccttttaa ccagagtttc agcggaacaa tgaaatgggg 60
tctatacaaa gcctcttcga ca 82

<210> SEQ ID NO 45
<211> LENGTH: 26
<212> TYPE: DNA
<213> ORGANISM: Porcine reproductive and respiratory syndrome virus

<400> SEQUENCE: 45
aacagaacgg cacgatacac cacaaa 26

<210> SEQ ID NO 46
<211> LENGTH: 24
<212> TYPE: DNA
<213> ORGANISM: Porcine reproductive and respiratory syndrome virus

<400> SEQUENCE: 46
caaagggcga aaaaccgtct atca 24

<210> SEQ ID NO 47
<211> LENGTH: 23
<212> TYPE: DNA
<213> ORGANISM: Porcine reproductive and respiratory syndrome virus

<400> SEQUENCE: 47
ccccacttaa gttcaattca ggc 23

<210> SEQ ID NO 48
<211> LENGTH: 37
<212> TYPE: DNA
<213> ORGANISM: Porcine reproductive and respiratory syndrome virus

<400> SEQUENCE: 48
gctccttaag aacaacgcgt cgccattgaa gccgaga 37

<210> SEQ ID NO 49
<211> LENGTH: 24
<212> TYPE: DNA
<213> ORGANISM: Porcine reproductive and respiratory syndrome virus

<400> SEQUENCE: 49
gcaagcctaa taacgaagca aatc 24

<210> SEQ ID NO 50
<211> LENGTH: 42
<212> TYPE: DNA
<213> ORGANISM: Porcine reproductive and respiratory syndrome virus

<400> SEQUENCE: 50
ctgtcaagtg ttaggatcac gcgtccaaaa tactcagctc aa 42

<210> SEQ ID NO 51
<211> LENGTH: 42
<212> TYPE: DNA
<213> ORGANISM: Porcine reproductive and respiratory syndrome virus

<400> SEQUENCE: 51
ttgagctgag tattttggac gcgtgatcct aacacttgac ag 42

<210> SEQ ID NO 52
<211> LENGTH: 33
<212> TYPE: DNA
<213> ORGANISM: Porcine reproductive and respiratory syndrome virus

<400> SEQUENCE: 52
gccacgcgtg ccaccatggt gagcaagggc gag 33

<210> SEQ ID NO 53
<211> LENGTH: 31
<212> TYPE: DNA
<213> ORGANISM: Porcine reproductive and respiratory syndrome virus

<400> SEQUENCE: 53
gccacgcgtg ttatctagat ccggtggatc c 31

<210> SEQ ID NO 54
<211> LENGTH: 40
<212> TYPE: DNA
<213> ORGANISM: Porcine reproductive and respiratory syndrome virus

<400> SEQUENCE: 54
tcaagccgct ggcggctagc agtttaaaca ctgctcctta 40

<210> SEQ ID NO 55
<211> LENGTH: 41
<212> TYPE: DNA
<213> ORGANISM: Porcine reproductive and respiratory syndrome virus

<400> SEQUENCE: 55
ctcgggaaaa tagaaaacac cggtgagatg atcaaccagg g 41

<210> SEQ ID NO 56
<211> LENGTH: 41
<212> TYPE: DNA
<213> ORGANISM: Porcine reproductive and respiratory syndrome virus

<400> SEQUENCE: 56
ccctggttga tcatctcacc ggtgttttct attttcccga g 41

<210> SEQ ID NO 57
<211> LENGTH: 40
<212> TYPE: DNA
<213> ORGANISM: Porcine reproductive and respiratory syndrome virus

<400> SEQUENCE: 57
gccgcccacc ggtgaggtga gcaagggcga ggagctgttc 40

<210> SEQ ID NO 58
<211> LENGTH: 37
<212> TYPE: DNA
<213> ORGANISM: Porcine reproductive and respiratory syndrome virus

<400> SEQUENCE: 58
gccgcccacc ggtgttgtta tctagatccg gtggatc 37

<210> SEQ ID NO 59
<211> LENGTH: 30
<212> TYPE: DNA
<213> ORGANISM: Porcine reproductive and respiratory syndrome virus

<400> SEQUENCE: 59
gccacgcgtg tgagcaaggg cgaggagctg 30

<210> SEQ ID NO 60
<211> LENGTH: 33
<212> TYPE: DNA
<213> ORGANISM: Porcine reproductive and respiratory syndrome virus

<400> SEQUENCE: 60
cgcgtatacc catacgacgt cccagactac gca 33

<210> SEQ ID NO 61
<211> LENGTH: 33
<212> TYPE: DNA
<213> ORGANISM: Porcine reproductive and respiratory syndrome virus

<400> SEQUENCE: 61
ccggtgcgta gtctgggacg tcgtatgggt ata 33

<210> SEQ ID NO 62
<211> LENGTH: 39
<212> TYPE: DNA
<213> ORGANISM: Porcine reproductive and respiratory syndrome virus

<400> SEQUENCE: 62
ccctgtcaag tgttaagatc acaggtgaga tgatcaacc 39

<210> SEQ ID NO 63
<211> LENGTH: 41
<212> TYPE: DNA
<213> ORGANISM: Porcine reproductive and respiratory syndrome virus

<400> SEQUENCE: 63
ccctggttga tcatctcacc tgtgatctta acacttgaca g 41

<210> SEQ ID NO 64
<211> LENGTH: 132
<212> TYPE: PRT
<213> ORGANISM: Porcine reproductive and respiratory syndrome virus

<400> SEQUENCE: 64

Arg Pro Lys Tyr Ser Ala Gln Ala Ile Ile Asp Leu Gly Gly Pro Cys
1 5 10 15

Ser Gly His Leu Gln Arg Glu Lys Glu Ala Cys Leu Arg Ile Met Arg
20 25 30

Glu Ala Cys Asp Ala Ala Lys Leu Ser Asp Pro Ala Thr Gln Glu Trp
35 40 45

Leu Ser Arg Met Trp Asp Arg Val Asp Met Leu Thr Trp Arg Asn Thr
50 55 60

Ser Ala Tyr Gln Ala Phe Arg Thr Leu Asp Gly Arg Phe Gly Phe Leu
65 70 75 80

Pro Lys Met Ile Leu Glu Thr Pro Pro Pro Tyr Pro Cys Gly Phe Val
85 90 95

Met Leu Pro His Thr Pro Ala Pro Ser Val Ser Ala Glu Ser Asp Leu
100 105 110

Thr Ile Gly Ser Val Ala Thr Glu Asp Ile Pro Arg Ile Leu Gly Lys
115 120 125

Ile Glu Asn Thr
130

<210> SEQ ID NO 65
<211> LENGTH: 132
<212> TYPE: PRT
<213> ORGANISM: Porcine reproductive and respiratory syndrome virus

<400> SEQUENCE: 65

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 66
<211> LENGTH: 132
<212> TYPE: PRT
<213> ORGANISM: Porcine reproductive and respiratory syndrome virus

<400> SEQUENCE: 66

```
Arg Pro Lys Tyr Ser Ala Gln Ala Ile Ile Asp Ser Gly Gly Pro Cys
1               5                   10                  15

Ser Gly His Leu Gln Lys Glu Lys Glu Ala Cys Leu Ser Ile Met Arg
            20                  25                  30

Glu Ala Cys Asp Ala Ser Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Phe Arg Thr Leu Asn Gly Arg Phe Glu Phe Leu
65                  70                  75                  80

Pro Lys Met Ile Leu Glu Thr Pro Pro Pro His Pro Cys Gly Phe Val
                85                  90                  95

Met Leu Pro His Thr Pro Ala Pro Ser Val Ser Ala Glu Ser Asp Leu
            100                 105                 110

Thr Ile Gly Ser Val Ala Thr Glu Asp Val Pro Arg Ile Leu Gly Lys
        115                 120                 125

Ile Gly Asp Thr
    130
```

<210> SEQ ID NO 67
<211> LENGTH: 132
<212> TYPE: PRT
<213> ORGANISM: Porcine reproductive and respiratory syndrome virus

<400> SEQUENCE: 67

```
Arg Pro Lys Tyr Ser Ala Gln Ala Ile Ile Asp Ser Gly Gly Pro Cys
1               5                   10                  15

Ser Gly His Leu Gln Lys Glu Lys Glu Ala Cys Leu Ser Ile Met Arg
            20                  25                  30

Glu Ala Cys Asp Ala Ser Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Phe Arg Thr Leu Asn Gly Arg Phe Glu Phe Leu
65                  70                  75                  80

Pro Lys Met Ile Leu Glu Thr Pro Pro Pro His Pro Cys Gly Phe Val
                85                  90                  95

Met Leu Pro His Thr Pro Ala Pro Ser Val Ser Ala Glu Ser Asp Leu
            100                 105                 110

Thr Ile Gly Ser Val Ala Thr Glu Asp Val Pro Arg Ile Leu Gly Lys
        115                 120                 125

Ile Gly Asp Thr
    130
```

<210> SEQ ID NO 68
<211> LENGTH: 132
<212> TYPE: PRT
<213> ORGANISM: Porcine reproductive and respiratory syndrome virus

<400> SEQUENCE: 68

```
Arg Pro Lys Tyr Ser Ala Gln Ala Ile Ile Asp Ser Gly Gly Pro Cys
1               5                   10                  15

Ser Gly His Leu Gln Glu Val Lys Glu Ala Cys Leu Ser Val Met Arg
            20                  25                  30

Glu Ala Cys Asp Ala Thr Lys Leu Asp Asp Pro Ala Thr Gln Glu Trp
```

```
        35                  40                  45

Leu Ser Arg Met Trp Asp Arg Val Asp Met Leu Thr Trp Arg Asn Thr
    50                  55                  60

Ser Val Tyr Gln Ala Ile Cys Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Ile Glu Asn Val
    130


<210> SEQ ID NO 69
<211> LENGTH: 132
<212> TYPE: PRT
<213> ORGANISM: Porcine reproductive and respiratory syndrome virus

<400> SEQUENCE: 69

Arg Pro Lys Tyr Ser Ala Gln Ala Ile Ile Asp Ser Gly Gly Pro Cys
1               5                   10                  15

Ser Gly His Leu Gln Glu Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Ile Cys Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Met Glu Asn Val
    130


<210> SEQ ID NO 70
<211> LENGTH: 132
<212> TYPE: PRT
<213> ORGANISM: Porcine reproductive and respiratory syndrome virus

<400> SEQUENCE: 70

Arg Pro Lys Tyr Ser Ala Gln Ala Ile Ile Asp Ser Gly Gly Pro Cys
1               5                   10                  15

Ser Gly His Leu Gln Glu Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val Tyr Gln Ala Ile Cys Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95
```

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 71
<211> LENGTH: 132
<212> TYPE: PRT
<213> ORGANISM: Porcine reproductive and respiratory syndrome virus

<400> SEQUENCE: 71

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 72
<211> LENGTH: 132
<212> TYPE: PRT
<213> ORGANISM: Porcine reproductive and respiratory syndrome virus

<400> SEQUENCE: 72

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 73
<211> LENGTH: 132
<212> TYPE: PRT
<213> ORGANISM: Porcine reproductive and respiratory syndrome virus

<400> SEQUENCE: 73

```
Arg Pro Lys Tyr Ser Ala Gln Ala Ile Ile Asp Ser Gly Gly Pro Cys
1               5                   10                  15

Ser Gly His Leu Gln Glu Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val Tyr Gln Ala Ile Cys Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Ile Glu Asn Val
    130
```

<210> SEQ ID NO 74
<211> LENGTH: 132
<212> TYPE: PRT
<213> ORGANISM: Porcine reproductive and respiratory syndrome virus

<400> SEQUENCE: 74

```
Arg Pro Lys Tyr Ser Ala Gln Ala Ile Ile Asp Ser Gly Gly Pro Cys
1               5                   10                  15

Ser Gly His Leu Gln Glu Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val Tyr Gln Ala Ile Cys Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Ile Glu Asn Val
    130
```

<210> SEQ ID NO 75
<211> LENGTH: 132
<212> TYPE: PRT
<213> ORGANISM: Porcine reproductive and respiratory syndrome virus

<400> SEQUENCE: 75

```
Arg Pro Lys Tyr Ser Ala Gln Ala Ile Ile Asp Ser Gly Gly Pro Cys
1               5                   10                  15
```

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 76
<211> LENGTH: 132
<212> TYPE: PRT
<213> ORGANISM: Porcine reproductive and respiratory syndrome virus

<400> SEQUENCE: 76

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 77
<211> LENGTH: 132
<212> TYPE: PRT
<213> ORGANISM: Porcine reproductive and respiratory syndrome virus

<400> SEQUENCE: 77

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 78
<211> LENGTH: 132
<212> TYPE: PRT
<213> ORGANISM: Porcine reproductive and respiratory syndrome virus

<400> SEQUENCE: 78

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 79
<211> LENGTH: 132
<212> TYPE: PRT
<213> ORGANISM: Porcine reproductive and respiratory syndrome virus

<400> SEQUENCE: 79

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys

```
        115                 120                 125

Ile Glu Asn Val
    130


<210> SEQ ID NO 80
<211> LENGTH: 132
<212> TYPE: PRT
<213> ORGANISM: Porcine reproductive and respiratory syndrome virus

<400> SEQUENCE: 80

Arg Pro Lys Tyr Ser Ala Gln Ala Ile Ile Asp Ser Gly Gly Pro Cys
1               5                   10                  15

Ser Gly His Leu Gln Gly Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val Cys Gln Ala Ile Arg Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Ile Glu Asn Val
    130


<210> SEQ ID NO 81
<211> LENGTH: 132
<212> TYPE: PRT
<213> ORGANISM: Porcine reproductive and respiratory syndrome virus

<400> SEQUENCE: 81

Arg Pro Lys Tyr Ser Ala Gln Ala Ile Ile Asp Ser Gly Gly Pro Cys
1               5                   10                  15

Ser Gly His Leu Gln Gly Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val Cys Gln Ala Ile Arg Thr Leu Asp Gly Arg Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Glu Lys
        115                 120                 125

Ile Glu Asn Val
    130


<210> SEQ ID NO 82
<211> LENGTH: 132
<212> TYPE: PRT
<213> ORGANISM: Porcine reproductive and respiratory syndrome virus
```

<400> SEQUENCE: 82

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asn Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 83
<211> LENGTH: 132
<212> TYPE: PRT
<213> ORGANISM: Porcine reproductive and respiratory syndrome virus

<400> SEQUENCE: 83

Arg Pro Thr Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp
35 40 45

Leu Ser Arg Met Trp Asp Arg Val Asp Met Leu Thr Trp Arg Asn Thr
50 55 60

Ser Val Tyr Gln Ala Ile Cys Thr Leu Asp Gly Arg Leu Lys Phe Leu
65 70 75 80

Pro Lys Met Ile Leu Glu Thr Pro Pro Pro Tyr Pro Cys Glu Phe Val
85 90 95

Met Met Pro His Thr Pro Ala Pro Ser Val Gly Ala Glu Ser Asp Leu
100 105 110

Thr Ile Gly Ser Val Ala Thr Glu Asp Val Pro Arg Ile Leu Glu Lys
115 120 125

Ile Glu Asn Val
130

<210> SEQ ID NO 84
<211> LENGTH: 132
<212> TYPE: PRT
<213> ORGANISM: Porcine reproductive and respiratory syndrome virus

<400> SEQUENCE: 84

Arg Pro Lys Tyr Ser Ala Gln Ala Ile Ile Asp Ser Gly Gly Pro Cys
1 5 10 15

Ser Gly His Leu Gln Glu Val Lys Glu Thr Cys Leu Ser Val Met Arg
20 25 30

Glu Ala Cys Asp Ala Thr Lys Leu Asp Asp Pro Ala Thr Gln Glu Trp

```
        35                  40                  45

Leu Ser Arg Met Trp Asp Arg Val Asp Met Leu Thr Trp Arg Asn Thr
    50                  55                  60

Ser Val Tyr Gln Val Ile Cys Thr Leu Asp Gly Met Leu Lys Phe Leu
65                  70                  75                  80

Pro Lys Met Ile Leu Glu Thr Pro Pro Pro Tyr Pro Cys Glu Phe Val
                85                  90                  95

Met Met Pro His Thr Pro Ala Pro Ser Val Gly Ala Glu Ser Asp Leu
            100                 105                 110

Thr Ile Gly Ser Val Thr Thr Glu Asp Val Pro Arg Ile Leu Glu Lys
        115                 120                 125

Ile Gly Asn Val
    130


<210> SEQ ID NO 85
<211> LENGTH: 132
<212> TYPE: PRT
<213> ORGANISM: Porcine reproductive and respiratory syndrome virus

<400> SEQUENCE: 85

Arg Pro Lys Tyr Ser Ala Gln Ala Ile Ile Asp Ser Gly Gly Pro Tyr
1               5                   10                  15

Ser Gly His Leu Gln Glu Val Lys Glu Thr Cys Leu Ser Ile Met Ser
            20                  25                  30

Glu Ala Cys Asp Val Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val His Gln Ala Ser Arg Thr Leu Asp Asp Arg Phe Lys Phe Leu
65                  70                  75                  80

Pro Lys Met Ile Leu Glu Thr Pro Pro Pro Tyr Pro Cys Gly Phe Val
                85                  90                  95

Met Met Pro Arg Thr Pro Ala Pro Ser Val Gly Ala Glu Ser Asp Leu
            100                 105                 110

Thr Ile Gly Ser Val Ala Thr Glu Asp Val Pro Arg Ile Phe Gly Lys
        115                 120                 125

Val Asn Asp Val
    130


<210> SEQ ID NO 86
<211> LENGTH: 132
<212> TYPE: PRT
<213> ORGANISM: Porcine reproductive and respiratory syndrome virus

<400> SEQUENCE: 86

Arg Pro Lys Tyr Ser Ala Gln Ala Ile Ile Asp Ser Gly Gly Pro Tyr
1               5                   10                  15

Ser Gly His Leu Gln Glu Val Lys Glu Thr Cys Leu Ser Ile Met Ser
            20                  25                  30

Glu Ala Cys Asp Val Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Val His Gln Ala Ser Arg Thr Leu Asp Asp Arg Phe Lys Phe Leu
65                  70                  75                  80

Pro Lys Met Ile Leu Glu Thr Pro Pro Pro Tyr Pro Cys Gly Phe Val
                85                  90                  95
```

```
Met Met Pro Arg Thr Pro Ala Pro Ser Val Gly Ala Glu Ser Asp Leu
            100                 105                 110

Thr Ile Gly Ser Val Ala Thr Glu Asp Val Pro Arg Ile Phe Gly Lys
        115                 120                 125

Val Asn Asp Val
    130


<210> SEQ ID NO 87
<211> LENGTH: 132
<212> TYPE: PRT
<213> ORGANISM: Porcine reproductive and respiratory syndrome virus

<400> SEQUENCE: 87

Arg Pro Lys His Ser Ala Gln Ala Ile Ile Asp Leu Val Gly Pro Cys
1               5                   10                  15

Ser Gly His Leu Gln Glu Val Lys Glu Ile Cys Leu Ser Val Met Arg
            20                  25                  30

Glu Ala Cys Asp Ala Thr Lys Leu Asn Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Thr Leu Ser Thr Leu Asp Gly Trp Ser Arg Phe Leu
65                  70                  75                  80

Pro Lys Leu Ile Leu Glu Thr Pro Pro Pro Tyr Pro Cys Glu Phe Val
                85                  90                  95

Met Met Pro Tyr Thr Pro Ala Pro Ser Val Gly Ala Glu Ser Asp Leu
            100                 105                 110

Thr Ile Gly Ser Val Ala Thr Glu Asp Val Pro Arg Ile Leu Glu Asn
        115                 120                 125

Met Glu Asn Val
    130


<210> SEQ ID NO 88
<211> LENGTH: 131
<212> TYPE: PRT
<213> ORGANISM: Porcine reproductive and respiratory syndrome virus

<400> SEQUENCE: 88

Arg Pro Lys Tyr Ser Ala Gln Ala Ile Ile Asp Ser Gly Gly Pro Cys
1               5                   10                  15

Ser Gly His Leu Gln Glu Val Lys Glu Thr Cys Leu Ser Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Cys Asn Thr Ser
    50                  55                  60

Val Tyr Gln Ala Ile Cys Thr Leu Asp Gly Arg Leu Lys Phe Leu Pro
65                  70                  75                  80

Lys Leu Ile Leu Glu Thr Pro Pro Pro Tyr Pro Cys Glu Phe Val Met
                85                  90                  95

Met Pro His Thr Pro Ala Pro Ser Val Gly Ala Glu Ser Asp Leu Thr
            100                 105                 110

Ile Gly Ser Val Ala Thr Glu Asp Val Pro Arg Ile Leu Glu Lys Thr
        115                 120                 125

Glu Asn Val
    130
```

<210> SEQ ID NO 89
<211> LENGTH: 132
<212> TYPE: PRT
<213> ORGANISM: Porcine reproductive and respiratory syndrome virus

<400> SEQUENCE: 89

```
Arg Pro Lys Tyr Ser Ala Gln Ala Ile Ile Asn Ser Gly Gly Pro Cys
1               5                   10                  15

Cys Gly His Leu Gln Glu Val Lys Glu Lys Tyr Leu Asn Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ile Phe Gln Ala Pro Phe Thr Leu Ala Asp Lys Phe Lys Ser Leu
65                  70                  75                  80

Pro Lys Met Ile Leu Glu Thr Pro Pro Pro Tyr Pro Cys Gly Phe Val
                85                  90                  95

Met Met Pro Arg Thr Pro Ala Pro Ser Val Gly Ala Glu Ser Asp Leu
            100                 105                 110

Thr Val Gly Ser Val Ala Thr Glu Asp Val Pro Arg Ile Leu Gly Lys
        115                 120                 125

Val Gln Gly Val
    130
```

<210> SEQ ID NO 90
<211> LENGTH: 132
<212> TYPE: PRT
<213> ORGANISM: Porcine reproductive and respiratory syndrome virus

<400> SEQUENCE: 90

```
Arg Pro Lys Tyr Ser Ala Gln Ala Ile Ile Asn Ser Gly Gly Pro Cys
1               5                   10                  15

Cys Gly His Leu Gln Glu Val Lys Glu Lys Tyr Leu Asn Val Met Arg
            20                  25                  30

Glu Ala Cys Asp Ala Thr Lys Leu Asp Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ile Phe Gln Ala Pro Phe Thr Leu Ala Asp Lys Phe Lys Thr Leu
65                  70                  75                  80

Pro Lys Met Ile Leu Glu Thr Pro Pro Pro Tyr Pro Cys Gly Phe Val
                85                  90                  95

Met Met Pro Arg Thr Pro Ala Pro Ser Val Gly Ala Glu Ser Asp Leu
            100                 105                 110

Thr Val Gly Ser Val Ala Thr Glu Asp Val Pro Arg Ile Leu Gly Asn
        115                 120                 125

Val Gln Gly Val
    130
```

<210> SEQ ID NO 91
<211> LENGTH: 132
<212> TYPE: PRT
<213> ORGANISM: Porcine reproductive and respiratory syndrome virus

<400> SEQUENCE: 91

```
Arg Pro Arg Tyr Ser Ala Gln Ala Leu Ile Asp Arg Gly Gly Pro Leu
1               5                   10                  15
```

```
Ala Ala Val His Ala Lys Ile Lys Asn Arg Val Tyr Glu Gln Cys Leu
            20                  25                  30

Gln Ala Cys Glu Pro Gly Ser Arg Ala Thr Pro Ala Thr Lys Glu Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Lys Lys Asn Arg Ala
                85                  90                  95

Ser Asp Asn Ala Gly Leu Lys Gln Leu Val Ala Arg Trp Asp Lys Lys
            100                 105                 110

Leu Ser Val Thr Pro Pro Leu Lys Ser Ala Gly Leu Ala Leu Asp Gln
        115                 120                 125

Thr Val Pro Pro
    130


<210> SEQ ID NO 92
<211> LENGTH: 132
<212> TYPE: PRT
<213> ORGANISM: Porcine reproductive and respiratory syndrome virus

<400> SEQUENCE: 92

Arg Pro Arg Tyr Ser Ala Gln Ala Leu Ile Asp Arg Gly Gly Pro Leu
1               5                   10                  15

Ala Asp Val His Ala Lys Ile Lys Asn Arg Val Tyr Glu Gln Cys Leu
            20                  25                  30

Gln Ala Cys Glu Pro Gly Ser Arg Ala Thr Pro Ala Thr Lys Glu Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95

Ser Asp Asn Ala Gly Leu Arg Gln Leu Val Ala Arg Trp Asp Lys Lys
            100                 105                 110

Leu Ser Val Thr Pro Pro Pro Lys Ser Thr Gly Leu Val Leu Asp Gln
        115                 120                 125

Thr Val Pro Leu
    130


<210> SEQ ID NO 93
<211> LENGTH: 132
<212> TYPE: PRT
<213> ORGANISM: Porcine reproductive and respiratory syndrome virus

<400> SEQUENCE: 93

Arg Pro Arg Tyr Ser Ala Gln Ala Leu Ile Asp Arg Gly Gly Pro Leu
1               5                   10                  15

Ala Asp Val His Ala Lys Ile Lys Asn Arg Val Tyr Glu Gln Cys Leu
            20                  25                  30

Gln Ala Cys Glu Pro Gly Ser Arg Ala Thr Pro Ala Thr Lys Glu Trp
        35                  40                  45

Leu Asp Lys Met Trp Asp Arg Val Asp Met Lys Thr Trp Arg Cys Thr
    50                  55                  60
```

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Lys Lys Asn Arg Ala
85 90 95

Ser Asp Asn Ala Gly Leu Lys Gln Leu Val Ala Arg Trp Asp Lys Lys
100 105 110

Leu Ser Val Thr Pro Pro Pro Lys Ser Ala Gly Leu Val Leu Asn Gln
115 120 125

Thr Val Pro Pro
130

<210> SEQ ID NO 94
<211> LENGTH: 132
<212> TYPE: PRT
<213> ORGANISM: Porcine reproductive and respiratory syndrome virus

<400> SEQUENCE: 94

Arg Pro Arg Tyr Ser Ala Gln Ala Leu Ile Asp Arg Gly Gly Pro Leu
1 5 10 15

Ala Asp Val His Ala Lys Ile Lys Asn Arg Val Tyr Glu Gln Cys Leu
20 25 30

Gln Ala Cys Glu Pro Gly Ser Arg Ala Thr Pro Ala Thr Lys Glu Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Arg Gln Leu Val Ala Arg Trp Asp Lys Lys
100 105 110

Leu Ser Val Thr Pro Pro Pro Lys Ser Ala Gly Leu Val Leu Asp Gln
115 120 125

Thr Val Pro Pro
130

<210> SEQ ID NO 95
<211> LENGTH: 132
<212> TYPE: PRT
<213> ORGANISM: Porcine reproductive and respiratory syndrome virus

<400> SEQUENCE: 95

Arg Pro Arg Phe Ser Ala Gln Ala Leu Ile Asp Arg Gly Gly Pro Leu
1 5 10 15

Ala Asp Val His Ala Lys Ile Lys Asn Arg Val Tyr Glu Gln Cys Leu
20 25 30

Gln Ala Cys Glu Pro Gly Ser Arg Ala Thr Pro Ala Thr Arg Glu Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Val Thr Pro Pro Pro Lys Pro Val Gly Pro Val Leu Asp Gln

```
        115                 120                 125

Ile Val Pro Pro
    130


<210> SEQ ID NO 96
<211> LENGTH: 132
<212> TYPE: PRT
<213> ORGANISM: Porcine reproductive and respiratory syndrome virus

<400> SEQUENCE: 96

Arg Pro Arg Phe Ser Ala Gln Ala Leu Ile Asp Arg Gly Gly Pro Leu
1               5                   10                  15

Ala Asp Val His Ala Lys Ile Lys Asn Arg Val Tyr Glu Gln Cys Leu
            20                  25                  30

Gln Ala Cys Glu Pro Gly Ser Arg Ala Thr Pro Ala Thr Arg Glu Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95

Ser Asp Asn Ala Gly Leu Lys Gln Leu Val Ala Gln Trp Asp Arg Lys
            100                 105                 110

Leu Ser Val Thr Pro Pro Pro Lys Pro Val Gly Pro Val Leu Asp Gln
        115                 120                 125

Ile Val Pro Pro
    130


<210> SEQ ID NO 97
<211> LENGTH: 132
<212> TYPE: PRT
<213> ORGANISM: Porcine reproductive and respiratory syndrome virus

<400> SEQUENCE: 97

Arg Pro Arg Phe Ser Ala Gln Ala Leu Ile Asp Arg Gly Gly Pro Leu
1               5                   10                  15

Ala Asp Val His Ala Lys Ile Lys Asn Arg Val Tyr Glu Gln Cys Leu
            20                  25                  30

Gln Ala Cys Glu Pro Gly Ser Arg Ala Thr Pro Ala Thr Arg Glu Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95

Ser Asp Ser Thr Gly Leu Lys Gln Leu Val Ala Gln Trp Asp Arg Lys
            100                 105                 110

Leu Ser Val Ala Pro Pro Gln Lys Pro Val Gly Pro Val Arg Asn Gln
        115                 120                 125

Ala Val Pro Pro
    130


<210> SEQ ID NO 98
<211> LENGTH: 132
<212> TYPE: PRT
<213> ORGANISM: Porcine reproductive and respiratory syndrome virus
```

<400> SEQUENCE: 98

Arg Pro Arg Phe Ser Ala Gln Ala Leu Ile Asp Arg Gly Gly Pro Leu
1 5 10 15

Ala Asp Val His Ala Lys Ile Lys Asn Arg Val Tyr Glu Gln Cys Leu
20 25 30

Gln Ala Cys Glu Pro Gly Ser Arg Ala Thr Pro Ala Thr Arg Glu Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Val Thr Pro Pro Pro Lys Pro Val Gly Pro Val Leu Asp Gln
115 120 125

Ile Val Pro Pro
130

<210> SEQ ID NO 99
<211> LENGTH: 132
<212> TYPE: PRT
<213> ORGANISM: Porcine reproductive and respiratory syndrome virus

<400> SEQUENCE: 99

Arg Pro Arg Phe Ser Ala Gln Ala Leu Ile Asp Arg Gly Gly Pro Leu
1 5 10 15

Ala Asp Val His Ala Lys Ile Lys Asn Arg Val Tyr Glu Gln Cys Leu
20 25 30

Gln Ala Cys Glu Pro Gly Ser Arg Ala Thr Pro Ala Thr Arg Glu Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Val Thr Pro Pro Pro Lys Pro Val Gly Pro Val Leu Asp Gln
115 120 125

Thr Val Pro Pro
130

<210> SEQ ID NO 100
<211> LENGTH: 132
<212> TYPE: PRT
<213> ORGANISM: Porcine reproductive and respiratory syndrome virus

<400> SEQUENCE: 100

Arg Pro Arg Phe Ser Ala Gln Ala Leu Ile Asp Arg Gly Gly Pro Leu
1 5 10 15

Ala Asp Val His Ala Lys Ile Lys Asn Arg Val Tyr Glu Gln Cys Leu
20 25 30

Lys Ala Cys Glu Pro Gly Ser Arg Ala Thr Pro Ala Thr Lys Glu Trp

```
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95

Ser Asp Asn Ala Gly Leu Lys Gln Leu Val Ala Gln Trp Asp Arg Lys
            100                 105                 110

Phe Ser Val Thr Pro Pro Pro Lys Leu Ala Gly Pro Val Leu Asp Gln
        115                 120                 125

Thr Val Leu Pro
    130


<210> SEQ ID NO 101
<211> LENGTH: 132
<212> TYPE: PRT
<213> ORGANISM: Porcine reproductive and respiratory syndrome virus

<400> SEQUENCE: 101

Arg Pro Arg His Ser Ala Gln Ala Leu Ile Asp Arg Gly Gly Pro Leu
1               5                   10                  15

Ala Asp Val His Ala Lys Ile Lys Asn Arg Val Tyr Glu Gln Cys Leu
            20                  25                  30

Gln Ala Cys Glu Pro Gly Ser Arg Ala Thr Pro Ala Thr Arg Glu Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95

Ser Asp Asn Ala Gly Leu Lys Gln Leu Val Ala Arg Trp Asp Lys Lys
            100                 105                 110

Leu Ser Val Thr Pro Pro Pro Lys Ser Ala Gly Leu Val Leu Asp Gln
        115                 120                 125

Thr Val Pro Pro
    130


<210> SEQ ID NO 102
<211> LENGTH: 132
<212> TYPE: PRT
<213> ORGANISM: Porcine reproductive and respiratory syndrome virus

<400> SEQUENCE: 102

Arg Pro Arg Phe Ser Ala Gln Ala Leu Ile Asp Arg Gly Gly Pro Leu
1               5                   10                  15

Ala Asp Val His Ala Lys Ile Lys His Arg Val Tyr Glu Gln Cys Leu
            20                  25                  30

Gln Ala Cys Glu Pro Gly Ser Arg Ala Thr Pro Ala Thr Lys Lys Trp
        35                  40                  45

Leu Asp Lys Met Trp Asp Arg Val Asp Met Lys Thr Trp Arg Cys Thr
    50                  55                  60

Ser Gln Phe Gln Ala Gly Arg Ile Leu Ala Ser Leu Lys Phe Leu Pro
65                  70                  75                  80

Asp Met Ile Gln Asp Thr Pro Pro Pro Val Pro Arg Lys Asn Arg Ala
                85                  90                  95
```

Ser Asp Asn Ala Gly Leu Lys Gln Leu Val Ala Gln Trp Asp Arg Lys
100 105 110

Leu Ser Gly Thr Pro Pro Pro Lys Ser Ala Gly Leu Val Leu Asp Gln
115 120 125

Thr Val Pro Pro
130

<210> SEQ ID NO 103
<211> LENGTH: 132
<212> TYPE: PRT
<213> ORGANISM: Porcine reproductive and respiratory syndrome virus

<400> SEQUENCE: 103

Arg Pro Arg Phe Ser Ala Gln Ala Leu Ile Asp Arg Gly Gly Pro Leu
1 5 10 15

Ala Asp Val His Ala Lys Ile Lys His Arg Val Tyr Glu Gln Cys Leu
20 25 30

Gln Ala Cys Glu Pro Gly Ser Arg Ala Thr Pro Ala Thr Lys Lys Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Gly Thr Pro Pro Pro Lys Pro Ala Gly Ser Val Leu Asp Gln
115 120 125

Thr Val Pro Pro
130

<210> SEQ ID NO 104
<211> LENGTH: 132
<212> TYPE: PRT
<213> ORGANISM: Porcine reproductive and respiratory syndrome virus

<400> SEQUENCE: 104

Arg Pro Arg Phe Ser Ala Gln Ala Leu Ile Asp Arg Gly Gly Pro Leu
1 5 10 15

Ala Asp Val His Ala Lys Ile Lys His Arg Val Tyr Glu Gln Cys Leu
20 25 30

Gln Ala Cys Glu Pro Gly Ser Arg Ala Thr Pro Ala Thr Lys Lys Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Gly Thr Pro Pro Pro Lys Pro Ala Gly Ser Val Leu Asp Gln
115 120 125

Thr Val Pro Pro
130

<210> SEQ ID NO 105
<211> LENGTH: 132
<212> TYPE: PRT
<213> ORGANISM: Porcine reproductive and respiratory syndrome virus

<400> SEQUENCE: 105

Arg Pro Arg Phe Ser Ala Gln Ala Leu Ile Asp Arg Gly Gly Pro Leu
1 5 10 15

Ala Asp Val His Ala Lys Ile Lys His Arg Val Tyr Glu Gln Cys Leu
20 25 30

Gln Ala Cys Glu Pro Gly Ser Arg Ala Thr Pro Ala Thr Lys Lys Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Gly Thr Pro Pro Pro Lys Pro Ala Gly Ser Val Phe Asp Gln
115 120 125

Ala Val Pro Pro
130

<210> SEQ ID NO 106
<211> LENGTH: 132
<212> TYPE: PRT
<213> ORGANISM: Porcine reproductive and respiratory syndrome virus

<400> SEQUENCE: 106

Arg Pro Arg Phe Ser Ala Gln Ala Leu Ile Asp Arg Gly Gly Pro Leu
1 5 10 15

Ala Asp Val His Ala Lys Ile Lys His Arg Val Tyr Glu Gln Cys Leu
20 25 30

Gln Ala Cys Glu Pro Gly Ser Arg Ala Thr Pro Ala Thr Lys Lys Trp
35 40 45

Leu Asp Lys Met Trp Asp Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Gly Thr Pro Pro Pro Lys Pro Ala Gly Ser Val Leu Asp Gln
115 120 125

Ala Val Pro Pro
130

<210> SEQ ID NO 107
<211> LENGTH: 132
<212> TYPE: PRT
<213> ORGANISM: Porcine reproductive and respiratory syndrome virus

<400> SEQUENCE: 107

Arg Pro Arg Phe Ser Ala Gln Ala Leu Ile Asp Arg Gly Gly Pro Leu
1 5 10 15

Ala Asp Val His Ala Lys Ile Lys Asn Gln Val Tyr Glu Arg Cys Leu
20 25 30

Gln Ala Cys Glu Pro Gly Ser Arg Ala Thr Pro Ala Thr Arg Glu Trp
35 40 45

Leu Asp Lys Met Trp Glu Arg Val Asp Met Lys Thr Trp Arg Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Gly Leu Lys Gln Leu Val Ala Gln Trp Asp Arg Lys
100 105 110

Leu Ser Met Thr Ser Pro Gln Lys Pro Val Gly Ser Val Leu Asp Gln
115 120 125

Thr Ala Phe Pro
130

<210> SEQ ID NO 108
<211> LENGTH: 132
<212> TYPE: PRT
<213> ORGANISM: Porcine reproductive and respiratory syndrome virus

<400> SEQUENCE: 108

Arg Pro Arg Phe Ser Ala Gln Ala Leu Ile Asp Arg Gly Gly Pro Leu
1 5 10 15

Ala Asp Val His Ala Lys Ile Lys Asn Arg Val Tyr Glu Arg Cys Leu
20 25 30

Gln Ala Cys Glu Pro Gly Ser Arg Ala Thr Pro Ala Thr Lys Glu Trp
35 40 45

Leu Asp Lys Met Trp Asp Arg Val Asp Met Lys Thr Trp Cys Cys Thr
50 55 60

Ser Gln Phe Gln Ala Gly Arg Ile Leu Ala Ser Leu Lys Phe Leu Pro
65 70 75 80

Asp Met Ile Gln Asp Thr Pro Pro Pro Val Pro Arg Lys Asn Arg Ala
85 90 95

Ser Asp Asn Ala Asp Leu Lys Gln Leu Val Ala Gln Trp Asp Arg Lys
100 105 110

Leu Ser Met Thr Pro Pro Gln Lys Pro Val Glu Pro Val Leu Asp Gln
115 120 125

Thr Val Ser Pro
130

<210> SEQ ID NO 109
<211> LENGTH: 132
<212> TYPE: PRT
<213> ORGANISM: Porcine reproductive and respiratory syndrome virus

<400> SEQUENCE: 109

Arg Pro Lys Tyr Ser Ala Gln Ala Ile Ile Asp Leu Gly Gly Pro Cys
1 5 10 15

Ser Gly His Leu Gln Arg Glu Lys Glu Ala Cys Leu Arg Ile Met Arg
20 25 30

Glu Ala Cys Asp Ala Ala Lys Leu Ser Asp Pro Ala Thr Gln Glu Trp
35 40 45

Leu Ser Arg Met Trp Asp Arg Val Asp Met Leu Thr Trp Arg Asn Thr
50 55 60

```
Ser Ala Tyr Gln Ala Phe Arg Thr Leu Asp Gly Arg Phe Gly Phe Leu
65                  70                  75                  80

Pro Lys Met Ile Leu Glu Thr Pro Pro Pro Tyr Pro Cys Gly Phe Val
                85                  90                  95

Met Leu Pro His Thr Pro Ala Pro Ser Val Ser Ala Glu Ser Asp Leu
            100                 105                 110

Thr Ile Gly Ser Val Ala Thr Glu Asp Ile Pro Arg Ile Leu Gly Lys
        115                 120                 125

Ile Glu Asn Thr
    130


<210> SEQ ID NO 110
<211> LENGTH: 132
<212> TYPE: PRT
<213> ORGANISM: Porcine reproductive and respiratory syndrome virus

<400> SEQUENCE: 110

Arg Pro Lys Tyr Ser Ala Gln Ala Ile Ile Asp Ser Gly Gly Pro Cys
1               5                   10                  15

Ser Gly His Leu Gln Lys Glu Lys Glu Ala Cys Leu Arg Ile Met Arg
            20                  25                  30

Glu Ala Cys Asp Ala Ala Arg Leu Gly Asp Pro Ala Thr Gln Glu Trp
        35                  40                  45

Leu Ser His Met Trp Asp Arg Val Asp Val Leu Thr Trp Arg Asn Thr
    50                  55                  60

Ser Val Tyr Gln Ala Phe Arg Thr Leu Asp Gly Arg Phe Gly Phe Leu
65                  70                  75                  80

Pro Lys Met Ile Leu Glu Thr Pro Pro Pro Tyr Pro Cys Gly Phe Val
                85                  90                  95

Met Leu Pro His Thr Pro Thr Pro Ser Val Ser Ala Glu Ser Asp Leu
            100                 105                 110

Thr Ile Gly Ser Val Ala Thr Glu Asp Val Pro Arg Ile Leu Gly Lys
        115                 120                 125

Thr Glu Asn Thr
    130


<210> SEQ ID NO 111
<211> LENGTH: 132
<212> TYPE: PRT
<213> ORGANISM: Porcine reproductive and respiratory syndrome virus

<400> SEQUENCE: 111

Arg Pro Lys Tyr Ser Ala Gln Ala Ile Ile Asp Ser Gly Gly Pro Cys
1               5                   10                  15

Ser Gly His Leu Gln Arg Glu Lys Glu Ala Cys Leu Ser Ile Met Arg
            20                  25                  30

Glu Ala Cys Asp Ala Ala Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Leu His Thr Leu Asp Gly Arg Ser Gly Phe Leu
65                  70                  75                  80

Pro Lys Met Ile Leu Glu Thr Pro Pro Pro His Pro Cys Gly Phe Val
                85                  90                  95

Met Leu Pro His Thr Pro Ala Pro Ser Val Ser Ala Lys Ser Asp Leu
            100                 105                 110

Thr Ile Gly Ser Val Ala Thr Glu Asp Val Pro Arg Ile Leu Gly Lys
```

```
        115                 120                 125

Ile Glu Asn Thr
    130


<210> SEQ ID NO 112
<211> LENGTH: 132
<212> TYPE: PRT
<213> ORGANISM: Porcine reproductive and respiratory syndrome virus

<400> SEQUENCE: 112

Arg Pro Lys Tyr Ser Ala Gln Ala Ile Ile Asp Ser Gly Gly Pro Cys
1               5                   10                  15

Ser Gly His Leu Arg Arg Glu Lys Glu Ala Cys Leu Ser Ile Met Arg
            20                  25                  30

Lys Ala Cys Asp Ala Ala Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Leu Arg Val Leu Asp Gly Arg Phe Gly Phe Leu
65                  70                  75                  80

Pro Lys Met Ile Leu Glu Thr Pro Pro Pro Tyr Pro Cys Gly Phe Val
                85                  90                  95

Met Leu Pro His Thr Pro Ala Pro Ser Val Ser Ala Glu Ser Asp Leu
            100                 105                 110

Thr Ile Gly Ser Val Ala Thr Glu Asp Val Pro Arg Ile Leu Gly Lys
        115                 120                 125

Thr Glu Asn Ala
    130


<210> SEQ ID NO 113
<211> LENGTH: 132
<212> TYPE: PRT
<213> ORGANISM: Porcine reproductive and respiratory syndrome virus

<400> SEQUENCE: 113

Arg Pro Lys His Ser Ala Gln Ala Ile Ile Asp Ser Gly Gly Pro Cys
1               5                   10                  15

Ser Gly His Leu Arg Arg Glu Lys Glu Ala Cys Leu Ser Ile Met Arg
            20                  25                  30

Glu Ala Cys Asp Ala Ala Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Phe Arg Ile Leu Asp Gly Arg Phe Glu Phe Leu
65                  70                  75                  80

Pro Lys Met Ile Leu Glu Thr Pro Pro Pro Tyr Pro Cys Gly Phe Val
                85                  90                  95

Met Leu Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Gly Lys
        115                 120                 125

Ile Glu Asn Ala
    130


<210> SEQ ID NO 114
<211> LENGTH: 132
<212> TYPE: PRT
<213> ORGANISM: Porcine reproductive and respiratory syndrome virus
```

-continued

```
<400> SEQUENCE: 114

Arg Pro Lys His Ser Ala Gln Ala Ile Ile Asp Ser Gly Gly Pro Cys
1               5                   10                  15

Ser Gly His Leu Arg Arg Glu Lys Glu Ala Cys Leu Ser Ile Met Arg
            20                  25                  30

Glu Ala Cys Asp Ala Ala Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Phe Arg Ile Leu Asp Gly Arg Phe Glu Phe Leu
65                  70                  75                  80

Pro Lys Met Ile Leu Glu Thr Pro Pro Pro Tyr Pro Cys Gly Phe Val
                85                  90                  95

Met Leu Pro His Thr Pro Ala Pro Ser Val Gly Ala Glu Ser Asp Leu
            100                 105                 110

Thr Ile Gly Ser Val Ala Thr Glu Asp Val Pro Arg Ile Leu Gly Lys
        115                 120                 125

Ile Glu Asn Ala
    130


<210> SEQ ID NO 115
<211> LENGTH: 132
<212> TYPE: PRT
<213> ORGANISM: Porcine reproductive and respiratory syndrome virus

<400> SEQUENCE: 115

Arg Pro Lys Tyr Ser Ala Gln Ala Ile Ile Asp Phe Gly Gly Pro Cys
1               5                   10                  15

Ser Gly His Leu Gln Lys Glu Lys Glu Ala Cys Leu Ser Ile Met Arg
            20                  25                  30

Glu Ala Cys Asp Ala Ser Lys Leu Ser Asp Pro Ala Thr Gln Glu Trp
        35                  40                  45

Leu Ser Arg Met Trp Asp Arg Val Asp Met Leu Thr Trp Arg Asn Thr
    50                  55                  60

Ser Ala Tyr Gln Ala Phe Arg Thr Leu Asn Gly Arg Phe Glu Phe Leu
65                  70                  75                  80

Pro Lys Met Ile Leu Glu Thr Pro Pro Pro His Pro Cys Gly Phe Val
                85                  90                  95

Met Leu Pro His Thr Pro Ala Pro Ser Val Ser Ala Glu Ser Asp Leu
            100                 105                 110

Thr Ile Gly Ser Val Ala Thr Glu Asp Val Pro Arg Ile Leu Gly Lys
        115                 120                 125

Ile Gly Asp Thr
    130
```